US006352830B1

(12) United States Patent
Crabtree et al.

(10) Patent No.: US 6,352,830 B1
(45) Date of Patent: *Mar. 5, 2002

(54) NF-AT POLYPEPTIDES AND POLYNUCLEOTIDES AND SCREENING METHODS FOR IMMUNOSUPPRESSIVE AGENTS

(75) Inventors: Gerald R. Crabtree, Woodside; Jeffrey P. Northrop, Campbell; Steffan N. Ho, San Diego; William M. Flanagan, Menlo Park, all of CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/232,346

(22) Filed: Jan. 15, 1999

Related U.S. Application Data

(63) Continuation-in-part of application No. 08/507,032, filed on Jul. 31, 1995, now Pat. No. 5,989,810, and a continuation-in-part of application No. 08/260,174, filed on Jun. 13, 1994, now Pat. No. 6,197,925, which is a continuation of application No. 08/228,944, filed on Apr. 18, 1994, now abandoned, which is a continuation-in-part of application No. 08/124,981, filed on Sep. 20, 1993, now Pat. No. 5,837,840, which is a continuation of application No. 07/749,385, filed on Aug. 22, 1991, now abandoned.

(51) Int. Cl.[7] .......................... C12Q 1/68; G01N 33/53; C07H 21/04; C07K 14/435

(52) U.S. Cl. ................................ 435/6; 435/4; 435/7.1; 435/15; 435/21; 536/24.1; 536/23.5; 530/350

(58) Field of Search ........................... 435/6, 4, 7.1, 15, 435/21; 536/24.1, 23.5; 530/350

(56) References Cited

U.S. PATENT DOCUMENTS

| | | | |
|---|---|---|---|
| 5,656,452 A | 8/1997 | Rao et al. | 435/69.1 |
| 5,837,840 A | 11/1998 | Crabtree et al. | 530/350 |
| 6,096,515 A | 8/2000 | Crabtree et al. | 435/69.1 |
| 6,150,099 A | 11/2000 | Crabtree et al. | 435/69.1 |
| 6,171,781 B1 | 1/2001 | Crabtree et al. | 435/4 |

FOREIGN PATENT DOCUMENTS

| | | |
|---|---|---|
| WO | WO 93/04203 | 3/1993 |
| WO | WO 94/15964 | 7/1994 |
| WO | WO 95/02053 | 1/1995 |
| WO | WO 95/08554 | 3/1995 |

OTHER PUBLICATIONS

Clipstone N. and Crabtree, G., "Calcineurin is a key signaling enzyme in T lymphocyte activation and the target of the immunosuppressive drugs cyclosporin A and FK506", Ann. N.Y. Acad. Sci. 696:20–30 (1993).

Clipstone, N. and Crabtree, G., "Identification of calcineurin as a key signaling enzyme in T–lymphocyte activation", Nature 357(6380):695–97 (1992).

Crabtree, G., "Pathways of T lymphocyte activation", Abstract of NIH Grant No. R01CA39612 (1988).

Crabtree, G., "Pathways of T lymphocyte activation", Abstract of NIH Grant No. R01CA39612 (1991).

Jain, et al., "The T cell transcription factor NF–Atp is a substrate for calcineurin and interacts with Fos and Jun", Nature 365(6444):352–55 (1993).

Banerji, S. et al., "The immunosuppressant FK–506 specifically inhibits mitogen–induced activation of the interleukin–2 promoter and the isolated enhancer elements NFIL–2A and NF–AT1", Mol. Cell. Biol., 11(8): 4074–4087 1991.

Bierer, B. et al., "Two distinct signal transmission pathways in T lymphocytes are inhibited by complexes formed between an immunophilin and either FK506 or rapamycin", Proc. Natl. Acad. Sci. USA., 87: 9231–9235 (1990).

Crabtree, G., "Contingent genetic regulatory events in T lymphocyte activation", Science, 243: 355–361 (1989).

Crabtree, G. and Clipstone, N., "Signal transmission between the plasma membrane and nucleus of T lymphocyte", Ann. Rev. Biochem., 63: 1045–1083 (1994).

(List continued on next page.)

Primary Examiner—Carla J. Myers
(74) Attorney, Agent, or Firm—Ropes & Gray; Matthew P. Vincent

(57) ABSTRACT

The invention provides novel polypeptides which are associated with the transcription complex NF-AT, polynucleotides encoding such polypeptides, antibodies which are reactive with such polypeptides, polynucleotide hybridization probes and PCR amplification probes for detecting polynucleotides which encode such polypeptides, transgenes which encode such polypeptides, homologous targeting constructs that encode such polypeptides and/or homologously integrate in or near endogenous genes encoding such polypeptides, nonhuman transgenic animals which comprise functionally disrupted endogenous genes that normally encode such polypeptides, and transgenic nonhuman animals which comprise transgenes encoding such polypeptides. The invention also provides methods for detecting T cells (including activated T cells) in a cellular sample, methods for treating hyperactive or hypoactive T cell conditions, methods for screening for immunomodulatory agents, methods for diagnostic staging of lymphocyte differentiation, methods for producing NF-AT proteins for use as research or diagnostic reagents, methods for producing antibodies reactive with the novel polypeptides, and methods for producing transgenic nonhuman animals. Also included are methods and agents for activation of NF-AT dependent transcription, including agents which interfere with the production, modification of nuclear or cytoplasmic subunits, or the nuclear import of the cytoplasmic subunits. In particular, screening tests for novel immunosuppressants are provided based upon the ability of NF-AT to activate transcription.

21 Claims, 31 Drawing Sheets

OTHER PUBLICATIONS

Durand, D. et al., "Characterization of antigen receptor response elements within the interleukin–2 enhancer ", *Mol. Cell. Biol.*, 8(2): 1715–1724 (1988).

Emmel, E. et al. "Cyclosporin A specifically inhibits function of nuclear proteins involved in T cell activation", *Science* 346:1617–1620 (1989).

Flanagan, W. et al., "Nuclear association of a T–cell transcription factor blocked by FK–506 and cyclosporin A", *Nature*, 352:803–807 (1991).

Ho, S. et al., "Cloning and characterization of NF–$AT_c$ and NF–$AT_p$ :the cytoplasmic components of NF–AT", *Adv. Exp. Med. Biol.* 365:167 (1994).

Israel, A., "NF–AT comes under control", *Nature*, 369: 443–444 (1994).

Jain, J. et al., "Nuclear factor of activated T cells contains Fos and Jun", *Nature*, 356: 801–804 (1992).

Jain, et al. "Analysis of the preexisting and nuclear forms of nuclear factor of activated T cells." *J. Immunol.*, 151(2): 837–848 (1993).

Jin, Y. et al., "Molecular cloning of a membrane–associated human FK–506–and rapamycin–binding protein, FKBP–13", *Proc. Natl., Acad. Sci. USA.*, 88: 6677–6681 (1991).

Matilla, P. et al., "The actions of cyclosporin A and FK506 suggest a novel step in the activation of T lymphocytes", *EMBO J.*, 9(13): 4425–4433 (1990).

McCaffrey, et al. "NF–ATp, a T lymphocyte DNA–binding protein that is a target for calcineurin and immunosuppressive drugs", *J. Biol. Chem.*, 268(5): 3747–3752 (1993).

McCaffrey, et al. "Isolation of the cyclosproin–sensitive T cell transcription factor NFATp", *Science*, 262: 750–754 (1993).

Northrop, et al. "Characterization of the nuclear and cytoplasmic components of the lymphoid–specific nuclear factor of activated T cells (NF–AT) complex", *J. Biol. Chem.*, 268(4): 2917–2923 (1993).

Northrop, et al. "NF–AT components define a family of transcription factors targeted in T–cell activation", *Nature*, 369: 497–502 (1994).

Rao, A., "NF–$AT_p$ : a transcription factor required for the co–ordinate induction of several cytokine genes", *Immunology Today*, 15(6): 274–281 (1994).

Riegel, J. et al., "Nuclear Events after activation of CD4 $^+8^+$thymocytes" *J. Immunology*, 144(9): 3611–3618 (1990).

Shaw, J. et al., "Identification of a putative regulator of early T cell activation genes", *Science*, 241: 202–25 (1988).

Schmidt, A. et al., "Inducible Nuclear Factor Binding to the κB elements of the human immunodeficiency virus enhancer in T cells can be blocked by cyclosporin A in a signal–dependent manner", *J. Virology*, 64(8): 4037–4041 (1990).

Schreiber, S., "Chemistry and biology of the immunophilins and their immunosuppressive ligands", *Science*, 251: 283–287 (1991).

Verweij, C. et al., Cell type specificity and activation requirements for NFAT–1 (Nuclear Factor of Activated T–cells) transcriptional activity determined by a new method using transgenic mice to assay transcriptional activity of an individual.

U.S. application No. 08/145,006, Rao et al., filed May 11, 1993.

U.S. application No. 08/017,052, Rao et al., filed Nov. 02, 1993.

U.S. application No. 08/006067, Rao et al., filed Jan. 15, 1993.-

| Cytoplasmic extract | - | - | | ns | ns | ns | ns |
|---|---|---|---|---|---|---|---|
| anisomycin | - | - | | - | - | + | + |
| Nuclear extract | s+F | s+F | | s+F | s+F | s+F | s+F |
| anisomycin | - | + | | - | + | - | + |

1  2      3  4  5  6

|  | | | | Competing oligos | | | | | |
|---|---|---|---|---|---|---|---|---|---|
| | | | | NF-AT | | | Mutant NF-AT | | |
| Cytoplasmic extract | ns | s | s+F | ns | s | s+F | ns | s | s+F |
| Nuclear extract | ns | ns | ns | s+F | s+F | s+F | s+F | s+F | s+F |
| | 1 | 2 | 3 | 4 | 5 | 6 | 7 | 8 | 9 |

Fig. 6B

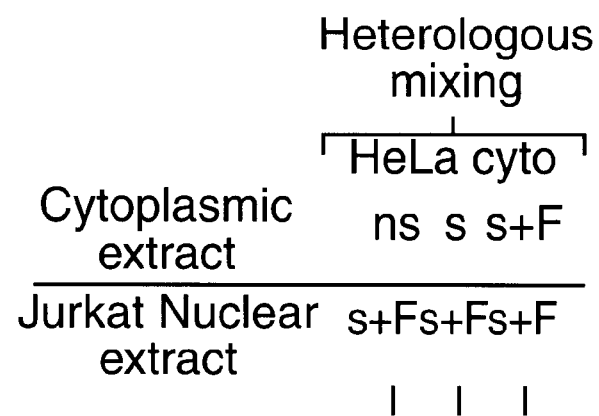
1  2  3
Fig. 7C

```
                  10              30              50              70              90
                   .               .               .               .               .
       gaattccgcagggcgcgggcaccggggcgcgggcagggctcggagccaccgcgcaggtcctagggccgcggccgggcccgccacgcgcgcacacgcccc
                  110             130             150             170             190
                   .               .               .               .               .
       tcgatgactttcctccggggcgcgcggcgctgagcccggggcgagggctgtcttcccggagacccgaccccggcagcgcggggcggccacttctcctgtg
                  210             230             250             270             290
                   .               .               .               .               .
       cctccgcccgctgctccactcccgccgccgccgcgcggatgccaagcaccagctttccagtcccttccaagtttccacttggccctgcggctgcggtct
  1                                              M  P  S  T  S  F  P  V  P  S  K  F  P  L  G  P  A  A  A  V  F    21
                  310             330             350             370             390
                   .               .               .               .               .
       tcgggagaggagaaactttggggcccgcgccgcgccggcggcaccatgaagtcagcggaggaagaacactatggctatgcatcctccaacgtcagccc
 22    G  R  G  E  T  L  G  P  A  P  R  A  G  G  T  M  K  S  A  E  E  E  H  Y  G  Y  A  S  S  N  V  S  P       54
                  410             430             450             470             490
                   .               .               .               .               .
       cgccctgccgctccccacggcgcactccaccctgccggcccgtgccacaaccttcagacctccacaccgggcatcatcccgccggcggatcacccctcg
 55    A  L  P  L  P  T  A  H  S  T  L  P  A  P  C  H  N  L  Q  T  S  T  P  G  I  I  P  P  A  D  H  P  S       87
                  510             530             550             570             590
                   .               .               .               .               .
       gggtacggagcagctttggacggtgggcccgcgggctacttcctctcctccggccacacccaggcctgatggggcccctgccctggagagtcctcgcatcg
 88    G  Y  G  A  A  L  D  G  G  P  A  G  Y  F  L  S  S  G  H  T  R  P  D  G  A  P  A  L  E  S  P  R  I  E  121
                  610             630             650             670             690
                   .               .               .               .               .
       agataacctcgtgcttgggcctgtaccacaacaataaccagttttccacgatgtggaggtggaagacgtcctccctagctccaaacggtcccctccac
122    I  T  S  C  L  G  L  Y  H  N  N  Q  F  F  H  D  V  E  V  E  D  V  L  P  S  S  K  R  S  P  S  T      154
                  710             730             750             770             790
                   .               .               .               .               .
       ggccacgctgagtctgcccagcctggaggcctacagagacccctcgtgcctgagcccggccagcagcctgtcctcccggagctgcaactcagaggcctcc
155    A  T  L  S  L  P  S  L  E  A  Y  R  D  P  S  C  L  S  P  A  S  S  L  S  S  R  C  N  S  E  A  S      187
                  810             830             850             870             890
                   .               .               .               .               .
       tcctacgagtccaactactcgtacccgtacgcgtcccccccagacgtcgccatggcagtctccctgcgtgtctcccaagaccacggaccccgaggagggct
188    S  Y  E  S  N  Y  S  Y  P  Y  A  S  P  Q  T  S  P  W  Q  S  P  C  V  S  P  K  T  T  D  P  E  E  G  F  221
                  910             930             950             970             990
                   .               .               .               .               .
       ttccccgcgggctgggggcctgcacactgctgggttccccgcagcactcccctccacctcgccccgcgccagcgtcactgaggagagctggctgggtgc
222    P  R  G  L  G  A  C  T  L  L  G  S  P  Q  H  S  P  S  T  S  P  R  A  S  V  T  E  E  S  W  L  G  A  254
                 1010            1030            1050            1070            1090
                   .               .               .               .               .
       ccgctcctccagacccgcgtcccccttgcaacaagaggaagtacagcctcaacggccggcagccgccctactcaccccaccactcgcccacgccgtccccg
255    R  S  S  R  P  A  S  P  C  N  K  R  K  Y  S  L  N  G  R  Q  P  P  Y  S  P  H  H  S  P  T  P  S  P  287
                 1110            1130            1150            1170            1190
                   .               .               .               .               .
       cacggctcccccgcgggtcagcgtgaccgacgactcgtggttgggcaacaccacccagtacaccagctcggccatcgtggccgccatcaacgcgctgacca
288    H  G  S  P  R  V  S  V  T  D  D  S  W  L  G  N  T  T  Q  Y  T  S  S  A  I  V  A  A  I  N  A  L  T  T 321
```

Fig. 12A

```
                    1210          1230          1250          1270          1290
        ccgacagcagcctggacctgggagatggcgtccctgtcaagtcccgcaagaccaccctggagcagccgccctcagtggcgctcaaggtggagcccgtcgg
    322 D  S  S  L  D  L  G  D  G  V  P  V  K  S  R  K  T  T  L  E  Q  P  P  S  V  A  L  K  V  E  P  V  G  354
                    1310          1330          1350          1370          1390
        ggaggacctgggcagccccccgcccccggccgacttcgcgcccgaagactactcctctttccagcacatcaggaagggcggcttctgcgaccagtacctg
    355 E  D  L  G  S  P  P  P  P  A  D  F  A  P  E  D  Y  S  S  F  Q  H  I  R  K  G  G  F  C  D  Q  Y  L  387
                    1410          1430          1450          1470          1490
        gcggtgccgcagcaccccctaccagtgggcgaagcccaagcccctgtcccctacgtcctacatgagcccgaccctgcccgcccggactggcagctgccgt
    388 A  V  P  Q  H  P  Y  Q  W  A  K  P  K  P  L  S  P  T  S  Y  M  S  P  T  L  P  A  L  D  W  Q  L  P  S  421
                    1510          1530          1550          1570          1590
        cccactcaggcccgtatgagcttcggattgaggtgcagcccaagtcccaccaccgagcccactacgagacggagggcagccggggggccgtgaaggcgtc
    422 H  S  G  P  Y  E  L  R  I  E  V  Q  P  K  S  H  H  R  A  H  Y  E  T  E  G  S  R  G  A  V  K  A  S  454
                    1610          1630          1650          1670          1690
        ggccggaggacaccccatcgtgcagctgcatggctacttggagaatgagccgctgatgctgcagcttttcattgggacggcggacgaccgcctgctgcgc
    455 A  G  G  H  P  I  V  Q  L  H  G  Y  L  E  N  E  P  L  M  L  Q  L  F  I  G  T  A  D  D  R  L  L  R  487
                    1710          1730          1750          1770          1790
        ccgcacgccttctaccaggtgcaccgcatcacagggaagaccgtgtccaccaccagccacgaggctatcctctccaacaccaaagtcctggagatcccac
    488 P  H  A  F  Y  Q  V  H  R  I  T  G  K  T  V  S  T  T  S  H  E  A  I  L  S  N  T  K  V  L  E  I  P  L  521
                    1810          1830          1850          1870          1890
        tcctgccggagaacagcatgcgagccgtcattgactgtgccggaatcctgaaactcagaaactccgacattgaacttcggaaaggagagacggacatcgg
    522 L  P  E  N  S  M  R  A  V  I  D  C  A  G  I  L  K  L  R  N  S  D  I  E  L  R  K  G  E  T  D  I  G  554
                    1910          1930          1950          1970          1990
        gaggaagaacacacgggtacggctggtgttccgcgttcacgtcccgcaacccagcggccgcacgctgtccctgcaggtggcctccaacccatcgaatgc
    555 R  K  N  T  R  V  R  L  V  F  R  V  H  V  P  Q  P  S  G  R  T  L  S  L  Q  V  A  S  N  P  I  E  C  587
                    2010          2030          2050          2070          2090
        tcccagcgctcagctcaggagctgcctctggtggagaagcagagcacggacagctatccggtcgtgggcgggaagaagatggtcctgtctggccacaact
    588 S  Q  R  S  A  Q  E  L  P  L  V  E  K  Q  S  T  D  S  Y  P  V  V  G  G  K  K  M  V  L  S  G  H  N  F  621
                    2110          2130          2150          2170          2190
        tcctgcaggactccaaggtcatttcgtggagaaagcccccagatggccaccatgtctgggagatggaagcgaaaactgaccgggacctgtgcaagccgaa
    622 L  Q  D  S  K  V  I  F  V  E  K  A  P  D  G  H  H  V  W  E  M  E  A  K  T  D  R  D  L  C  K  P  N  654
                    2210          2230          2250          2270          2290
        ttctctggtggttgagatcccgccatttcggaatcagaggataaccagccccgttcacgtcagtttctacgtctgcaacgggaagagaaagcgaagccag
    655 S  L  V  V  E  I  P  P  F  R  N  Q  R  I  T  S  P  V  H  V  S  F  Y  V  C  N  G  K  R  K  R  S  Q  687
                    2310          2330          2350          2370          2390
        taccagcgtttcacctaccttcccgccaacggtaacgccatctttctaaccgtaagccgtgaacatgagcgcgtggggtgcttttttctaaagacgcagaa
    688 Y  Q  R  F  T  Y  L  P  A  N  G  N  A  I  F  L  T  V  S  R  E  H  E  R  V  G  C  F  F           716
```

Fig. 12B

```
          2410                2430                2450                2470                2490
            .         .         .         .         .         .         .         .         .         .
acgacgtcgccgtaaagcagcgtggcgtgttgcacatttaactgtgtgatgtcccgttagtgagaccgagccatcgatgccctgaaaaggaaaggaaaag
          2510                2530                2550                2570                2590
            .         .         .         .         .         .         .         .         .         .
ggaagcttcggatgcatttccttgatccctgttgggggtggggggcgggggttgcatactcagatagtcacggttattttgcttcttgcgaatgtataa
          2610                2630                2650                2670                2690
            .         .         .         .         .         .         .         .         .         .
cagccaaggggaaaacatggctcttctgctccaaaaaaactgaggggggtcctggtgtgcatttgcaccctaaagctgcttacggtgaaaaggcaaataggt
          2710                2730                2750
            .         .         .         .         .
atagctattttgcaggcacctttaggaataaactttgcttttaaaaaaaaa
```

Fig. 12C

| | | | |
|---|---|---|---|
| DMDORSAL | TKNVRKKPYVKITE-QPAGKALRFRYECEGRSAGSIPGVNSTPENKT | | |
| C-REL | MASGLYNPYIEIIE-QPRQRGMRFRYKCEGRSAGSIPQEHSTDNNRT | | |
| NFKB p50 | IPLSTDGPYLQILE-QPKQRGFRFRYVCEGPSHGGLPGASSEKNKKS | | |
| NFKB p65 | EPAQASGPYVEHIE-QPKQRGMRFRYKCEGRSAGSIPGERSTDTTKT | | |
| NFATc | QLPSHSGPYELRIEVQPKSH—HRAHYETEG—SRGAVKASAGG— | | |
| NFATp | PLSNQSGSYELRIEVQPKPH—HRAHYETEG—SRGAVKAPTGG— | | |
| | 418 | * | * | 457 |

| | | | |
|---|---|---|---|
| DMDORSAL | YPTIEIVGYKGRAVVVSCVTKDTPYRP-HPHNLVGKEGCK-KGVCTLEI | | |
| C-REL | YPSINIMNYYGRGKVRITLVTKNDPYKP-HPHDLVGKD-CR-DGYYEAEF | | |
| NFKB p50 | YPQVKICNYVGPAKVIVQLVTNGKNIHL-HAHSLVGKH-CE-DGVCTVTA | | |
| NFKB p65 | HPTIKINGYTGPGTVRISLVTKDPPHRP-HPHELVGKD-CR-DGYYEADL | | |
| NFATc | HPIVQLHGYLENEPLMLQLFIGTADDRLLRPHAFYQV—HRITGKTVSTT | | |
| NFATp | HPVVQLHGYMENKPLGLQIFIGTADERILKPHAFYQV—HRITGKTVTTT | | |
| | 458 | * | * | 505 |

| | | | |
|---|---|---|---|
| DMDORSAL | NSE-TMRAVFSNLGIQCVKKKDIEAALKAR-EEIRVDPFKTGFSHRF— | | |
| C-REL | GNE-RRPLFFQNLGIRCVKRCVKKEVKEAIITRIKAG-INPFN— | | |
| NFKB p50 | GPK-DMVVGFANLGILHVT-KKKVFETLEARMTEACIRGYNPGLLVHSDL | | |
| NFKB p65 | CPDRDSIHSFQNLGIQCVKKRDLEQAIS-QRIQTNNPFH— | | |
| NFATc | SHE-AILSNTKVLEIPLLPENSMRAVIDCAGILKLRNS— | | |
| NFATp | SYE-KIVGNTKVLEIPLEPKNNMRATIDCAGILKLRNA— | | |
| | 506 | * | * | 542 |

SEQUENCE LISTING

<160> NUMBER OF SEQ ID NOS: 62

<210> SEQ ID NO 1
<211> LENGTH: 36
<212> TYPE: DNA
<213> ORGANISM: human

<400> SEQUENCE: 1
ttcctccggg gcgcgcggcg tgagcccggg gcgagg    36

<210> SEQ ID NO 2
<211> LENGTH: 42
<212> TYPE: DNA
<213> ORGANISM: human

<400> SEQUENCE: 2
cagcgcgggg cggccacttc tcctgtgcct ccgcccgctg ct    42

<210> SEQ ID NO 3
<211> LENGTH: 42
<212> TYPE: DNA
<213> ORGANISM: human

```
<210> SEQ ID NO 3
<211> LENGTH: 42
<212> TYPE: DNA
<213> ORGANISM: human

<400> SEQUENCE: 3
gccgcgcgga tgccaagcac cagctttcca gtcccttcca ag              42

<210> SEQ ID NO 4
<211> LENGTH: 42
<212> TYPE: DNA
<213> ORGANISM: human

<400> SEQUENCE: 4
ccaacgtcag ccccgccctg ccgctcccca cggcgcactc ca              42

<210> SEQ ID NO 5
<211> LENGTH: 36
<212> TYPE: DNA
<213> ORGANISM: human

<400> SEQUENCE: 5
ttcagacctc cacaccgggc atcatcccgc cggcgg                     36

<210> SEQ ID NO 6
<211> LENGTH: 42
<212> TYPE: DNA
<213> ORGANISM: human

<400> SEQUENCE: 6
gccacaccag gcctgatggg gcccctgccc tggagagtcc tc              42

<210> SEQ ID NO 7
<211> LENGTH: 42
<212> TYPE: DNA
<213> ORGANISM: human

<400> SEQUENCE: 7
agtctgccca gcctggaggc ctacagagac ccctcgtgcc tg              42

<210> SEQ ID NO 8
<211> LENGTH: 39
<212> TYPE: DNA
<213> ORGANISM: human

<400> SEQUENCE: 8
gtgtctccca agaccacgga ccccgaggag ggctttccc                  39

<210> SEQ ID NO 9
<211> LENGTH: 42
<212> TYPE: DNA
<213> ORGANISM: human

<400> SEQUENCE: 9
agctggctgg gtgcccgctc ctccagaccc gcgtcccctt gc              42

<210> SEQ ID NO 10
<211> LENGTH: 42
<212> TYPE: DNA
<213> ORGANISM: human

<400> SEQUENCE: 10
tacagcctca acggccggca gccgccctac tcaccccacc ac              42

<210> SEQ ID NO 11
<211> LENGTH: 42
<212> TYPE: DNA
<213> ORGANISM: human
```

-continued

<400> SEQUENCE: 11
gaccaccgac agcagcctgg acctgggaga tggcgtccct gt          42

<210> SEQ ID NO 12
<211> LENGTH: 42
<212> TYPE: DNA
<213> ORGANISM: human

<400> SEQUENCE: 12
cctgggcagc cccccgcccc cggccgactt cgcgcccgaa ga          42

<210> SEQ ID NO 13
<211> LENGTH: 42
<212> TYPE: DNA
<213> ORGANISM: human

<400> SEQUENCE: 13
gctcccctac cagtggcgaa gcccaagccc ctgtcccta cg           42

<210> SEQ ID NO 14
<211> LENGTH: 42
<212> TYPE: DNA
<213> ORGANISM: human

<400> SEQUENCE: 14
cttcggattg aggtgcagcc caagtcccac caccgagccc ac          42

<210> SEQ ID NO 15
<211> LENGTH: 42
<212> TYPE: DNA
<213> ORGANISM: human

<400> SEQUENCE: 15
catggctact tggagaatga gccgctgatg ctgcagcttt tc          42

<210> SEQ ID NO 16
<211> LENGTH: 42
<212> TYPE: DNA
<213> ORGANISM: human

<400> SEQUENCE: 16
aagaccgtgt ccaccaccag ccacgaggct atcctctcca ac          42

<210> SEQ ID NO 17
<211> LENGTH: 42
<212> TYPE: DNA
<213> ORGANISM: human

<400> SEQUENCE: 17
tcagctcagg agctgcctct ggtggagaag cagagcacgg ac          42

<210> SEQ ID NO 18
<211> LENGTH: 40
<212> TYPE: DNA
<213> ORGANISM: human

<400> SEQUENCE: 18
aacgccatct ttctaaccgt aagccgtgaa catgagcgcg             40

<210> SEQ ID NO 19
<211> LENGTH: 38
<212> TYPE: DNA

-continued

<210> SEQ ID NO 19
<211> LENGTH: 38
<212> TYPE: DNA
<213> ORGANISM: human

<400> SEQUENCE: 19
agaaacgacg tcgccgtaaa gcagcgtggc gtgtggca                    38

<210> SEQ ID NO 20
<211> LENGTH: 41
<212> TYPE: DNA
<213> ORGANISM: human

<400> SEQUENCE: 20
gcatactcag atagtcacgg ttattttgct tcttgcgaat g                41

<210> SEQ ID NO 21
<211> LENGTH: 36
<212> TYPE: DNA
<213> ORGANISM: human

<400> SEQUENCE: 21
agggcgcggg caccggggcg cgggcagggc tcggag                      36

<210> SEQ ID NO 22
<211> LENGTH: 36
<212> TYPE: DNA
<213> ORGANISM: human

<400> SEQUENCE: 22
gcaagaagca aaataaccgt gactatctga gtatgc                      36

<210> SEQ ID NO 23
<211> LENGTH: 13
<212> TYPE: PRT
<213> ORGANISM: human

<400> SEQUENCE: 23

Ser Pro Arg Ala Ser Val Thr Glu Glu Ser Trp Leu Gly
 1               5                  10

<210> SEQ ID NO 24
<211> LENGTH: 13
<212> TYPE: PRT
<213> ORGANISM: human

<400> SEQUENCE: 24

Ser Pro Arg Val Ser Val Thr Asp Asp Ser Trp Leu Gly
 1               5                  10

<210> SEQ ID NO 25
<211> LENGTH: 16
<212> TYPE: PRT
<213> ORGANISM: human

<400> SEQUENCE: 25

Asn Ala Ile Phe Leu Thr Val Ser Arg Glu His Glu Arg Val Gly Cys
 1               5                  10                  15

<210> SEQ ID NO 26
<211> LENGTH: 18
<212> TYPE: PRT
<213> ORGANISM: human

<400> SEQUENCE: 26

Leu His Gly Tyr Leu Glu Asn Glu Pro Leu Met Leu Gln Leu Phe Ile
 1               5                  10                  15

Gly Thr

<210> SEQ ID NO 27
<211> LENGTH: 16
<212> TYPE: PRT
<213> ORGANISM: human

<400> SEQUENCE: 27

Pro Ser Thr Ser Pro Arg Ala Ser Val Thr Glu Glu Ser Trp Leu Gly
 1               5                  10                  15

<210> SEQ ID NO 28
<211> LENGTH: 19
<212> TYPE: PRT
<213> ORGANISM: human

<400> SEQUENCE: 28

Gly Pro Ala Pro Arg Ala Gly Gly Thr Met Lys Ser Ala Glu Glu Glu
 1               5                  10                  15

His Tyr Gly

<210> SEQ ID NO 29
<211> LENGTH: 10
<212> TYPE: PRT
<213> ORGANISM: human

<400> SEQUENCE: 29

Ala Ser Ala Gly Gly His Pro Ile Val Gln
 1               5                  10

<210> SEQ ID NO 30
<211> LENGTH: 10
<212> TYPE: PRT
<213> ORGANISM: human

<400> SEQUENCE: 30

Asn Thr Arg Val Arg Leu Val Phe Arg Val
 1               5                  10

<210> SEQ ID NO 31
<211> LENGTH: 22
<212> TYPE: PRT
<213> ORGANISM: human

<400> SEQUENCE: 31

Ala Lys Thr Asp Arg Asp Leu Cys Lys Pro Asn Ser Leu Val Val Glu
 1               5                  10                  15

Ile Pro Pro Phe Arg Asn
            20

<210> SEQ ID NO 32
<211> LENGTH: 18
<212> TYPE: PRT
<213> ORGANISM: human

<400> SEQUENCE: 32

Glu Val Gln Pro Lys Ser His His Arg Ala His Tyr Glu Thr Glu Gly
 1               5                  10                  15

Ser Arg

<210> SEQ ID NO 33
<211> LENGTH: 15

-continued

```
<212> TYPE: PRT
<213> ORGANISM: human

<400> SEQUENCE: 33

Ser Pro Arg Val Ser Val Thr Asp Asp Ser Trp Leu Gly Asn Thr
 1               5                  10                  15

<210> SEQ ID NO 34
<211> LENGTH: 16
<212> TYPE: PRT
<213> ORGANISM: human

<400> SEQUENCE: 34

Ser His His Arg Ala His Tyr Glu Thr Glu Gly Ser Arg Gly Ala Val
 1               5                  10                  15

<210> SEQ ID NO 35
<211> LENGTH: 17
<212> TYPE: PRT
<213> ORGANISM: human

<400> SEQUENCE: 35

Leu Arg Asn Ser Asp Ile Glu Leu Arg Lys Gly Glu Thr Asp Ile Gly
 1               5                  10                  15

Arg

<210> SEQ ID NO 36
<211> LENGTH: 13
<212> TYPE: PRT
<213> ORGANISM: human

<400> SEQUENCE: 36

Thr Leu Ser Leu Gln Val Ala Ser Asn Pro Ile Glu Cys
 1               5                  10

<210> SEQ ID NO 37
<211> LENGTH: 13
<212> TYPE: PRT
<213> ORGANISM: human

<400> SEQUENCE: 37

Val Lys Ala Ser Ala Gly Gly His Pro Ile Val Gln Leu
 1               5                  10

<210> SEQ ID NO 38
<211> LENGTH: 716
<212> TYPE: PRT
<213> ORGANISM: human

<400> SEQUENCE: 38

Met Pro Ser Thr Ser Phe Pro Val Pro Ser Lys Phe Pro Leu Gly Pro
 1               5                  10                  15

Ala Ala Ala Val Phe Gly Arg Gly Glu Thr Leu Gly Pro Ala Pro Arg
                20                  25                  30

Ala Gly Gly Thr Met Lys Ser Ala Glu Glu His Tyr Gly Tyr Ala
        35                  40                  45

Ser Ser Asn Val Ser Pro Ala Leu Pro Leu Pro Thr Ala His Ser Thr
    50                  55                  60

Leu Pro Ala Pro Cys His Asn Leu Gln Thr Ser Thr Pro Gly Ile Ile
65                  70                  75                  80

Pro Pro Ala Asp His Pro Ser Gly Tyr Gly Ala Ala Leu Asp Gly Cys
                85                  90                  95
```

```
Pro Ala Gly Tyr Phe Leu Ser Ser Gly His Thr Arg Pro Asp Gly Ala
            100                 105                 110

Pro Ala Leu Glu Ser Pro Arg Ile Glu Ile Thr Ser Cys Leu Gly Leu
            115                 120                 125

Tyr His Asn Asn Asn Gln Phe Phe His Asp Val Glu Val Glu Asp Val
            130                 135                 140

Leu Pro Ser Ser Lys Arg Ser Pro Ser Thr Ala Thr Leu Ser Leu Pro
145                 150                 155                 160

Ser Leu Glu Ala Tyr Arg Asp Pro Ser Cys Leu Ser Pro Ala Ser Ser
                165                 170                 175

Leu Ser Ser Arg Ser Cys Asn Ser Glu Ala Ser Ser Tyr Glu Ser Asn
            180                 185                 190

Tyr Ser Tyr Pro Tyr Ala Ser Pro Gln Thr Ser Pro Trp Gln Ser Pro
            195                 200                 205

Cys Val Ser Pro Lys Thr Thr Asp Pro Glu Glu Gly Phe Pro Arg Gly
            210                 215                 220

Leu Gly Ala Cys Thr Leu Leu Gly Ser Pro Gln His Ser Pro Ser Thr
225                 230                 235                 240

Ser Pro Arg Ala Ser Val Thr Glu Glu Ser Trp Leu Gly Ala Arg Ser
                245                 250                 255

Ser Arg Pro Ala Ser Pro Cys Asn Lys Arg Lys Tyr Ser Leu Asn Gly
            260                 265                 270

Arg Gln Pro Pro Tyr Ser Pro His His Ser Pro Thr Pro Ser Pro His
            275                 280                 285

Gly Ser Pro Arg Val Ser Val Thr Asp Asp Ser Trp Leu Gly Asn Thr
            290                 295                 300

Thr Gln Tyr Thr Ser Ser Ala Ile Val Ala Ala Ile Asn Ala Leu Thr
305                 310                 315                 320

Thr Asp Ser Ser Leu Asp Leu Gly Asp Gly Val Pro Val Lys Ser Arg
                325                 330                 335

Lys Thr Thr Leu Glu Gln Pro Pro Ser Val Ala Leu Lys Val Glu Pro
            340                 345                 350

Val Gly Glu Asp Leu Gly Ser Pro Pro Pro Ala Asp Phe Ala Pro
            355                 360                 365

Glu Asp Tyr Ser Ser Phe Gln His Ile Arg Lys Gly Gly Phe Cys Asp
            370                 375                 380

Gln Tyr Leu Ala Val Pro Gln His Pro Tyr Gln Trp Ala Lys Pro Lys
385                 390                 395                 400

Pro Leu Ser Pro Thr Ser Tyr Met Ser Pro Thr Leu Pro Ala Leu Asp
            405                 410                 415

Trp Gln Leu Pro Ser His Ser Gly Pro Tyr Glu Leu Arg Ile Glu Val
            420                 425                 430

Gln Pro Lys Ser His His Arg Ala His Tyr Glu Thr Glu Gly Ser Arg
            435                 440                 445

Gly Ala Val Lys Ala Ser Ala Gly Gly His Pro Ile Val Gln Leu His
450                 455                 460

Gly Tyr Leu Glu Asn Glu Pro Leu Met Leu Gln Leu Phe Ile Gly Thr
465                 470                 475                 480

Ala Asp Asp Arg Leu Leu Arg Pro His Ala Phe Tyr Gln Val His Arg
                485                 490                 495

Ile Thr Gly Lys Thr Val Ser Thr Thr Ser His Glu Ala Ile Leu Ser
            500                 505                 510
```

-continued

```
Asn Thr Lys Val Leu Glu Ile Pro Leu Leu Pro Glu Asn Ser Met Arg
        515                 520                 525
Ala Val Ile Asp Cys Ala Cys Ile Leu Lys Leu Arg Asn Ser Asp Ile
        530                 535                 540
Glu Leu Arg Lys Gly Glu Thr Asp Ile Gly Arg Lys Asn Thr Arg Val
545                 550                 555                 560
Arg Leu Val Phe Arg Val His Val Pro Gln Pro Ser Gly Arg Thr Leu
                565                 570                 575
Ser Leu Gln Val Ala Ser Asn Pro Ile Glu Cys Ser Gln Arg Ser Ala
                580                 585                 590
Gln Glu Leu Pro Leu Val Glu Lys Gln Ser Thr Asp Ser Tyr Pro Val
                595                 600                 605
Val Gly Gly Lys Lys Met Val Leu Ser Gly His Asn Phe Leu Gln Asp
        610                 615                 620
Ser Lys Val Ile Phe Val Glu Lys Ala Pro Asp Gly His His Val Trp
625                 630                 635                 640
Glu Met Glu Ala Lys Thr Asp Arg Asp Leu Cys Lys Pro Asn Ser Leu
                645                 650                 655
Val Val Glu Ile Pro Pro Phe Arg Asn Gln Arg Ile Thr Ser Pro Val
                660                 665                 670
His Val Ser Phe Tyr Val Cys Asn Gly Lys Arg Lys Arg Ser Gln Tyr
                675                 680                 685
Gln Arg Phe Thr Tyr Leu Pro Ala Asn Gly Asn Ala Ile Phe Leu Thr
        690                 695                 700
Val Ser Arg Glu His Glu Arg Val Gly Cys Phe Phe
705                 710                 715

<210> SEQ ID NO 39
<211> LENGTH: 30
<212> TYPE: DNA
<213> ORGANISM: human

<400> SEQUENCE: 39
acgcccaaag aggaaaattt gtttcataca                              30

<210> SEQ ID NO 40
<211> LENGTH: 9
<212> TYPE: PRT
<213> ORGANISM: human

<400> SEQUENCE: 40

Leu Arg Asn Ala Asp Ile Glu Leu Arg
  1               5

<210> SEQ ID NO 41
<211> LENGTH: 6
<212> TYPE: PRT
<213> ORGANISM: human

<400> SEQUENCE: 41

Gly Glu Thr Asp Ile Gly
  1               5

<210> SEQ ID NO 42
<211> LENGTH: 6
<212> TYPE: PRT
<213> ORGANISM: human

<400> SEQUENCE: 42
```

```
Arg Asn Ala Asp Ile Glu
  1               5
```

<210> SEQ ID NO 43
<211> LENGTH: 18
<212> TYPE: DNA
<213> ORGANISM: human
<220> FEATURE:
<223> OTHER INFORMATION: "n" at positions 3, 9 represent inosine

<400> SEQUENCE: 43
mgnaaygcng ayathgar                                                 18

<210> SEQ ID NO 44
<211> LENGTH: 18
<212> TYPE: DNA
<213> ORGANISM: human
<220> FEATURE:
<223> OTHER INFORMATION: "n" at positions 1, 10, 16 represent inosine

<400> SEQUENCE: 44
nccdatrtcn gtytcncc                                                 18

<210> SEQ ID NO 45
<211> LENGTH: 5502
<212> TYPE: DNA
<213> ORGANISM: human
<220> FEATURE:
<221> NAME/KEY: CDS
<222> LOCATION: (240)..(2387)

<400> SEQUENCE: 45
gaattccgca gggcgcgggc accggggcgc gggcagggct cggagccacc gcgcaggtcc    60
tagggccgcg gccgggcccc gccacgcgcg cacacgcccc tcgatgactt tcctccgggg   120
cgcgcggcgc tgagcccggg gcgagggctg tcttcccgga acccgacccc cggcagcgcg   180
gggcggccat ttctcctgtg cctccgcccg ctgctccact cccgccgcc gccgcgcgg   239

```
atg cca agc acc agc ttt cca gtc cct tcc aag ttt cca ctt ggc cct     287
Met Pro Ser Thr Ser Phe Pro Val Pro Ser Lys Phe Pro Leu Gly Pro
  1               5                  10                  15 gag gct gcg gtc ttc ggg aga gga gaa act ttg ggg ccc gcg ccg cgc     335
Glu Ala Ala Val Phe Gly Arg Gly Glu Thr Leu Gly Pro Ala Pro Arg
                 20                  25                  30 gcc ggc ggc acc atg aag tca gcg gag gaa gaa cac tat ggc tat gca     383
Ala Gly Gly Thr Met Lys Ser Ala Glu Glu Glu His Tyr Gly Tyr Ala
             35                  40                  45 tcc tcc aac gtc agc ccc gcc ctg ccg ctc ccc acg gcg cac tcc acc     431
Ser Ser Asn Val Ser Pro Ala Leu Pro Leu Pro Thr Ala His Ser Thr
         50                  55                  60 ctg ccg gcc ccg tgc cac aac ctt cag acc tcc aca ccg ggc atc atc     479
Leu Pro Ala Pro Cys His Asn Leu Gln Thr Ser Thr Pro Gly Ile Ile
     65                  70                  75                  80 ccg ccg gcg gac cac ccc tcg ggg tac gga gca gct ttg gac ggt ggg     527
Pro Pro Ala Asp His Pro Ser Gly Tyr Gly Ala Ala Leu Asp Gly Gly
                     85                  90                  95 ccc gcg ggc tac ttc ctc tcc tcc ggc cac acc agg cct gat cgg gcc     575
Pro Ala Gly Tyr Phe Leu Ser Ser Gly His Thr Arg Pro Asp Arg Ala
                100                 105                 110 cct gcc ctg gag agt cct cgc atc gag ata acc tcg tgc ttg ggc ctg     623
Pro Ala Leu Glu Ser Pro Arg Ile Glu Ile Thr Ser Cys Leu Gly Leu
            115                 120                 125 tac cac aac aat aac cag ttt ttc cac gat gtg gag gtg gaa gac gtc     671
```

-continued

```
Tyr His Asn Asn Asn Gln Phe Phe His Asp Val Glu Val Asp Val
    130                 135                 140 ctc cct agc tcc aaa cgg tcc ccc tcc acg gcc acg ctg agt ctg ccc    719
Leu Pro Ser Ser Lys Arg Ser Pro Ser Thr Ala Thr Leu Ser Leu Pro
145                 150                 155                 160 agc ctg gag gcc tac aga gac ccc tcg tgc ctg agc ccg gcc agc agc    767
Ser Leu Glu Ala Tyr Arg Asp Pro Ser Cys Leu Ser Pro Ala Ser Ser
                165                 170                 175 ctg tcc tcc cgg agc tgc aac tca gag gcc tcc tcc tac gag tcc aac    815
Leu Ser Ser Arg Ser Cys Asn Ser Glu Ala Ser Ser Tyr Glu Ser Asn
            180                 185                 190 tac tcg tac ccg tac gcg tcc ccc cag acg tcg cca tgg cag tct ccc    863
Tyr Ser Tyr Pro Tyr Ala Ser Pro Gln Thr Ser Pro Trp Gln Ser Pro
        195                 200                 205 tgc gtg tct ccc aag acc acg gac ccc gag gag ggc ttt ccc cgc ggg    911
Cys Val Ser Pro Lys Thr Thr Asp Pro Glu Glu Gly Phe Pro Arg Gly
    210                 215                 220 ctg ggg gcc tgc aca ctg ctg ggt tcc ccg cag cac tcc ccc tcc acc    959
Leu Gly Ala Cys Thr Leu Leu Gly Ser Pro Gln His Ser Pro Ser Thr
225                 230                 235                 240 tcg ccc cgc gcc agc gtc act gag gag agc tgg ctg ggt gcc cgc tcc   1007
Ser Pro Arg Ala Ser Val Thr Glu Glu Ser Trp Leu Gly Ala Arg Ser
                245                 250                 255 tcc aga ccc gcg tcc cct tgc aac aag agg aag tac agc ctc aac ggc   1055
Ser Arg Pro Ala Ser Pro Cys Asn Lys Arg Lys Tyr Ser Leu Asn Gly
            260                 265                 270 cgg cag ccg ccc tac tca ccc cac cac tcg ccc acg ccg tcc ccg cac   1103
Arg Gln Pro Pro Tyr Ser Pro His His Ser Pro Thr Pro Ser Pro His
        275                 280                 285 ggc tcc ccg agg gtc agc gtg acc gac gac tcg tgg ttg ggc aac acc   1151
Gly Ser Pro Arg Val Ser Val Thr Asp Asp Ser Trp Leu Gly Asn Thr
    290                 295                 300 acc cag tac acc agc tcg gcc atc gtg gcc gcc atc aac gag ctg acc   1199
Thr Gln Tyr Thr Ser Ser Ala Ile Val Ala Ala Ile Asn Glu Leu Thr
305                 310                 315                 320 acc gac agc agc ctg gac ctg gga gat ggc gtc cct gtc aag tcc cgc   1247
Thr Asp Ser Ser Leu Asp Leu Gly Asp Gly Val Pro Val Lys Ser Arg
                325                 330                 335 aag acc acc ctg gag cag cag ccc tca gtg gcg ctc aag gtg gag ccc   1295
Lys Thr Thr Leu Glu Gln Gln Pro Ser Val Ala Leu Lys Val Glu Pro
            340                 345                 350 gtc ggg gag gac ctg ggc agc ccc ccg ccc gcc gac ttc gcg ccc        1343
Val Gly Glu Asp Leu Gly Ser Pro Pro Pro Ala Asp Phe Ala Pro
        355                 360                 365 gaa gac tac tcc tct ttc cag cac atc agg aag ggc ggc ttc tgc gac   1391
Glu Asp Tyr Ser Ser Phe Gln His Ile Arg Lys Gly Gly Phe Cys Asp
370                 375                 380 cag tac ctg gcg gtg ccg cag cac ccc tac cag tgg gcg aag ccc aag   1439
Gln Tyr Leu Ala Val Pro Gln His Pro Tyr Gln Trp Ala Lys Pro Lys
385                 390                 395                 400 ccc ctg tcc cct acg tcc tac atg agc ccg acc ctg ccc gcc ctg gac   1487
Pro Leu Ser Pro Thr Ser Tyr Met Ser Pro Thr Leu Pro Ala Leu Asp
                405                 410                 415 tgg cag ctg ccg tcc cac tca ggc ccg tat gag ctt cgg att gag gtg   1535
Trp Gln Leu Pro Ser His Ser Gly Pro Tyr Glu Leu Arg Ile Glu Val
            420                 425                 430 cag ccc aag tcc cac cac cga gcc cac tac gag acg gag ggc agc cgg   1583
Gln Pro Lys Ser His His Arg Ala His Tyr Glu Thr Glu Gly Ser Arg
        435                 440                 445
```

-continued

```
ggg gca gtg aag gcg tcg gcc gga gga cac ccc atc gtg cag ctg cat    1631
Gly Ala Val Lys Ala Ser Ala Gly Gly His Pro Ile Val Gln Leu His
    450                 455                 460 ggc tac ttg gag aat gag ccg ctg atg ctg cag ctt ttc att ggg acg    1679
Gly Tyr Leu Glu Asn Glu Pro Leu Met Leu Gln Leu Phe Ile Gly Thr
465                 470                 475                 480 gcg gac gac cgc ctg ctg cgc ccg cac gcc ttc tac cag gtg cac cgc    1727
Ala Asp Asp Arg Leu Leu Arg Pro His Ala Phe Tyr Gln Val His Arg
                485                 490                 495 atc aca ggg aag acc gtg tcc acc acc agc cac gag gct atc ctc tcc    1775
Ile Thr Gly Lys Thr Val Ser Thr Thr Ser His Glu Ala Ile Leu Ser
            500                 505                 510 aac acc aaa gtc ctg gag atc cca ctc ctg ccg gag aac agc atg cga    1823
Asn Thr Lys Val Leu Glu Ile Pro Leu Leu Pro Glu Asn Ser Met Arg
        515                 520                 525 gcc gtc att gac tgt gcc gga atc ctg aaa ctc aga aac tcc gac att    1871
Ala Val Ile Asp Cys Ala Gly Ile Leu Lys Leu Arg Asn Ser Asp Ile
    530                 535                 540 gaa ctt cgc aaa gga gag acg gac atc ggg agg aag aac aca cgg gta    1919
Glu Leu Arg Lys Gly Glu Thr Asp Ile Gly Arg Lys Asn Thr Arg Val
545                 550                 555                 560 cgg ctg gtg ttc cgc gtt cac gtc ccg caa ccc agc ggc cgc acg ctg    1967
Arg Leu Val Phe Arg Val His Val Pro Gln Pro Ser Gly Arg Thr Leu
                565                 570                 575 tcc ctg cag gtg gcc tcc aac ccc atc gaa tgc tcc cag cgc tca gct    2015
Ser Leu Gln Val Ala Ser Asn Pro Ile Glu Cys Ser Gln Arg Ser Ala
            580                 585                 590 cag gag ctg cct ctg gtg gag aag cag agc acg gac agc tat ccg gtc    2063
Gln Glu Leu Pro Leu Val Glu Lys Gln Ser Thr Asp Ser Tyr Pro Val
        595                 600                 605 gtg ggc ggg aag aag atg gtc ctg tct ggc cac aac ttc ctg cag gac    2111
Val Gly Gly Lys Lys Met Val Leu Ser Gly His Asn Phe Leu Gln Asp
    610                 615                 620 tcc aag gtc att ttc gtg gag aaa gcc cca gat ggc cac cat gtc tgg    2159
Ser Lys Val Ile Phe Val Glu Lys Ala Pro Asp Gly His His Val Trp
625                 630                 635                 640 gag atg gaa gcg aaa act gac cgg gac ctg tgc aag ccg aat tct ctg    2207
Glu Met Glu Ala Lys Thr Asp Arg Asp Leu Cys Lys Pro Asn Ser Leu
                645                 650                 655 gtg gtt gag atc ccg cca ttt cgg aat cag agg ata acc agc ccc gtt    2255
Val Val Glu Ile Pro Pro Phe Arg Asn Gln Arg Ile Thr Ser Pro Val
            660                 665                 670 cac gtc agt ttc tac gtc tgc aac ggg aag aga aag gga agc cag tac    2303
His Val Ser Phe Tyr Val Cys Asn Gly Lys Arg Lys Gly Ser Gln Tyr
        675                 680                 685 cag cgt ttc acc tac ctt ccc gcc aac ggt aac gcc atc ttt cta acc    2351
Gln Arg Phe Thr Tyr Leu Pro Ala Asn Gly Asn Ala Ile Phe Leu Thr
    690                 695                 700 gta agc cgt gaa cat gag cgc gtg ggg tgc ttt ttc taaagacgca         2397
Val Ser Arg Glu His Glu Arg Val Gly Cys Phe Phe
705                 710                 715 gaaacgacgt cgccgtaaag cagcgtggcg tgttgcacat ttaactgtgt gatgtcccgt  2457
tagtgagacc gagccatcga tgccctgaaa aggaaaggaa aagggaagct tcggatgcat  2517
tttccttgat ccctgttggg ggtgggggc gggggttgca tactcagata gtcacggtta   2577
ttttgcttct tgcgaatgta taacagccaa ggggaaaaca tggctcttct gctccaaaaa  2637
actgaggggg tcctggtgtg catttgcacc ctaaagctgc ttacggtgaa aaggcaaata  2697
ggtatagcta ttttgcaggc acctttagga ataaactttg cttttaaaaa aaaagaattc  2757
```

-continued

```
cgcagggcgc gggcaccggg gcgcgggcag ggctcggagc caccgcgcag gtcctagggc    2817
cgcggccggg ccccgccacg cgcgcacacg ccccctcgatg actttcctcc ggggcgcgcg    2877
gcgctgagcc cggggcgagg gctgtcttcc cggagaccccg accccggcag cgcggggcgg    2937
ccatttctcc tgtgcctccg cccgctgctc cactccccgc cgccgccgcg cggatgccaa    2997
gcaccagctt tccagtccct tccaagttttc cacttggccc tgaggctgcg gtcttcggga    3057
gaggagaaac tttggggccc cgcgccgcgcg ccggcggcac catgaagtca gcggaggaag    3117
aacactatgg ctatgcatcc tccaacgtca gccccgccct gccgctcccc acggcgcact    3177
ccaccctgcc ggccccgtgc cacaaccttc agacctccac accgggcatc atcccgccgg    3237
cggaccaccc ctcggggtac ggagcagctt tggacggtgg gcccgcgggc tacttcctct    3297
cctccggcca caccaggcct gatcgggccc ctgccctgga gagtcctcgc atcgagataa    3357
cctcgtgctt gggcctgtac cacaacaata accagtttttt ccacgatgtg gaggtggaag    3417
acgtcctccc tagctccaaa cggtcccccct ccacggccac gctgagtctg cccagcctgg    3477
aggcctacag agacccctcg tgcctgagcc cggccagcag cctgtcctcc cggagctgca    3537
actcagaggc ctcctcctac gagtccaact actcgtaccc gtacgcgtcc ccccagacgt    3597
cgccatggca gtctccctgc gtgtctccca agaccacgga ccccgaggag ggctttcccc    3657
gcgggctggg ggcctgcaca ctgctggggtt ccccgcagca ctcccccctcc acctcgcccc    3717 gcgccagcgt cactgaggag agctggctgg gtgcccgctc ctccagaccc gcgtcccctt    3777
gcaacaagag gaagtacagc ctcaacggcc ggcagccgcc ctactcaccc caccactcgc    3837
ccacgccgtc cccgcacggc tccccgaggg tcagcgtgac cgacgactcg tggttgggca    3897
acaccaccca gtacaccagc tcggccatcg tggccgccat caacgagctg accaccgaca    3957
gcagcctgga cctgggagat ggcgtccctg tcaagtcccg caagaccacc ctggagcagc    4017
agccctcagt ggcgctcaag gtggagcccg tcggggagga cctgggcagc cccccgcccc    4077
cggccgactt cgcgcccgaa gactactcct ctttccagca catcaggaag ggcggcttct    4137
gcgaccagta cctggcggtg ccgcagcacc cctaccagtg ggcgaagccc aagcccctgt    4197
cccctacgtc ctacatgagc ccgacccctgc ccgccctgga ctggcagctg ccgtcccact    4257
caggcccgta tgagcttcgg attgaggtgc agcccaagtc ccaccaccga gcccactacg    4317
agacggaggg cagccggggg gcagtgaagg cgtcggccgg aggacacccc atcgtgcagc    4377
tgcatggcta cttggagaat gagccgctga tgctgcagct tttcattggg acggcggacg    4437
accgcctgct gcgcccgcac gccttctacc aggtgcaccg catcacagggg aagaccgtgt    4497 ccaccaccag ccacgaggct atcctctcca acaccaaagt cctggagatc ccactcctgc    4557
cggagaacag catgcgagcc gtcattgact gtgccggaat cctgaaactc agaaactccg    4617
acattgaact tcgcaaagga gagacggaca tcggggagga gaacacacgg gtacggctgg    4677
tgttccgcgt tcacgtcccg caacccagcg gccgcacgct gtccctgcag gtggcctcca    4737
accccatcga atgctcccag cgctcagctc aggagctgcc tctggtggag aagcagagca    4797
cggacagcta tccggtcgtg ggcgggaaga agatggtcct gtctggccac aacttcctgc    4857
aggactccaa ggtcatttttc gtggagaaag ccccagatgg ccaccatgtc tgggagatgg    4917
aagcgaaaac tgaccgggac ctgtgcaagc cgaattctct ggtggttgag atcccgccat    4977
ttcggaatca gaggataacc agcccccgttc acgtcagttt ctacgtctgc aacgggaaga    5037
gaaagggaag ccagtaccag cgtttcacct accttcccgc caacggtaac gccatctttc    5097
```

-continued

```
taaccgtaag ccgtgaacat gagcgcgtgg ggtgcttttt ctaaagacgc agaaacgacg   5157
tcgccgtaaa gcagcgtggc gtgttgcaca tttaactgtg tgatgtcccg ttagtgagac   5217
cgagccatcg atgccctgaa aaggaaagga aaagggaagc ttcggatgca ttttccttga   5277
tccctgttgg gggtggggg cggggttgc atactcagat agtcacggtt attttgcttc     5337
ttgcgaatgt ataacagcca aggggaaaac atggctcttc tgctccaaaa aactgagggg   5397
gtcctggtgt gcatttgcac cctaaagctg cttacggtga aaaggcaaat aggtatagct   5457
attttgcagg cacctttagg aataaacttt gcttttaaaa aaaaa                   5502
```

<210> SEQ ID NO 46
<211> LENGTH: 716
<212> TYPE: PRT
<213> ORGANISM: human

<400> SEQUENCE: 46

```
Met Pro Ser Thr Ser Phe Pro Val Pro Ser Lys Phe Pro Leu Gly Pro
  1               5                  10                  15

Glu Ala Ala Val Phe Gly Arg Gly Glu Thr Leu Gly Pro Ala Pro Arg
                 20                  25                  30

Ala Gly Gly Thr Met Lys Ser Ala Glu Glu His Tyr Gly Tyr Ala
             35                  40                  45

Ser Ser Asn Val Ser Pro Ala Leu Pro Leu Pro Thr Ala His Ser Thr
     50                  55                  60

Leu Pro Ala Pro Cys His Asn Leu Gln Thr Ser Thr Pro Gly Ile Ile
 65                  70                  75                  80

Pro Pro Ala Asp His Pro Ser Gly Tyr Gly Ala Ala Leu Asp Gly Gly
                 85                  90                  95

Pro Ala Gly Tyr Phe Leu Ser Ser Gly His Thr Arg Pro Asp Arg Ala
            100                 105                 110

Pro Ala Leu Glu Ser Pro Arg Ile Glu Ile Thr Ser Cys Leu Gly Leu
            115                 120                 125

Tyr His Asn Asn Gln Phe Phe His Asp Val Glu Val Glu Asp Val
    130                 135                 140

Leu Pro Ser Ser Lys Arg Ser Pro Ser Thr Ala Thr Leu Ser Leu Pro
145                 150                 155                 160

Ser Leu Glu Ala Tyr Arg Asp Pro Ser Cys Leu Ser Pro Ala Ser Ser
                165                 170                 175

Leu Ser Ser Arg Ser Cys Asn Ser Glu Ala Ser Ser Tyr Glu Ser Asn
            180                 185                 190

Tyr Ser Tyr Pro Tyr Ala Ser Pro Gln Thr Ser Pro Trp Gln Ser Pro
        195                 200                 205

Cys Val Ser Pro Lys Thr Thr Asp Pro Glu Glu Gly Phe Pro Arg Gly
    210                 215                 220

Leu Gly Ala Cys Thr Leu Leu Gly Ser Pro Gln His Ser Pro Ser Thr
225                 230                 235                 240

Ser Pro Arg Ala Ser Val Thr Glu Glu Ser Trp Leu Gly Ala Arg Ser
                245                 250                 255

Ser Arg Pro Ala Ser Pro Cys Asn Lys Arg Lys Tyr Ser Leu Asn Gly
            260                 265                 270

Arg Gln Pro Pro Tyr Ser Pro His His Ser Pro Thr Pro Ser Pro His
        275                 280                 285

Gly Ser Pro Arg Val Ser Val Thr Asp Asp Ser Trp Leu Gly Asn Thr
    290                 295                 300
```

```
Thr Gln Tyr Thr Ser Ser Ala Ile Val Ala Ala Ile Asn Glu Leu Thr
305                 310                 315                 320

Thr Asp Ser Ser Leu Asp Leu Gly Asp Gly Val Pro Val Lys Ser Arg
            325                 330                 335

Lys Thr Thr Leu Glu Gln Gln Pro Ser Val Ala Leu Lys Val Glu Pro
                340                 345                 350

Val Gly Glu Asp Leu Gly Ser Pro Pro Pro Ala Asp Phe Ala Pro
        355                 360                 365

Glu Asp Tyr Ser Ser Phe Gln His Ile Arg Lys Gly Gly Phe Cys Asp
    370                 375                 380

Gln Tyr Leu Ala Val Pro Gln His Pro Tyr Gln Trp Ala Lys Pro Lys
385                 390                 395                 400

Pro Leu Ser Pro Thr Ser Tyr Met Ser Pro Thr Leu Pro Ala Leu Asp
                405                 410                 415

Trp Gln Leu Pro Ser His Ser Gly Pro Tyr Glu Leu Arg Ile Glu Val
                420                 425                 430

Gln Pro Lys Ser His His Arg Ala His Tyr Glu Thr Glu Gly Ser Arg
            435                 440                 445

Gly Ala Val Lys Ala Ser Ala Gly Gly His Pro Ile Val Gln Leu His
450                 455                 460

Gly Tyr Leu Glu Asn Glu Pro Leu Met Leu Gln Leu Phe Ile Gly Thr
465                 470                 475                 480

Ala Asp Asp Arg Leu Leu Arg Pro His Ala Phe Tyr Gln Val His Arg
            485                 490                 495

Ile Thr Gly Lys Thr Val Ser Thr Thr Ser His Glu Ala Ile Leu Ser
                500                 505                 510

Asn Thr Lys Val Leu Glu Ile Pro Leu Leu Pro Glu Asn Ser Met Arg
    515                 520                 525

Ala Val Ile Asp Cys Ala Gly Ile Leu Lys Leu Arg Asn Ser Asp Ile
530                 535                 540

Glu Leu Arg Lys Gly Glu Thr Asp Ile Gly Arg Lys Asn Thr Arg Val
545                 550                 555                 560

Arg Leu Val Phe Arg Val His Val Pro Gln Pro Ser Gly Arg Thr Leu
                565                 570                 575

Ser Leu Gln Val Ala Ser Asn Pro Ile Glu Cys Ser Gln Arg Ser Ala
            580                 585                 590

Gln Glu Leu Pro Leu Val Glu Lys Gln Ser Thr Asp Ser Tyr Pro Val
            595                 600                 605

Val Gly Gly Lys Lys Met Val Leu Ser Gly His Asn Phe Leu Gln Asp
    610                 615                 620

Ser Lys Val Ile Phe Val Glu Lys Ala Pro Asp Gly His His Val Trp
625                 630                 635                 640

Glu Met Glu Ala Lys Thr Asp Arg Asp Leu Cys Lys Pro Asn Ser Leu
                645                 650                 655

Val Val Glu Ile Pro Pro Phe Arg Asn Gln Arg Ile Thr Ser Pro Val
                660                 665                 670

His Val Ser Phe Tyr Val Cys Asn Gly Lys Arg Lys Gly Ser Gln Tyr
            675                 680                 685

Gln Arg Phe Thr Tyr Leu Pro Ala Asn Gly Asn Ala Ile Phe Leu Thr
    690                 695                 700

Val Ser Arg Glu His Glu Arg Val Gly Cys Phe Phe
705                 710                 715
```

```
<210> SEQ ID NO 47
<211> LENGTH: 302
<212> TYPE: PRT
<213> ORGANISM: Drosophila

<400> SEQUENCE: 47

Thr Lys Asn Val Arg Lys Pro Tyr Val Lys Ile Thr Glu Gln Pro
  1               5                  10                  15

Ala Gly Lys Ala Leu Arg Phe Arg Tyr Glu Cys Glu Gly Arg Ser Ala
                 20                  25                  30

Gly Ser Ile Pro Gly Val Asn Ser Thr Pro Glu Asn Lys Thr Tyr Pro
             35                  40                  45

Thr Ile Glu Ile Val Gly Tyr Lys Gly Arg Ala Val Val Val Ser
 50                  55                  60

Cys Val Thr Lys Asp Thr Pro Tyr Arg Pro His Pro His Asn Leu Val
 65                  70                  75                  80

Gly Lys Glu Gly Cys Lys Lys Gly Val Cys Thr Leu Glu Ile Asn Ser
                 85                  90                  95

Glu Thr Met Arg Ala Val Phe Ser Asn Leu Gly Ile Gln Cys Val Lys
                100                 105                 110

Lys Lys Asp Ile Glu Ala Ala Leu Lys Ala Arg Glu Glu Ile Arg Val
            115                 120                 125

Asp Pro Phe Lys Thr Gly Phe Ser His Arg Phe Gln Pro Ser Ser Ile
130                 135                 140

Asp Leu Asn Ser Val Arg Leu Cys Phe Gln Val Phe Met Glu Ser Glu
145                 150                 155                 160

Gln Lys Gly Arg Phe Thr Ser Pro Leu Pro Pro Val Val Ser Glu Pro
                165                 170                 175

Ile Phe Asp Lys Lys Ala Met Ser Asp Leu Val Ile Cys Arg Leu Cys
            180                 185                 190

Ser Cys Ser Ala Thr Val Phe Gly Asn Thr Gln Ile Ile Leu Leu Cys
        195                 200                 205

Glu Lys Val Ala Lys Glu Asp Ile Ser Val Arg Phe Phe Glu Lys
    210                 215                 220

Asn Gly Gln Ser Val Trp Glu Ala Phe Gly Asp Phe Gln His Thr Asp
225                 230                 235                 240

Val His Lys Gln Thr Ala Ile Thr Phe Lys Thr Pro Arg Tyr His Thr
                245                 250                 255

Leu Asp Ile Thr Glu Pro Ala Lys Val Phe Ile Gln Leu Arg Arg Pro
            260                 265                 270

Ser Asp Gly Val Thr Ser Glu Ala Leu Pro Phe Glu Tyr Val Pro Met
        275                 280                 285

Asp Ser Asp Pro Ala His Leu Arg Arg Lys Arg Gln Lys Thr
290                 295                 300

<210> SEQ ID NO 48
<211> LENGTH: 296
<212> TYPE: PRT
<213> ORGANISM: human

<400> SEQUENCE: 48

Met Ala Ser Gly Leu Tyr Asn Pro Tyr Ile Glu Ile Glu Gln Pro
  1               5                  10                  15

Arg Gln Arg Gly Met Arg Phe Arg Tyr Lys Cys Glu Gly Arg Ser Ala
                 20                  25                  30

Gly Ser Ile Pro Gln Glu His Ser Thr Asp Asn Asn Arg Thr Tyr Pro
```

```
                    35                  40                  45
Ser Ile Asn Ile Met Asn Tyr Tyr Gly Arg Gly Lys Val Arg Ile Thr
     50                  55                  60

Leu Val Thr Lys Asn Asp Pro Tyr Lys Pro His Pro His Asp Leu Val
 65                  70                  75                  80

Gly Lys Asp Cys Arg Asp Gly Tyr Tyr Glu Ala Glu Phe Gly Asn Glu
                 85                  90                  95

Arg Arg Pro Leu Phe Phe Gln Asn Leu Gly Ile Arg Cys Val Lys Lys
                100                 105                 110

Lys Glu Val Lys Glu Ala Ile Ile Thr Arg Ile Lys Ala Gly Ile Asn
            115                 120                 125

Pro Phe Asn Val Pro Glu Lys Gln Leu Asn Asp Ile Glu Asp Cys Asp
        130                 135                 140

Leu Asn Val Val Arg Leu Cys Phe Gln Val Phe Leu Pro Asp Glu His
145                 150                 155                 160

Gly Asn Leu Thr Thr Ala Leu Pro Pro Val Val Ser Asn Pro Ile Tyr
                165                 170                 175

Asp Asn Arg Ala Pro Asn Thr Ala Glu Leu Arg Ile Cys Arg Val Asn
            180                 185                 190

Lys Asn Cys Gly Ser Val Arg Gly Gly Asp Glu Ile Phe Leu Leu Cys
        195                 200                 205

Asp Lys Val Gln Lys Asp Asp Ile Glu Val Arg Phe Val Leu Asn Asp
    210                 215                 220

Trp Glu Ala Lys Gly Ile Phe Ser Gln Ala Asp Val His Arg Gln Val
225                 230                 235                 240

Ala Ile Val Phe Lys Thr Pro Pro Tyr Cys Lys Ala Ile Thr Glu Pro
                245                 250                 255

Val Thr Val Lys Met Gln Leu Arg Arg Pro Ser Asp Gln Glu Val Ser
            260                 265                 270

Glu Ser Met Asp Phe Arg Tyr Leu Pro Asp Glu Lys Asp Thr Tyr Gly
        275                 280                 285

Asn Lys Ala Lys Lys Gln Lys Thr
    290                 295

<210> SEQ ID NO 49
<211> LENGTH: 332
<212> TYPE: PRT
<213> ORGANISM: human

<400> SEQUENCE: 49

Ile Pro Leu Ser Thr Asp Gly Pro Tyr Leu Gln Ile Leu Glu Gln Pro
 1               5                  10                  15

Lys Gln Arg Gly Phe Arg Phe Arg Tyr Val Cys Glu Gly Pro Ser His
                 20                  25                  30

Gly Gly Leu Pro Gly Ala Ser Ser Glu Lys Asn Lys Lys Ser Tyr Pro
             35                  40                  45

Gln Val Lys Ile Cys Asn Tyr Val Gly Pro Ala Lys Val Ile Val Gln
         50                  55                  60

Leu Val Thr Asn Gly Lys Asn Ile His Leu His Ala His Ser Leu Val
 65                  70                  75                  80

Gly Lys His Cys Glu Asp Gly Val Cys Thr Val Thr Ala Gly Pro Lys
                 85                  90                  95

Asp Met Val Val Gly Phe Ala Asn Leu Gly Ile Leu His Val Thr Lys
                100                 105                 110
```

```
Lys Lys Val Phe Glu Thr Leu Glu Ala Arg Met Thr Glu Ala Cys Ile
        115                 120                 125
Arg Gly Tyr Asn Pro Gly Leu Leu Val His Ser Asp Leu Ala Tyr Leu
    130                 135                 140
Gln Ala Glu Gly Gly Gly Asp Arg Gln Leu Thr Asp Arg Glu Lys Glu
145                 150                 155                 160
Ile Ile Arg Gln Ala Ala Val Gln Gln Thr Lys Glu Met Asp Leu Ser
                165                 170                 175
Val Val Arg Leu Met Phe Thr Ala Phe Leu Pro Asp Ser Thr Gly Ser
                180                 185                 190
Phe Thr Arg Arg Leu Glu Pro Val Val Ser Asp Ala Ile Tyr Asp Ser
                195                 200                 205
Lys Ala Pro Asn Ala Ser Asn Leu Lys Ile Val Arg Met Asp Arg Thr
    210                 215                 220
Ala Gly Cys Val Thr Gly Gly Glu Glu Ile Tyr Leu Leu Cys Asp Lys
225                 230                 235                 240
Val Gln Lys Asp Asp Ile Gln Ile Arg Phe Tyr Glu Glu Glu Glu Asn
                245                 250                 255
Gly Gly Val Trp Glu Gly Phe Gly Asp Phe Ser Pro Thr Asp Val His
                260                 265                 270
Arg Gln Phe Ala Ile Val Phe Lys Thr Pro Lys Tyr Lys Asp Val Asn
            275                 280                 285
Ile Thr Lys Pro Ala Ser Val Phe Val Gln Leu Arg Arg Lys Ser Asp
        290                 295                 300
Leu Glu Thr Ser Glu Pro Lys Pro Phe Leu Tyr Tyr Pro Glu Ile Lys
305                 310                 315                 320
Asp Lys Glu Glu Val Gln Arg Lys Arg Gln Lys Leu
                325                 330

<210> SEQ ID NO 50
<211> LENGTH: 295
<212> TYPE: PRT
<213> ORGANISM: human

<400> SEQUENCE: 50

Glu Pro Ala Gln Ala Ser Gly Pro Tyr Val Glu Ile Ile Glu Gln Pro
1               5                   10                  15
Lys Gln Arg Gly Met Arg Phe Arg Tyr Lys Cys Glu Gly Arg Ser Ala
                20                  25                  30
Gly Ser Ile Pro Gly Glu Arg Ser Thr Asp Thr Thr Lys Thr His Pro
            35                  40                  45
Thr Ile Lys Ile Asn Gly Tyr Thr Gly Pro Gly Thr Val Arg Ile Ser
        50                  55                  60
Leu Val Thr Lys Asp Pro Pro His Arg Pro His Pro His Glu Leu Val
65                  70                  75                  80
Gly Lys Asp Cys Arg Asp Gly Tyr Tyr Glu Ala Asp Leu Cys Pro Asp
                85                  90                  95
Arg Asp Ser Ile His Ser Phe Gln Asn Leu Gly Ile Gln Cys Val Lys
                100                 105                 110
Lys Arg Asp Leu Glu Gln Ala Ile Ser Gln Arg Ile Gln Thr Asn Asn
            115                 120                 125
Asn Pro Phe His Val Pro Ile Glu Glu Gln Arg Gly Asp Tyr Asp Leu
        130                 135                 140
Asn Ala Val Arg Leu Cys Phe Gln Val Thr Val Arg Asp Pro Ala Gly
145                 150                 155                 160
```

```
Arg Pro Leu Leu Leu Thr Pro Val Leu Ser His Pro Ile Phe Asp Asn
                165                 170                 175

Arg Ala Pro Asn Thr Ala Glu Leu Lys Ile Cys Arg Val Asn Arg Asn
                180                 185                 190

Ser Gly Ser Cys Leu Gly Gly Asp Glu Ile Phe Leu Leu Cys Asp Lys
                195                 200                 205

Val Gln Lys Glu Asp Ile Glu Val Tyr Phe Thr Gly Pro Gly Trp Glu
                210                 215                 220

Ala Arg Gly Ser Phe Ser Gln Ala Asp Val His Arg Gln Val Ala Ile
225                 230                 235                 240

Val Phe Arg Thr Pro Pro Tyr Ala Asp Pro Ser Leu Gln Ala Pro Val
                245                 250                 255

Arg Val Ser Met Gln Leu Arg Arg Pro Ser Asp Arg Glu Leu Ser Glu
                260                 265                 270

Pro Met Glu Phe Gln Tyr Leu Pro Asp Thr Asp Asp Arg His Arg Ile
                275                 280                 285

Glu Glu Lys Arg Lys Arg Thr
                290                 295

<210> SEQ ID NO 51
<211> LENGTH: 293
<212> TYPE: PRT
<213> ORGANISM: human

<400> SEQUENCE: 51

Gln Leu Pro Ser His Ser Gly Pro Tyr Glu Leu Arg Ile Glu Val Gln
  1               5                  10                  15

Pro Lys Ser His His Arg Ala His Tyr Glu Thr Glu Gly Ser Arg Gly
                 20                  25                  30

Ala Val Lys Ala Ser Ala Gly Gly His Pro Ile Val Gln Leu His Gly
                 35                  40                  45

Tyr Leu Glu Asn Glu Pro Leu Met Leu Gln Leu Phe Ile Gly Thr Ala
       50                  55                  60

Asp Asp Arg Leu Leu Arg Pro His Ala Phe Tyr Gln Val His Arg Ile
 65                  70                  75                  80

Thr Gly Lys Thr Val Ser Thr Thr Ser His Glu Ala Ile Leu Ser Asn
                 85                  90                  95

Thr Lys Val Leu Glu Ile Pro Leu Leu Pro Glu Asn Ser Met Arg Ala
                100                 105                 110

Val Ile Asp Cys Ala Gly Ile Leu Lys Leu Arg Asn Ser Asp Ile Glu
                115                 120                 125

Leu Arg Lys Gly Glu Thr Asp Ile Gly Arg Lys Asn Thr Arg Val Arg
       130                 135                 140

Leu Val Phe Arg Val His Val Pro Gln Pro Ser Gly Arg Thr Leu Ser
145                 150                 155                 160

Leu Gln Val Ala Ser Asn Pro Ile Glu Cys Ser Gln Arg Ser Ala Gln
                165                 170                 175

Glu Leu Pro Leu Val Glu Lys Gln Ser Thr Asp Ser Tyr Pro Val Val
                180                 185                 190

Gly Gly Lys Lys Met Val Leu Ser Gly His Asn Phe Leu Gln Asp Ser
                195                 200                 205

Lys Val Ile Phe Val Glu Lys Ala Pro Asp Gly His His Val Trp Glu
                210                 215                 220

Met Glu Ala Lys Thr Asp Arg Asp Leu Cys Lys Pro Asn Ser Leu Val
```

-continued

```
225                 230                 235                 240

Val Glu Ile Pro Pro Phe Arg Asn Gln Arg Ile Thr Ser Pro Val His
                245                 250                 255

Val Ser Phe Tyr Val Cys Asn Gly Lys Arg Lys Arg Ser Gln Tyr Gln
                260                 265                 270

Arg Phe Thr Tyr Leu Pro Ala Asn Gly Asn Ala Ile Phe Leu Thr Val
                275                 280                 285

Ser Arg Glu His Glu
                290

<210> SEQ ID NO 52
<211> LENGTH: 293
<212> TYPE: PRT
<213> ORGANISM: Mouse

<400> SEQUENCE: 52

Pro Leu Ser Asn Gln Ser Gly Ser Tyr Glu Leu Arg Ile Glu Val Gln
  1               5                  10                  15

Pro Lys Pro His His Arg Ala His Tyr Glu Thr Glu Gly Ser Arg Gly
                 20                  25                  30

Ala Val Lys Ala Pro Thr Gly Gly His Pro Val Val Gln Leu His Gly
             35                  40                  45

Tyr Met Glu Asn Lys Pro Leu Gly Leu Gln Ile Phe Ile Gly Thr Ala
         50                  55                  60

Asp Glu Arg Ile Leu Lys Pro His Ala Phe Tyr Gln Val His Arg Ile
 65                  70                  75                  80

Thr Gly Lys Thr Val Thr Thr Thr Ser Tyr Glu Lys Ile Val Gly Asn
                 85                  90                  95

Thr Lys Val Leu Glu Ile Pro Leu Glu Pro Lys Asn Asn Met Arg Ala
                100                 105                 110

Thr Ile Asp Cys Ala Gly Ile Leu Lys Leu Arg Asn Ala Asp Ile Glu
            115                 120                 125

Leu Arg Lys Gly Glu Thr Asp Ile Gly Arg Lys Asn Thr Arg Val Arg
        130                 135                 140

Leu Val Phe Arg Val His Val Pro Glu Pro Ser Gly Arg Ile Val Ser
145                 150                 155                 160

Leu Gln Ala Ala Ser Asn Pro Ile Glu Cys Ser Gln Arg Ser Ala His
                165                 170                 175

Glu Leu Pro Met Val Glu Arg Gln Asp Met Asp Ser Cys Leu Val Tyr
                180                 185                 190

Gly Gly Gln Gln Met Ile Leu Thr Gly Gln Asn Phe Thr Ala Glu Ser
            195                 200                 205

Lys Val Val Phe Met Glu Lys Thr Thr Asp Gly Gln Gln Ile Trp Glu
        210                 215                 220

Met Glu Ala Thr Val Asp Lys Asp Lys Ser Gln Pro Asn Met Leu Phe
225                 230                 235                 240

Val Glu Ile Pro Glu Tyr Arg Asn Lys His Ile Arg Val Pro Val Lys
                245                 250                 255

Val Asn Phe Tyr Val Ile Asn Gly Lys Arg Lys Arg Ser Gln Pro Gln
                260                 265                 270

His Phe Thr Tyr His Pro Val Pro Ala Ile Lys Thr Glu Pro Ser Asp
                275                 280                 285

Glu Tyr Glu Pro Ser
                290
```

<210> SEQ ID NO 53
<211> LENGTH: 11
<212> TYPE: DNA
<213> ORGANISM: Unknown
<220> FEATURE:
<223> OTHER INFORMATION: Description of Unknown Organism: enhancer
      capable of binding to an NF-AT complex

<400> SEQUENCE: 53
aagaggaaaa a                                                             11

<210> SEQ ID NO 54
<211> LENGTH: 20
<212> TYPE: DNA
<213> ORGANISM: Unknown
<220> FEATURE:
<223> OTHER INFORMATION: Description of Unknown Organism: putative NF-AT
      binding site

<400> SEQUENCE: 54
gaaaggagga aaaactgttt                                                    20

<210> SEQ ID NO 55
<211> LENGTH: 20
<212> TYPE: DNA
<213> ORGANISM: Unknown
<220> FEATURE:
<223> OTHER INFORMATION: Description of Unknown Organism: putative NF-AT
      binding site

<400> SEQUENCE: 55
ccaaagagga aaatttgttt                                                    20

<210> SEQ ID NO 56
<211> LENGTH: 20
<212> TYPE: DNA
<213> ORGANISM: Unknown
<220> FEATURE:
<223> OTHER INFORMATION: Description of Unknown Organism: putative NF-AT
      binding site

<400> SEQUENCE: 56
cagaagagga aaatgaagg                                                     20

<210> SEQ ID NO 57
<211> LENGTH: 20
<212> TYPE: DNA
<213> ORGANISM: Unknown
<220> FEATURE:
<223> OTHER INFORMATION: Description of Unknown Organism: putative NF-AT
      binding site

<400> SEQUENCE: 57
tccaggagaa aaaatgcctc                                                    20

<210> SEQ ID NO 58
<211> LENGTH: 20
<212> TYPE: DNA
<213> ORGANISM: Unknown
<220> FEATURE:
<223> OTHER INFORMATION: Description of Unknown Organism: putative NF-AT
      binding site
<221> NAME/KEY: modified_base
<222> LOCATION: (9)
<223> OTHER INFORMATION: i

<400> SEQUENCE: 58

```
aaaacttgng aaaatacgta                                               20

<210> SEQ ID NO 59
<211> LENGTH: 20
<212> TYPE: DNA
<213> ORGANISM: Unknown
<220> FEATURE:
<223> OTHER INFORMATION: Description of Unknown Organism: putative NF-AT
      binding site

<400> SEQUENCE: 59
taaaggagag aacaccagct                                               20

<210> SEQ ID NO 60
<211> LENGTH: 20
<212> TYPE: DNA
<213> ORGANISM: Unknown
<220> FEATURE:
<223> OTHER INFORMATION: Description of Unknown Organism: putative NF-AT
      binding site

<400> SEQUENCE: 60
gcagggtggg aaaggccttt                                               20

<210> SEQ ID NO 61
<211> LENGTH: 29
<212> TYPE: DNA
<213> ORGANISM: Unknown
<220> FEATURE:
<223> OTHER INFORMATION: Description of Unknown Organism: end-labled
      binding site for NF-AT

<400> SEQUENCE: 61
ggaggaaaaa ctgttcatac agaaggggt                                     29

<210> SEQ ID NO 62
<211> LENGTH: 31
<212> TYPE: DNA
<213> ORGANISM: Unknown
<220> FEATURE:
<223> OTHER INFORMATION: Description of Unknown Organism: mutant NF-AT
      probe

<400> SEQUENCE: 62
aagaaaggag taaaaaattt ttaatacaga a                                  31
```

NF-AT POLYPEPTIDES AND POLYNUCLEOTIDES AND SCREENING METHODS FOR IMMUNOSUPPRESSIVE AGENTS

CROSS-REFERENCE TO RELATED APPLICATIONS

This application is continuation-in-part of application Ser. No. 08/507,032, entitled "Screening methods for Immunosuppressive Agents", filed on Jul. 31, 1995, U.S. Pat. No. 5,989,810, which is a file-wrapper-continuation of application Ser. No. 08/228,944, filed on Apr. 18, 1994, now abandoned, which is a file-wrapper-continuation of application Ser. No. 07/749,385, filed on Aug. 22, 1991 now abandoned; and a continuation-in-part of application Ser. No. 08/260,174, entitled "NF-A T-Polypeptides and Polynucleotides", filed Jun. 13, 1994, U.S. Pat. No. 6,197,925 which is a continuation-in-part of application Ser. No. 08/124,981, entitled "NF-AT Polypeptides and Polynucleotides", filed Sep. 20, 1993 (U.S. Pat. No. 5,837,840). These applications are hereby incorporated by reference herein.

STATEMENT OF RIGHTS

This invention was made in the course of work supported by the U.S. Government. The U.S. Government has therefore certain rights in this invention.

Field of the Invention

The invention provides novel polypeptides which are associated with the transcription complex NF-AT, polynucleotides encoding such polypeptides, antibodies which are reactive with such polypeptides, polynucleotide hybridization probes and PCR amplification probes for detecting polynucleotides which encode such polypeptides, transgenes which encode such polypeptides, homologous targeting constructs that encode such polypeptides and/or homologously integrate in or near endogenous genes encoding such polypeptides, nonhuman transgenic animals which comprise functionally disrupted endogenous genes that normally encode such polypeptides, and transgenic nonhuman animals which comprise transgenes encoding such polypeptides. The invention also provides methods for detecting T cells (including activated T cells) in a cellular sample, methods for treating hyperactive or hypoactive T cell conditions, methods for screening for immunomodulatory agents, methods for diagnostic staging of lymphocyte differentiation, methods for producing NF-AT proteins for use as research or diagnostic reagents, methods for producing antibodies reactive with the novel polypeptides, and methods for producing transgenic nonhuman animals.

BACKGROUND OF THE INVENTION

The immune response is coordinated by the actions of cytokines produced from activated T lymphocytes, such as lymphocytes contacted with antigens. Cytokines are responsible for the control of proliferation and cell fate decisions among precursors of B cells, granulocytes and macrophages. T lymphocytes having a broad spectrum of antigen receptors are produced in the thymus as a product of the processes of selection and differentiation. When these T cells migrate to the peripheral lymphoid organs and encounter antigen, they undergo activation, during the process of which they produce large numbers of cytokines that act upon other cells of the immune system to coordinate their behavior to bring about an effective immune response.

T lymphocyte activation involves the specific regulation of many genes from minutes after the antigen encounter until at least 10 days later. T cells may also be activated by stimuli such as the combination of a calcium ionophore (e.g., ionomycin) and an activator of protein kinase C, such as phorbol myristate acetate (PMA). Several lectins, including phytohemagglutinin (PHA) may also be used to activate T cells (Nowell, P. C. (1990) *Cancer Res.* 20:462–466). The T cell activation genes are roughly grouped based on the time after stimulation at which each gene is regulated. Early genes trigger the regulation of subsequent genes in the activation pathway.

Because of the critical role of the T lymphocyte, agents that interfere with the early activation genes, such as cyclosporin A and FK506, are effective immunosuppressants. These early activation genes are regulated by transcription factors, such as NF-AT, that in turn are regulated through interactions with the antigen receptor. These transcription factors act through enhancer and promoter elements on the early activation genes to modulate their rate of transcription.

A typical early gene enhancer element is located in the first 325 base pairs upstream of the start site of the interleukin-2 gene. This region has been used extensively to dissect the requirements for T lymphocyte activation. This region binds an array of transcription factors including NF-AT, NFkB, Ap-1, Oct-1, and a newly identified protein that associates with Oct-1 called OAP-40. These different transcription factors act together to integrate the complex requirements for T lymphocyte activation.

The interieukin-2 gene is essential for both the proliferation and immunologic activation of T cells. The signaling pathways which connect the IL-2 gene and a representative and important early gene with the antigen receptor on the T cell surface and the signal transmission pathways between them are illustrated in FIG. 1. The binding site for the NF-AT protein appears to restrict expression of the interleukin-2 gene and other early activation genes to the context of an activated T lymphocyte. This information is based upon past work by Durand et al., *Mol. and Cell. Biol.* (1988), Shaw et al., *Science,* 241: 202 (1988), and Verwiej et al., (1990) *J. Biol. Chem,* 265: 15788–15795 (1990).

NF-AT appears to be the most important element among the group mentioned above in that it is able to direct transcription of any genes to activated T cells in the context of an intact transgenic animal (Verweij et al. *J. Biol. Chem.* 265:15788–15795, 1990). NF-AT is also the only element that requires physiologic activation through the antigen receptor for the activation of transcription by NF-AT. For example, the element is activated only after proper presentation of antigen of exactly the correct sequence by MHC-matched antigen presenting cells. This effect can be mimicked by pharmacologic agents, including the combination of ionomycin and PMA, which can also activate T cells through critical early genes.

Other elements within the IL-2 enhancer, for example, the NF-KB site or the AP-1 site, activate transcription in response to less specific stimuli, such as tumor necrosis factor alpha or simply PMA by itself These compounds do not activate the IL-2 gene and other early activation genes and do not lead to T cell activation. Such observations have led to the conclusion that NF-AT restricts the expression of certain early genes, such as the interleukin-2 gene to their proper biologic context. Preliminary data have also indicated that a selective genetic deficiency of NF-AT produces severe combined immunodeficiency (SCID) (Chatilla, T. et al. *New Engl. J Med.* 320:696–702, 1989).

As noted above, cyclosporin A (CsA) and FK506 are capable of acting as immunosuppressants. These agents inhibit T and B cell activation, mast cell degranulation and other processes essential to an effective immune response (Borel et al. (1976) *Agents Actions* 6: 468; Sung et al. (1988) *J. Exp. Med.* 168: 1539; Gao et al. *Nature* 336: 176). In T lymphocytes, these drugs disrupt an unknown step in the transmission of signals from the T cell antigen receptor to cytokine genes that coordinate the immune response (Crabtree et al. (1989) *Science* 243: 355; Schreiber et al. (1989) *Science* 251:283; Hohman & Hutlsch (1990) *New Biol.* 2: 663).

Putative intracellular receptors for FK506 and CsA have been described and found to be cis-trans prolyl isomerases (Fischer & Bang (1985) *Biochim. Biophys. Acta* 828: 39; Fischer et al. *Nature* 337: 476; Handschumacher et al. (1984) *Science* 226: 544; Lang & Schmid (1988) *Nature* 331: 453; Standaert et al. (1990) *Nature* 346: 671). Binding of the drugs inhibits isomerase activity; however, studies with other prolyl isomerase inhibitors (Bierer et al. (1990) *Science* 250: 556) and analysis of cyclosporin-resistant mutants in yeast suggest that the prevention of T lymphocyte activation results from formation of an inhibitory complex involving the drug and the isomerase (Bierer et al. (1990) *Proc. Natl. Acad. Sci. U.S.A.* 87: 9231; Tropschug et al. (1989) *Nature* 342: 953), and not from inhibition of the isomerase activity per se.

The transcription factor NF-AT appears to be a specific target of cyclosporin A and FK506, since transcription directed by this protein is completely blocked in T cells treated with these drugs, with little or no effect on other transcription factors, such as AP-1 and NF-$_K$B (Shaw et al.(1988) *op. cit*; Emmel et al. (1989) *Science* 246: 1617; Mattila et al. (1990) *EMBO J.* 9: 4425). However, the drugs' actual mechanism of action remains unclear. Unfortunately, while both are potent immunosuppressive agents, neither cyclosporin nor FK506 are ideal drugs.

For example, cyclosporin adverse reactions include renal dysfunction, tremors, nausea and hypertension. Indeed, for many years researchers have attempted to develop superior replacements, with FK506 being the most recent candidate. Without understanding how cyclosporin (or FK506) functions at the intracellular level, developing improved immunosuppressants represents an extremely difficult research effort with a very limited likelihood of success.

Thus, there exists a significant need to understand the functional basis of cyclosporin and FK506 effectiveness. With such knowledge, improved assays for screening drug candidates would become feasible, which could in turn dramatically enhance the search process. The present invention fulfills these and other needs.

SUMMARY OF THE INVENTION

The present invention provides novel methods and compositions useful, e.g., in screening for immunosuppressive agents. The invention is based in part on the discovery of the overall mechanism by which NF-AT is formed intracellularly from nuclear and cytoplasmic subunits and on the isolation of nucleic acids encoding NF-AT proteins.

A basis of the present invention is the discovery that NF-AT (i.e., a complex comprising NF-AT$_c$ and NF-AT$_n$) is formed when a signal from the antigen receptor induces a preexisting cytoplasmic NF-AT submit (NF-AT$_c$) to translocate to the nucleus and combine with a nuclear NF-AT subunit (NF-AT$_n$). Cyclosporin A and FK506 block translocation of the cytoplasmic component without affecting the nuclear subunit. A plausible synthesis of these studies and previous work posits that the prolyl isomerases, FK506-binding protein (FK-BP) and cyclophilin, also function to import proteins to the nucleus.

The invention is also based on the purification of two related proteins, NF-ATc and NF-ATp, encoded by separate genes that represent the preexisting or cytosolic components of NF-AT. The carboxy-terminal half of NF-AT$_c$ shows limited similarity to the DNA binding and dimerization regions of the Dorsal/Rel family of transcription factors (FIG. 15, for review, Nolan and Baltimore (1992) *Current Biology, Ltd.* 2: 211–220) however, NF-AT$_c$ appears to be the most distantly related member of the group. Expression of a full length cDNA for one of these proteins, NF-AT$_c$, activates the IL-2 promoter in non-T lymphocytes, while a dominant negative of NF-AT$_c$ specifically blocks activation of the IL-2 promoter in T lymphocytes, indicating that NF-AT$_c$ is required for IL-2 gene expression and is responsible for the restricted expression of IL-2. NF-AT$_c$ RNA expression is largely restricted to lymphoid tissues and is induced upon cell activation. The second protein, NF-AT$_p$, is highly homologous to NF-AT$_c$ over a limited domain, but exhibits wider tissue distribution and is highly expressed in tissues characterized by Ca++-dependent regulation. Together these proteins are members of a new family of DNA binding proteins, which are distantly related to the Dorsal/Rel family (Nolan and Baltimore (1992) *Current Biology, Ltd.* 2: 211–220). Agents that increase intracellular Ca++ or that activate protein kinase C independently produce alterations in the mobility of NF-AT$_c$, indicating that distinct signaling pathways converge on NF-AT$_c$ to regulate its function.

In accordance with one aspect of the invention, novel compositions include NF-ATc polypeptides, nuclear components of NF-AT complexes, e.g, an NF-AT$_n$ polypeptide, mixtures of the polypeptides, and cellular extracts containing the polypeptides. The NF-AT$_n$ and NF-AT$_c$ subunits are capable of forming a native NF-AT complex which binds in a sequence-specific manner to a transcriptional regulatory DNA sequence of an immune response gene. The NF-AT$_n$ subunit is characterized by:

i. a molecular weight of about 45 kd;
  ii. inducible expression in T cells (such as Jurkat cells);
  iii. inducible expression in HeLa cells by exposing the cells to an agent (such as PMA) capable of activating protein kinase C;
  iv. a lack of effect by cyclosporin and FK506 on NF-AT$_n$ synthesis in T cells; and
  v. specifically binding to an NF-AT$_c$.

The NF-AT$_c$ subunit is characterized by:

i. a molecular weight of about 90 kd;
  ii. constitutively expressed in T cells;
  iii. ability to be transported into a nucleus after a Ca++ flux in the cell;
  iv. nuclear transport inhibited by cyclosporin and FK506; and
  v. specifically binding to an NF-AT$_n$.

In another aspect of the present invention, isolated or purified nucleic acid sequences (or their complementary sequences) are provided which are capable of binding to an NFAT complex, wherein the sequences are substantially homologous to an enhancer, such as IL-2 and IL-4 enhancers, particularly the sequence AAGAGGAAAAA (SEQ ID NO: 53).

In another aspect, the invention embraces methods of screening for an immune regulating agent comprising combining the agent with a component selected from the group consisting of an NF-AT$_n$ polypeptide, an NF-AT$_c$ polypeptide, and mixtures thereof; and determining whether the agent binds to the selected component.

In another embodiment, candidate immunomodulatory agents are identified by their ability to block the binding of a NF-AT$_c$ polypeptide to other components of NF-AT (e.g., AP-1) and/or to block the binding of NF-AT to DNA having an NF-AT recognition site. The DNA preferably includes one or more NF-AT binding sites at which a NF-AT protein complex specifically binds. One means for detecting binding of a NF-AT protein comprising NF-AT$_c$ to DNA is to immobilize the DNA, such as by covalent or noncovalent chemical linkage to a solid support, and to contact the immobilized DNA with a NF-AT protein complex comprising a NF-AT$_c$ polypeptide that has been labeled with a detectable marker (e.g., by incorporation of radiolabeled amino acid). Such contacting is typically performed in aqueous conditions which permit binding of a NF-AT protein to a target DNA containing a NF-AT binding sequence. Binding of the labeled NF-AT to the immobilized DNA is measured by determining the extent to which the labeled NF-AT$_c$ polypeptide is immobilized as a result of a specific binding interaction. Such specific binding may be reversible, or may be optionally irreversible if a cross-linking agent is added in appropriate experimental conditions.

In yet another embodiment, methods of screening for an immune regulating agent will comprise the steps of:
  i. preparing a collection of eukaroytic cells containing NF-AT$_c$ in the cytoplasm of the cell;
  ii. treating the cells with an agent;
  iii. assaying for nuclear translocation of the NF-AT$_c$ wherein blocking of nuclear transport correlates with the immunosuppressive activity of the agent. The step of assaying for nuclear translocation preferably comprises determining the nuclear presence of the NF-AT$_c$ which is labeled with a detectable marker. Alternatively, the step of assaying for nuclear translocation comprises determining nuclear association between the NF-AT$_c$ and an NF-AT$_n$, preferably using nuclei treated previously with the agent.

The assaying step can also comprise determining binding of NF-AT to a DNA sequence in the cell, such as by determining mRNA transcription levels in the cell, wherein the mRNA encodes an immune response gene.

In a different embodiment, the method of screening for immune regulating agents can comprise:
  i. constructing a chimeric gene comprising an NF-AT regulated enhancer region linked to a reporter gene (e.g., chloramphenicol acetyltransferase (CAT) gene);
  ii. inserting the chimeric gene into T cells;
  iii. treating the T cells with T cell activating compounds in the presence or absence of the agent; and
  iv. determining the effect of the agent on expression of the reporter gene. Inhibition of expression of the reporter gene indicates that the agent is a candidate immunosuppressant agent.

In one aspect, candidate immunomodulatory agents are identified as being agents capable of inhibiting (or enhancing) intermolecular binding between NF-AT$_c$ and other polypeptides which comprises a NF-AT complex (e.g., AP-1, JunB, etc.). The invention provides methods and compositions for screening libraires of agents for the capacity to interfere with binding of NF-AT$_c$ to other NF-AT polypeptide species under aqueous binding conditions. Typically, at least either NF-AT$_c$ and/or another NF-AT polypeptide species is labeled with a detectable label and intermolecular binding between NF-AT$_c$ and other NF-AT polypeptide species is detected by the amount of labeled species captured in NF-AT complexes and the like.

For example, methods of assaying for a candidate-immunosuppressant agent comprise mixing the agent with NF-AT$_n$ and NF-AT$_c$ under conditions which permit specific multimerization to form NF-AT, comprising dimerization of NF-AT$_n$ and NF-AT$_c$, and determining whether said dimerization (and/or multimerization with other subunits) occurs. Typically, NF-AT$_n$ or NF-AT$_c$ is immobilized and at least one subunit is labeled with a detectable marker, most usually the non-immobilized NF-AT subunit is labeled.

The present invention further provides several novel methods and compositions for modulating the immune response and for screening for modulators of the immune response which utilize polynucleotide sequences encoding NF-AT$_c$ recombinant proteins and complementary polynucleotides which are substantially identical to NF-AT$_c$ polynucleotide sequences.

Thus, in another aspect of the invention, NF-AT$_c$ polypeptides comprising polypeptide sequences which are substantially identical to a sequence shown in FIG. 12 or a cognate NF-AT$_c$ amino acid sequence are provided.

The invention also provides for nucleic acid sequences encoding NF-AT$_c$. The characteristics of the cloned sequences are given, including the nucleotide and predicted amino acid sequence in FIG. 12. Polynucleotides comprising these sequences can serve as templates for the recombinant expression of quantities of NF-AT$_c$ polypeptides, such as human NF-AT$_c$ and murine NF-AT$_c$. Polynucleotides comprising these sequences can also serve as probes for nucleic acid hybridization to detect the transcription and mRNA abundance of NF-AT$_c$ mRNA in individual lymphocytes (or other cell types) by in situ hybridization, and in specific lymphocyte populations by Northern blot analysis and/or by in situ hybridization (Alwine et al. (1977) *Proc. Natl. Acad. Sci. U.S.A.* 74: 5350) and/or PCR amplification and/or LCR detection. Such recombinant polypeptides and nucleic acid hybridization probes have utility for in vitro screening methods for immunomodulatory agents and for diagnosis and treatment of pathological conditions and genetic diseases, such as transplant rejection reactions, T cell-mediated immune responses, lymphocytic leukemias (e.g., T cell leukemia or lymphoma) wherein NF-AT activity contributes to disease processes, autoimmune disease, arthritis, and the like.

The invention also provides antisense polynucleotides complementary to NF-AT$_c$ sequences which are employed to inhibit transcription and/or translation of the cognate mRNA species and thereby effect a reduction in the amount of the respective NF-AT$_c$ protein in a cell (e.g., a T lymphocyte of a patient). Such antisense polynucleotides can function as immunomodulatory drugs by inhibiting the formation of NF-AT protein required for T cell activation.

In a variation of the invention, polynucleotides of the invention are employed for diagnosis of pathological conditions or genetic disease that involve T cell neoplasms or T cell hyperfunction or hypofunction, and more specifically conditions and diseases that involve alterations in the structure or abundance of NF-AT$_c$ polypeptide, NF-AT$_c$ polynucleotide sequence, or structure of the NF-AT$_c$ gene or flanking region(s).

The invention also provides antibodies which bind to NF-AT$_c$ with an affinity of about at least $1 \times 10^7$ M$^{-1}$ and which lack specific high affinity binding for other proteins present in activated T cells. Such antibodies can be used as diagnostic reagents to identify T cells (e.g., activatable T cells) in a cellular sample from a patient (e.g., a lymphocyte sample, a solid tissue biopsy) as being cells which contain an increased amount of NF-$AT_c$ protein determined by standardization of the assay to be diagnostic for activated T cells. Frequently, anti-NF-$AT_c$ c antibodies are included as diagnostic reagents for immunohistopathology staining of cellular samples in situ. Additionally, anti-NF-$AT_c$ antibodies may be used therapeutically by targeted delivery to T cells (e.g., by cationization or by liposome/immunoliposome delivery).

The invention also provides NF-$AT_c$ polynucleotide probes for diagnosis of neoplasia or immune status by detection of NF-$AT_c$ mRNA in cells explanted from a patient, or detection of a pathognomonic NF-$AT_c$ allele (e.g., by RFLP or allele-specific PCR analysis). A pathognomonic NF-$AT_c$ allele is an allele which is statistically correlated with the presence of a predetermined disease or propensity to develop a disease. Typically, the detection will be by in situ hybridization using a labeled (e.g., $^{32}P$, $^{35}S$, $^{14}C$, $^{3}H$, fluorescent, biotinylated, digoxigeninylated) NF-$AT_c$ polynucleotide, although Northern blotting, dot blotting, or solution hybridization on bulk RNA or poly $A^+$ RNA isolated from a cell sample may be used, as may PCR amplification using NF-$AT_c$-specific primers. Cells which contain an increased amount of NF-$AT_c$ mRNA as compared to standard control values for cells or cell types other than activated T cells or activatable T cells will be thereby identified as activated T cells or activatable T cells. Similarly, the detection of pathognomonic rearrangements or amplification of the NF-$AT_c$ locus or closely linked loci in a cell sample will identify the presence of a pathological condition or a predisposition to developing a pathological condition (e.g., cancer, genetic disease).

The present invention also provides a method for diagnosing T cell hypofunction or hyperfunction in a human patient, wherein a diagnostic assay (e.g., immunohistochemical staining of fixed lymphocytic cells by an antibody that specifically binds human NF-$AT_c$) is used to determine if a predetermined pathognomonic concentration of NF-$AT_c$ protein or NF-$AT_c$ mRNA is present in a biological sample from a human patient; if the assay indicates the presence of NF-$AT_c$ protein or NF-$AT_c$ mRNA at or above such predetermined pathognomonic concentration, the patient is diagnosed as having T cell hyperfunction or hypofunction condition, or transplant rejection and the like.

All publications and patent applications herein are incorporated by reference to the same extent as if each individual publication or patent application was specifically and individually indicated to be incorporated by reference.

Figure 1:
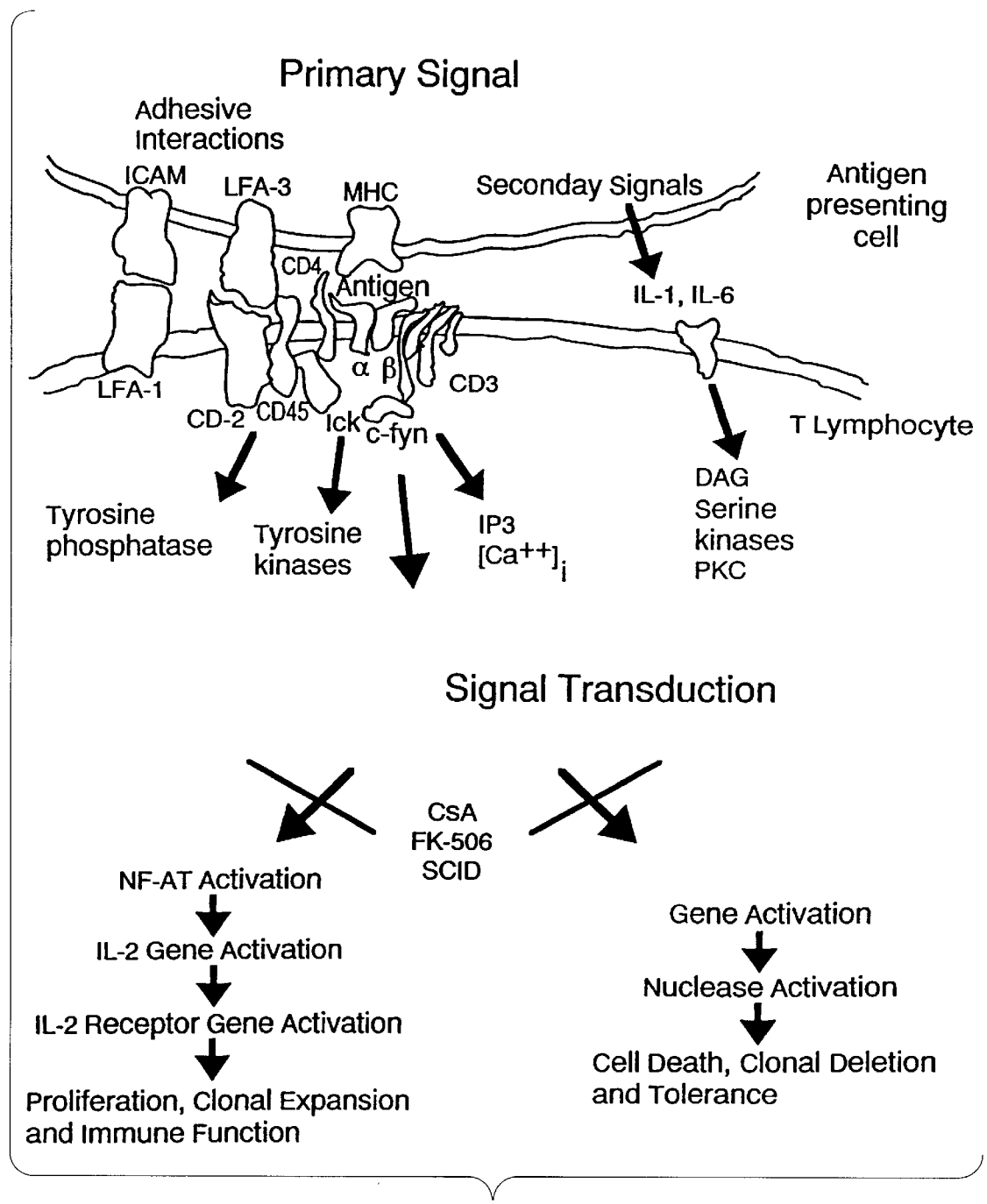
FIG. 1. Representation of the signal transmission pathways carrying information from the T lymphocyte antigen receptor to the early activation genes that lead to proliferation, clonal expansion and immune function or to cell death (apoptosis), clonal deletion and tolerance. Primary signals emanate from the interaction of the T cell antigen receptor (includes the TCR and CD3 complex) with antigen bound by the major histocompatibility complex (MHC). Accessory signaling molecules such as CD2, CD4, and LFA-1 augment the primary signal. A secondary signal that is required to completely activate T lymphocytes is provided by interleukins 1 and 6. These initial signals are transmitted to the nucleus by second messengers such as tyrosine phosphatases (CD-45), tyrosine kinases (lck and fyn), as well as by protein kinase C (PKC) and intracellular calcium. As depicted in the schematic, immunosuppressive drugs such as FK506 and cyclosporin (CsA) as well as immune deficiency diseases (SCID) interfere with the proper transmission of signals from the TCR to the nucleus.

90.1 cells. In lanes 4–5 and 7–8, NF-AT is reconstituted by mixing nuclear extracts (5 μg) from stimulated/FK506-treated Jurkat or JK12/90.1 cells with cytoplasmic extracts (5 μg) from nonstimulated Jurkat or JK12/90.1 cells. (d) In lanes 1–3, nuclear extracts (5 μg) from nonstimulated (ns), stimulated (s), and stimulated/cyclosporin A-treated (s+C) cells. Stimulated/cyclosporin A-treated (s+C) nuclear extracts (5 μg) were complemented with cytoplasmic fractions (5 μg) from: lane 4, nonstimulated (ns); lane 5, stimulated (s); and lane 6, stimulated/cyclosporin A-treated (s+C) cells.

FIG. 7. The nuclear component of NF-AT is present in HeLa cells and can be complemented by Jurkat cytoplasm, but not by HeLa cell cytoplasm, to reconstitute NF-AT binding activity. (a) Lanes 1–6, gel mobility shift assay using HeLa nuclear (10 μg) and cytoplasmic (10 μg) extracts from nonstimulated (ns), stimulated (s), and stimulated/FK506-treated (s+F) cells do not form a NF-AT protein-DNA complex. In lanes 7–9, homologous mixing of nuclear extracts (5 μg) from stimulated/FK506-treated (s+F) HeLa cells with HeLa cytoplasmic extracts (5 μg) does not reconstitute NF-AT. (b) NF-AT binding activity is reconstituted with HeLa nuclear and Jurkat cytoplasmic extracts. Nuclear extracts (5 μg) from stimulated/FK506treated HeLa cells complemented by cytoplasmic extracts (5 μg) from: lane 1, nonstimulated (ns); and lane 3, stimulated/FK506-treated (s+F) Jurkat cells. In lanes 4–9, reconstituted NF-AT binding complex demonstrates DNA binding specificity when competed by 10 μg of unlabelled NF-AT or mutant NF-AT oligonucleotides. (c) Lanes 1–3, heterologous mixing of Jurkat nuclear extracts (5 μg) from stimulated/FK506treated (s+F) with HeLa -cytoplasmic extracts (5 ug) does not reconstitute NF-AT binding activity.

Figure 8:
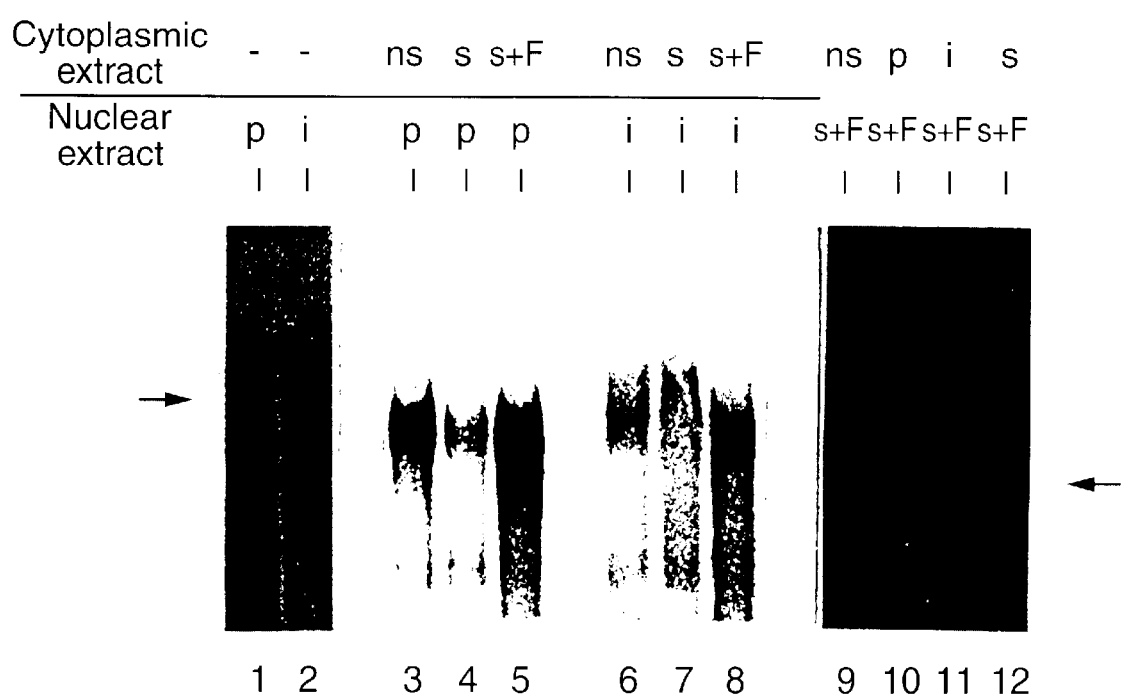

FIG. 8. The nuclear component of NF-AT is induced by PMA while calcium mediated signals allow translocation of the preexisting cytoplasmic subunit of NF-AT. (a) Lanes 1 and 2, gel mobility shift assay using nuclear extracts (10 μg) from PMAstimulated (p) and ionomycin-stimulated (i) cells. In lanes 3–8, complementation of nuclear extracts (5 μg) from PMAstimulated and ionomycin-stimulated cells with cytoplasmic extracts (5 μg) from nonstimulated (ns), stimulated (s), and stimulated/FK506-treated (s+F) cells. Stimulated/FK506-treated (s+F) nuclear extracts (5 μg) were complemented with cytoplasmic extracts (5 μg) from: lane 9, nonstimulated (ns); lane 10, PMA-stimulated (p); lane 11, ionomycin-stimulated (i); and lane 12, stimulated (s) cells. Arrows indicate the NF-AT protein DNA binding complex.

FIG. 9. In vitro transcription directed by the IL-2 enhancer or three tandemly linked NF-AT binding sites in nuclear extracts stimulated under different conditions. (a) IL-2 directed transcription: lane 1, nonstimulated; lane 2, PMA/ionomycin/FK506-treated cells; and PMA/ionomycin stimulated cells, lane 3. NF-AT directed transcription: lane 4,cdescriptionde nonstimulated; lane 5, PMA/ionomycin/FK506treated cells; lane 6, PMA/ionomycin-stimulated cells. Expression from the IL-2 enhancer and NF-AT G-less template generates a 401 and 383 nucleotide (nt) transcript, respectively. The adenovirus major late promoter (AdMLP) internal control generates a 280 nt transcript. Fold induction is calculated following normalization to AdMLP transcription. (b) Ribonuclease protection assay of NF-AT driven lac Z mRNA. Lane 1, nonstimulated; lane 2, PMA/ionomycin-stimulated; lane 3, PMA/ionomycin/FK506-treated FIG. 10. NF-AT dependent T-antigen transcription levels in tissues of transgenic mice. Total RNA was prepared from tissues of a 6-week-old mouse of line Tag8 (Verweij et al. JBC 5 265:15788–15795 (1990)). Spleen, thymus and bone marrow cells were cultured for 24 hours in the presence of ionomycin (0.6 μM1 and PMA (10 μg/ml). Ten micrograms of each RNA sample was used in an RNase protection assay. As a probe we used the 176 nucleotide P-32 labeled antisense NF-AT-Tag RNA probe. Correctly initiated mRNA would yield a 47-nucleotide protected fragment. The position of the fragment (TI) is indicated by an arrow.

Figure 11:
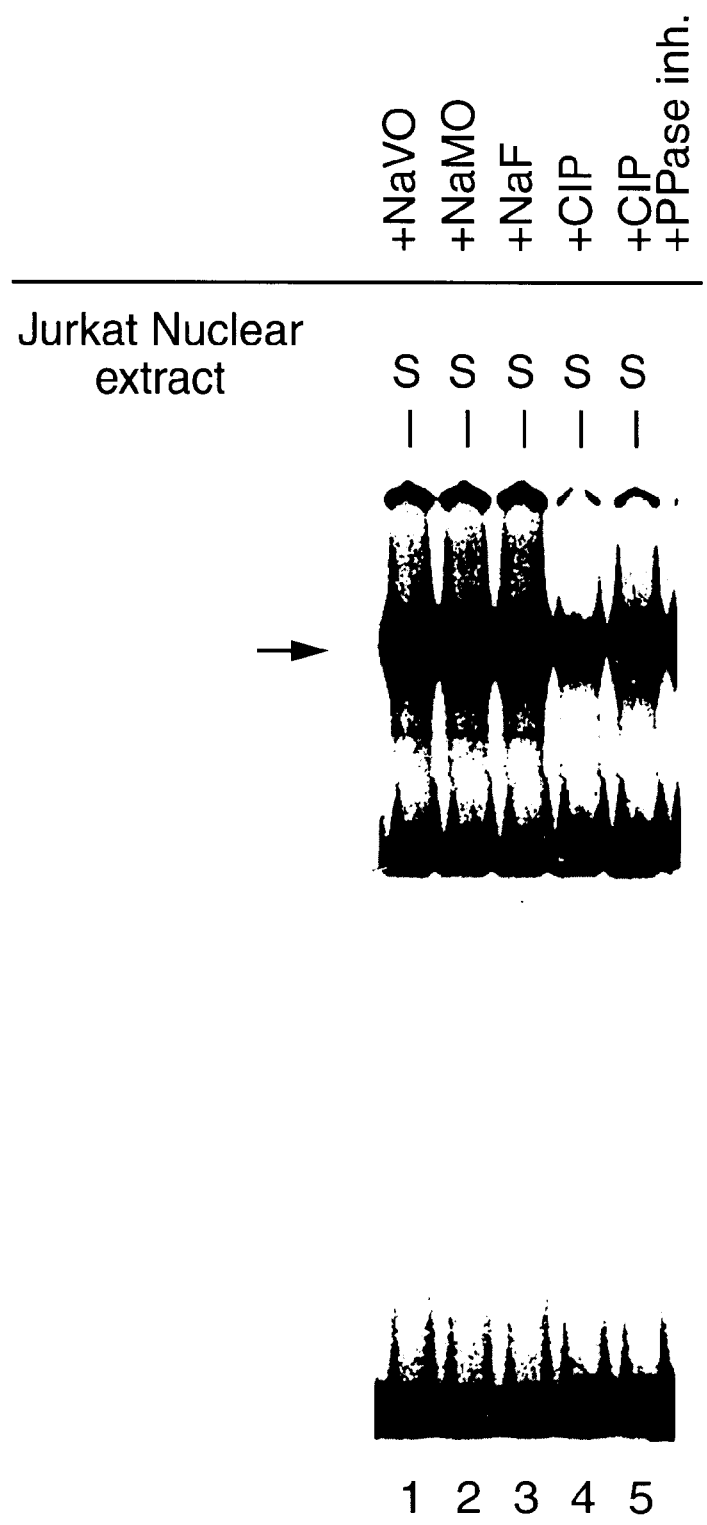

FIG. 11. Dephosphorylation of NF-AT inhibits its DNA binding. Lanes 1–5, gel mobility shift assay. Nuclear extracts (10 μg) from PMA/ionomycin stimulated Jurkat cells were incubated with several protein phosphatase inhibitors in the presence or absence of calf intestinal phosphatase. Characteristic NF-AT mobility shift in the presence of: lane 1, 200 μm sodium vanadate ($Na_2VO_4$); lane 2, 200 mM sodium molybdate ($Na_2MO_4$); lane 3, 10 mM sodium fluoride (NaF); lane 4, one unit of calf intestinal phosphatase (CIP); lane 5, one unit of calf intestinal phosphatase plus 200 μM of sodium vanadate, 200 μM sodium molybdate and 10 mm sodium fluoride. For methods see FIG. 6. The arrow indicates the NF-AT protein DNA complex.

FIG. 12 Panels A-G (SEQ ID NOs: 45–46) shows the nucleotide sequence of the human $NF-AT_c$ cDNA and the deduced amino acid sequence. N indicates that a sequence ambiguity is present.

Figure 13:
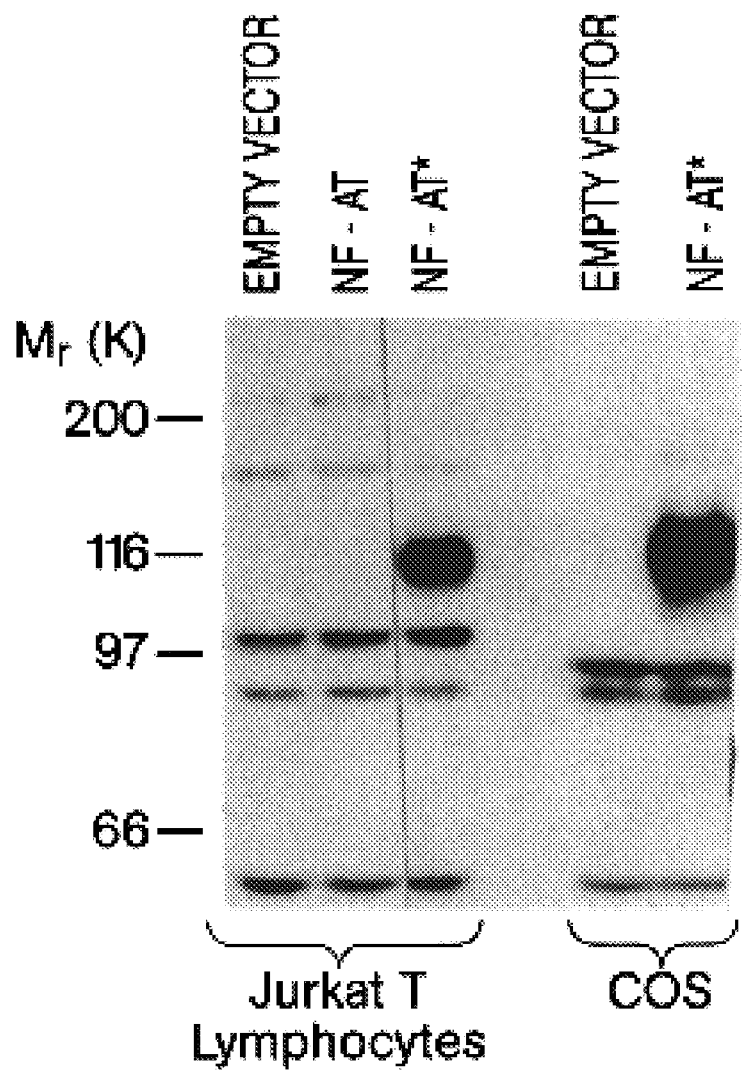

FIG. 13 shows the expression of $NF-AT_c$ protein in T cells (Jurkat) and non-T cells (Cos).

FIG. 14 Panels A and B show that the $NF-AT_c$ cDNA clone encodes a protein that activates transcription from an NF-AT site and is capable of activating the IL-2 promoter in non-T cells.

Figure 15B:
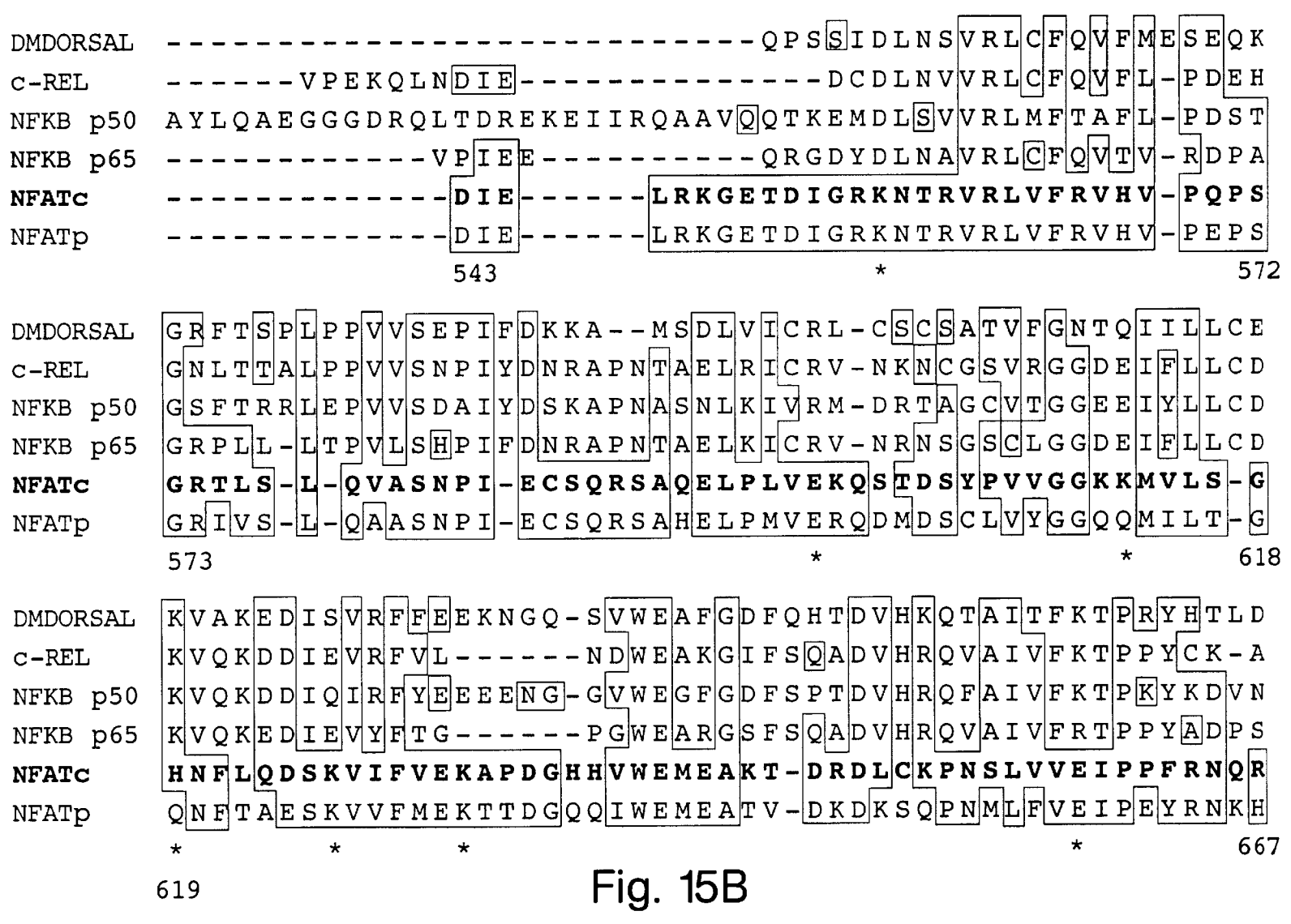
Figure 15C:
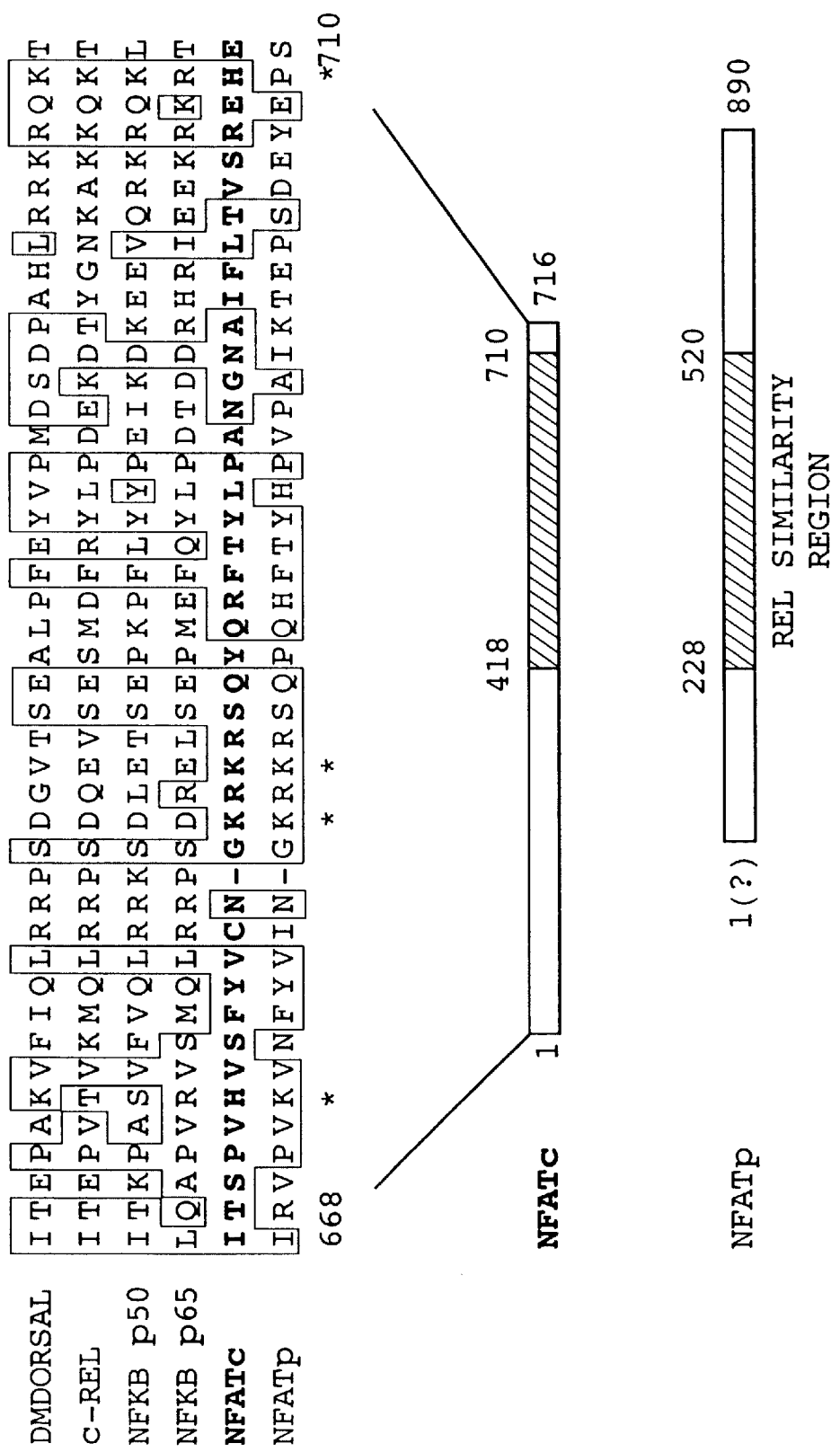

FIG. 15 (SEQ ID Nos: 47–52) shows the homology between $NF-AT_c$, $NF-AT_p$, and Rel family members. The protein sequences of murine $NF-AT_p$ and the Rel proteins Dorsal (the Drosophila axis-determining protein), human c-Rel, NF-KB p50, and NF-KB p65 are aligned to the sequence of $NF-AT_c$. Numbering is with respect to $NF-AT_c$. Identity to $NF-AT_c$, open boxes; similarity in known residue function or structure, shaded areas. Stars indicate regions in which $NF-AT_c$ has: 1) a charge reversal relative to the majority of other Rel proteins, or has 2) replaced a potential salt bridge residue with a histidine or other chelating residue. Lower portion shows a schematic of $NF-AT_c$ and $NF-AT_p$.

Figure 16A:
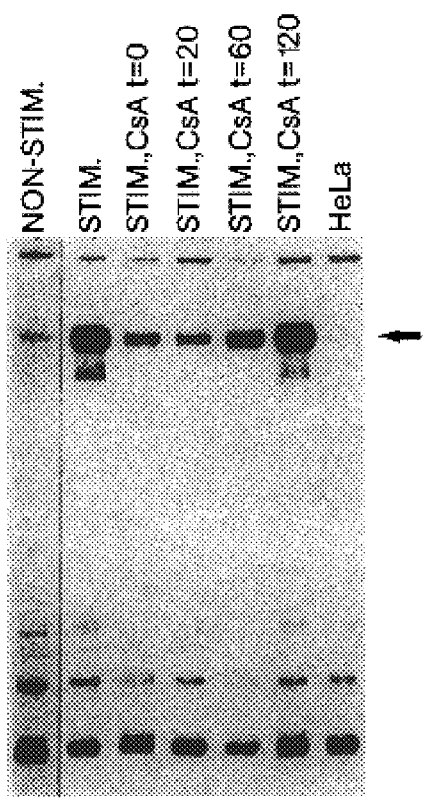
Figure 16B:
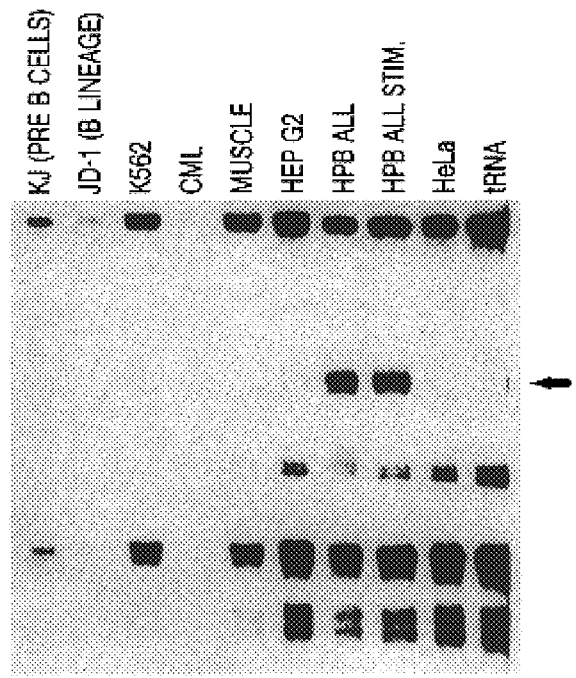
Figure 16C:
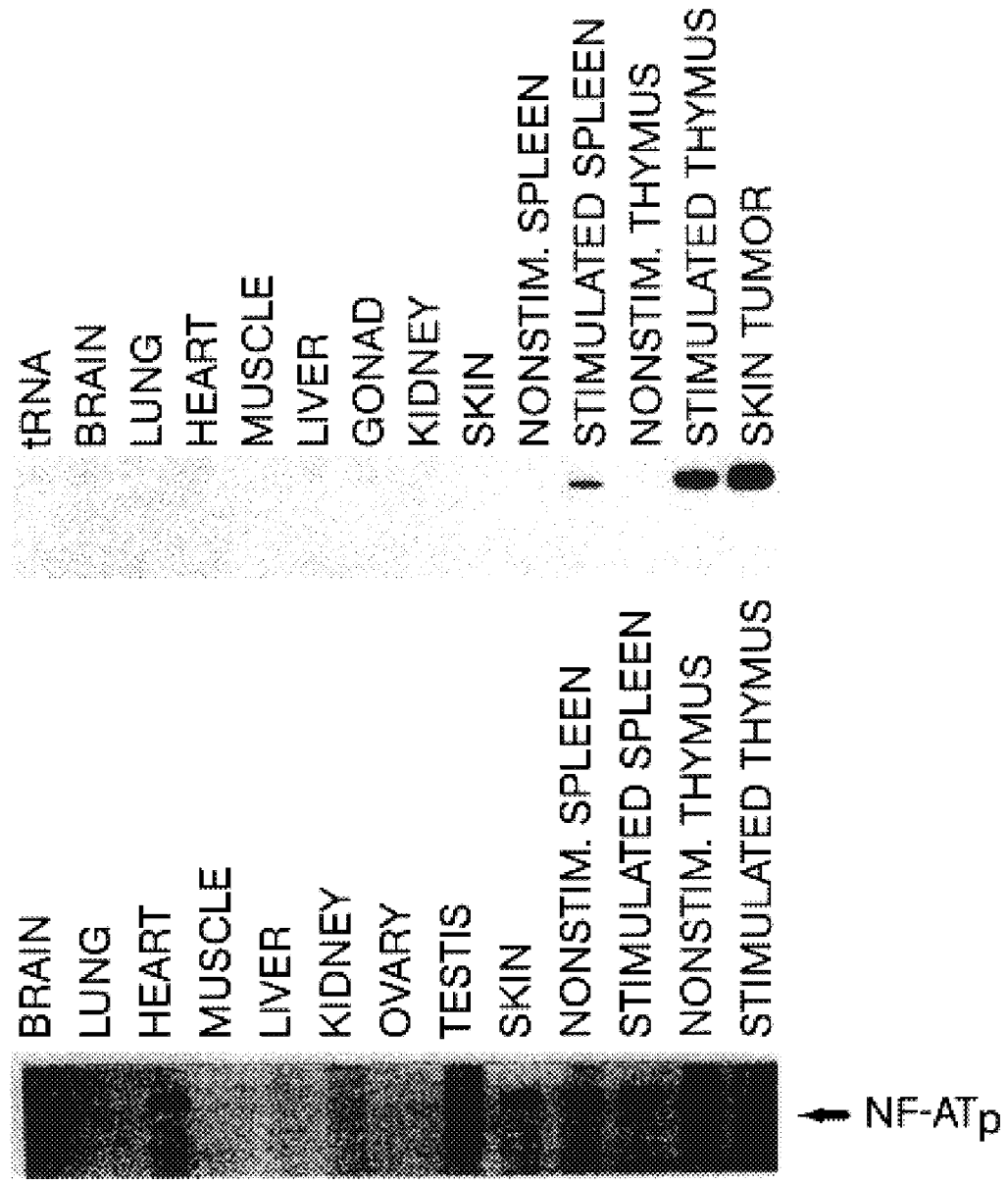
Figure 17A:
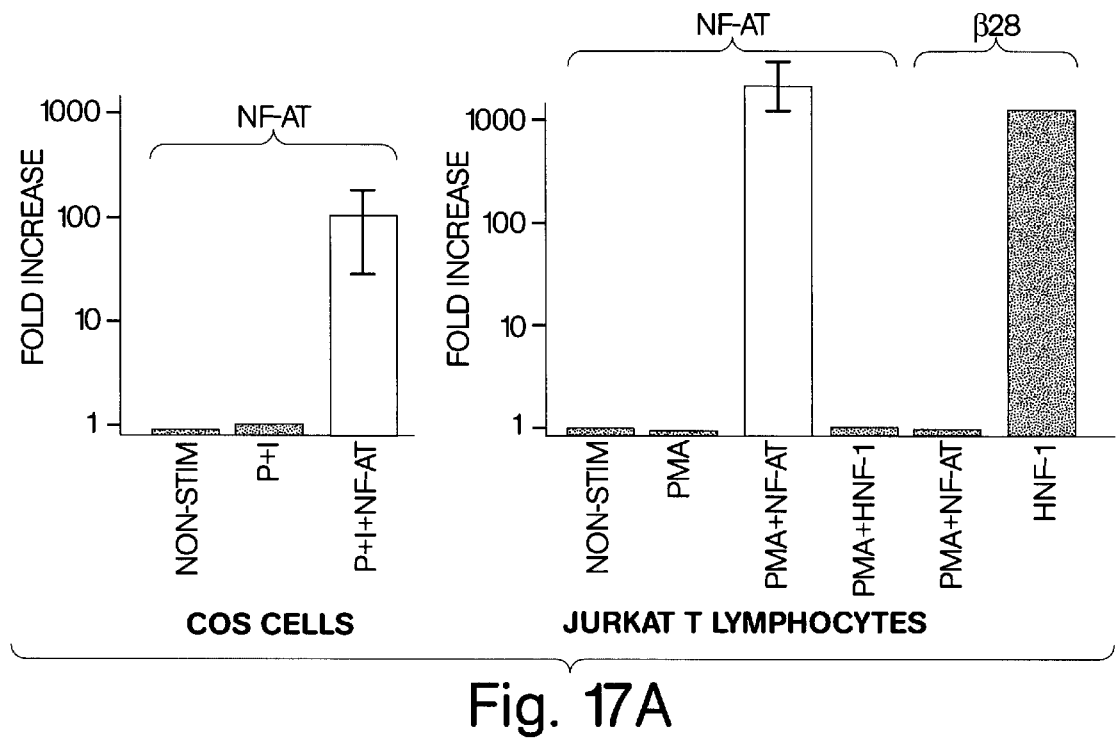
Figure 17B:
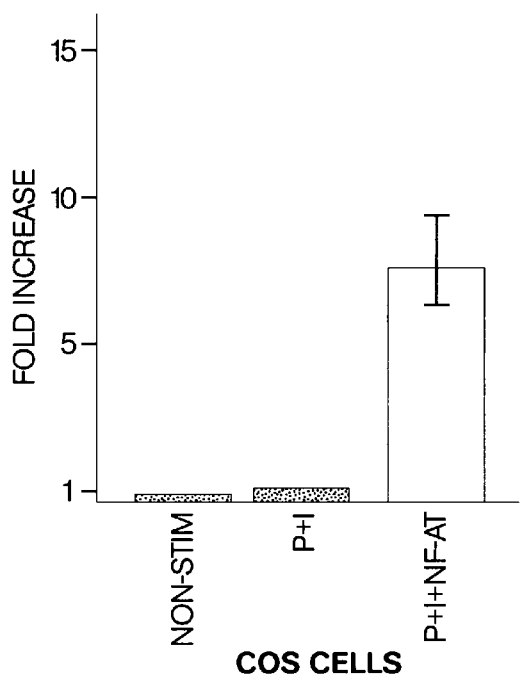
Figure 17C:
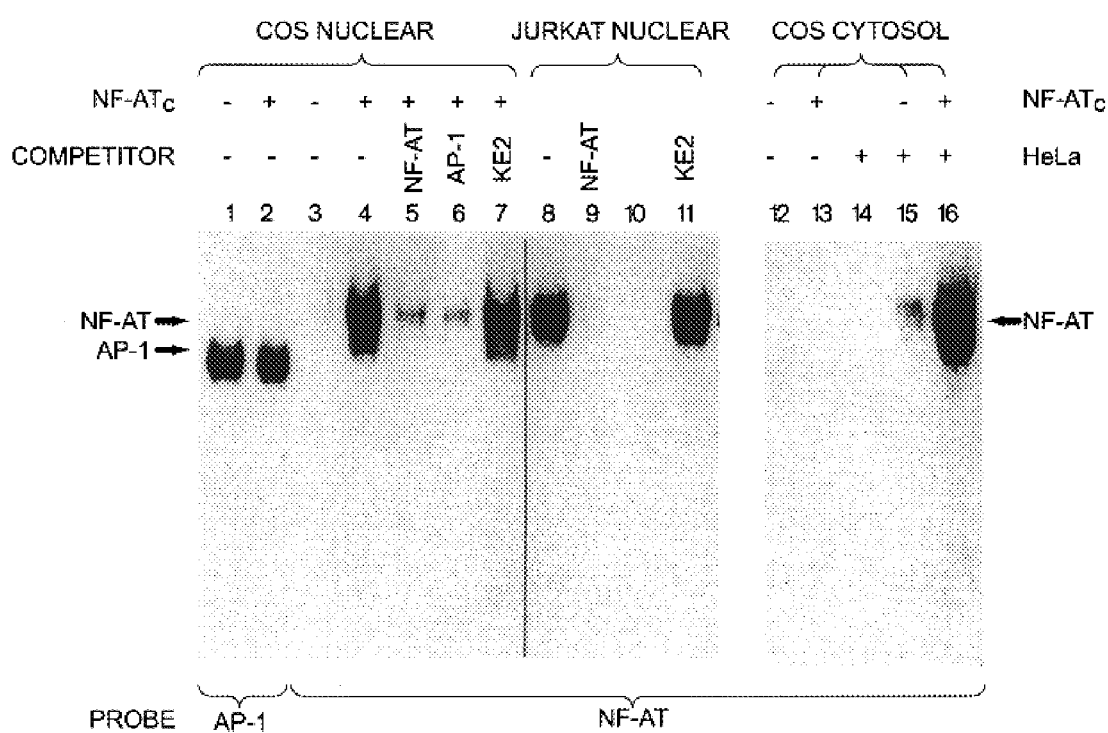
Figure 17D:
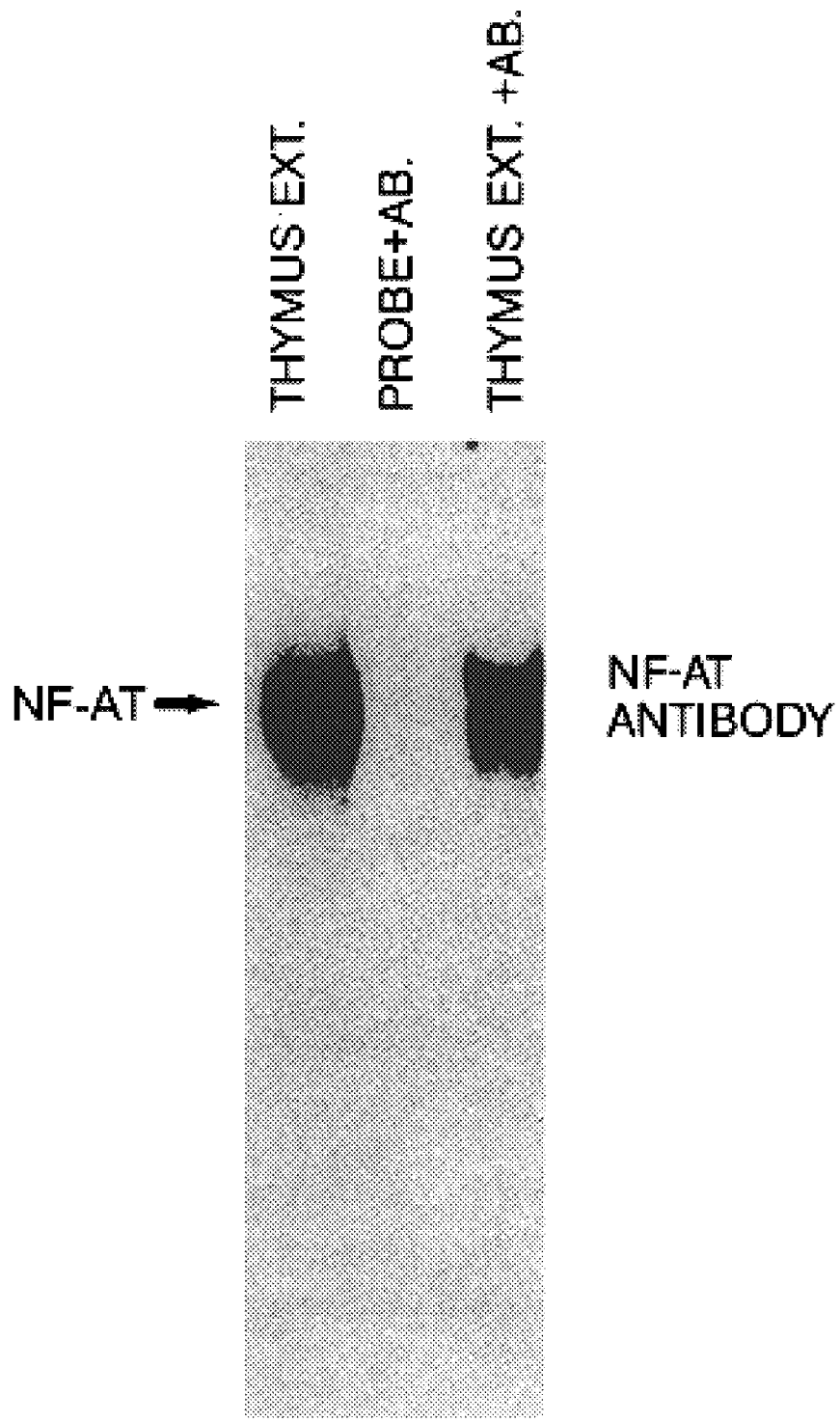

FIG. 16 (panels A–C). Panel A: Ribonuclease protection for human $NF-AT_c$ with RNA from Jurkat cells (lanes 1–6) or Hela cells (lane 7). The expected specific ribonuclease-resistant fragment is 304 nucleotides (arrow). Hela cells were non-stimulated. Jurkat cells were either non-stimulated or stimulated with 20 ng/ml PMA and 2 uM ionomycin for 3 hours, plus or minus 100 ng/ml CsA added at the indicated times after stimulation. Panel B: RNA from the following human cells: KJ (preB cell ALL), JD-1 (B cell lineage ALL), K562 (erythroleukemia cell line), CML (bone marrow cells from a patient with a myeloid leukemia), human muscle tissue, Hep G2 (liver cell line), HPB ALL (T cell line, nonstimulated or stimulated with 2 ug/mi PHA and 50 ng/ml PMA for 30 minutes), and Hela cells analyzed by ribonuclease protection. A longer exposure of this gel indicates that the K562 cell line contains a small amount of $NF-AT_c$ transcript. Panel C: $NF-AT_c$ (upper panel) and $NF-AT_p$ (lower panel) mRNA expression in mouse tissues and a skin tumor derived from NF-AT-Tag transgenic mice (Verweij et al. (1990) J. Biol. Chem 265: 15788–15795). Cells were either non-stimulated or stimulated with 20 ng/ml PMA and 2 uM ionomycin for 3 hours. RNA was measured by quantiative ribonuclease protection using murine cDNA probes. The predicted size of the fragment homologous to the probe is indicated by the arrows.

FIG. 17 (panels A–D). Panel A: Cos cells and Jurkat cells were transfected with reporter constructs for NF-AT or HNF-1 (β28). Co-transfected expression vectors for NF-AT$_c$ (+NF-AT) or HNF-1α(+HNF-1) were included where indicated, otherwise empty pBJ5 vector was included. Cells were stimulated as indicated: PMA, P+I (PMA plus ionomycin). Panel B: Cos cells were transfected with IL-2 luciferase and with expression vectors as in A. Stimulations were as in A. Data in A and B are expressed as fold induction of luciferase activity over nonstimulated value with empty pBJ5 vector. Bars represent mean and range of 2–3 independent transfections. Panel C: Expression of NF-AT$_c$ in Cos cells gives rise to specific DNA binding activity. Gel mobility shifts using nuclear extracts from Cos cells transfected with pBJ5 (lanes 1 and 3), with NF-AT$_c$ (lanes 2 and 4–7), from non-transfected Jurkat cells (lanes 8–11) or using cytosols from pBJ5- or NF-AT$_c$-transfected Cos cells (lanes 12–13, 15–16) combined with Hela nuclear extract (lanes 15–16). Lane 14, Hela nuclear extract alone. Labeled AP-1 (lanes 1–2) or NF-AT (lanes 3–16) probes and cold competitor oligonucleotides are indicated. Arrows indicate specific AP-1 and NF-AT complexes. Panel D: Antisera induced supershift of NF-AT. NF-AT and AP-1 gel mobility shifts using nuclear extracts from stimulated Jurkat cells or murine thymocytes. Either no antisera, preimmune, or one of two different immune antisera was included as indicated. Arrows indicate specific NF-AT or AP1 complexes or supershifted NF-AT complexes (*).

Figure 18:
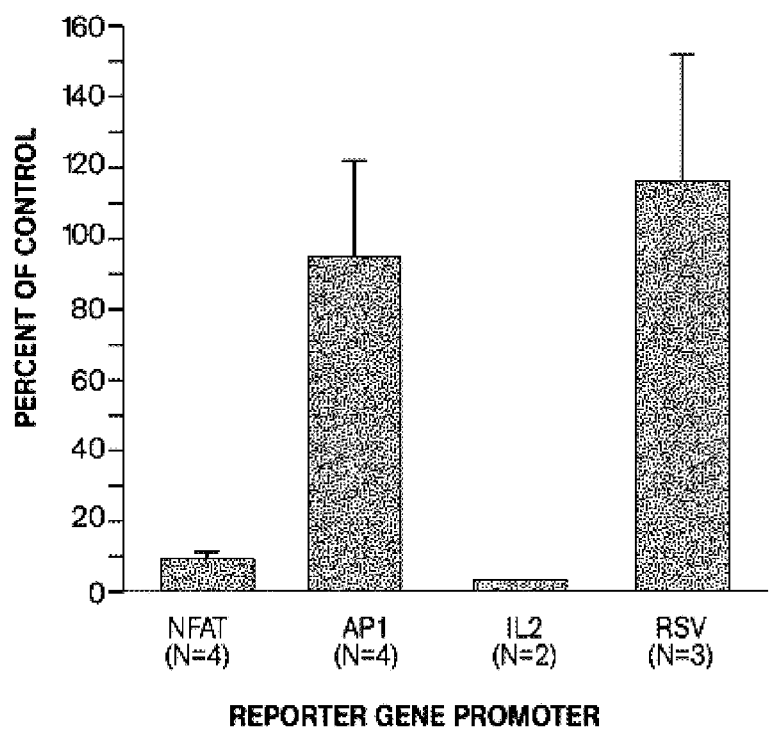

FIG. 18 shows dominant-negative NF-AT$_c$. Jurkat Tag cells were transfected with vector plasmid (control) or with the dominant negative NF-AT$_c$ plasmid, plus the indicated secreted alkaline phosphatase reporter plasmid. Transfected cells were transferred to fresh culture medium 24 hours after transfection and secreted alkaline phosphatase activity was measured (Clipstone and Crabtree (1992) *Nature* 357: 695–698) 16 to 24 hours later, after stimulation with 1 uM ionomycin plus 20 ng/ml PMA (NF-AT and IL-2 reporters), 20 ng/ml PMA alone (AP-1 reporter) or no stimulation (RSV reporter). Bars indicate, secreted alkaline phosphatase activity from cells transfected with the dominant negative NF-AT$_c$ as a percentage of the activity from cells transfected in parallel with control plasmid, and represent data obtained from (n) independent transfections. The dominant negative NF-AT$_c$ consists of a carboxy terminal truncation of the epitope tagged NF-AT$_c$ expression plasmid extending to the PvuII site at amino acid 463.

Figure 19:
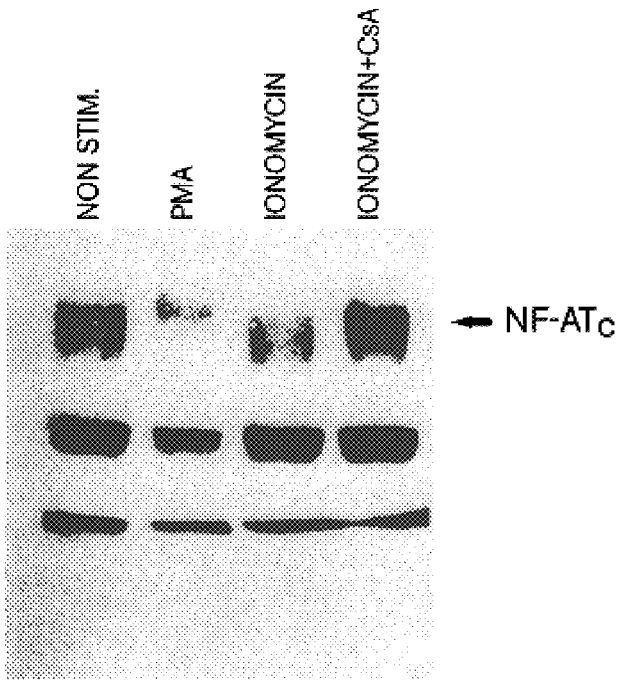

FIG. 19 shows changes in mobility of epitope tagged NF-AT$_c$ expressed in Jurkat cells. Cells were transfected with NF-AT$_c$ as in FIG. 13 and stimulated as shown for 2 hrs plus or minus 100 ng/ml CsA. Whole cell lysates were analyzed by western blotting as in FIG. 13.

DETAILED DESCRIPTION OF THE INVENTION

The present invention pertains to means of modulating transcription that is dependent upon the presence of a linked cis-acting NF-AT site as well as methods of causing and preventing formation of transcriptionally active NF-AT complexes, controlling expression of the early T lymphocyte activation genes, and controlling transcription of the human immunodeficiency virus. The invention also relates to the formation of active NF-AT from nuclear and cytoplasmic subunits by a novel mechanism; control of induction of the nuclear precursor of NF-AT, as well as control of the nuclear import of the cytoplasmic precursor of NF-AT, methods by which the nuclear import of NF-AT can be modulated and methods by which the induction of the nuclear subunit of NF-AT can be prevented or enhanced. The methods of this invention are useful in determining or controlling the expression of early T lymphocyte activation genes as well as determining or controlling the expression of selected constitutive genes that can be advantageously expressed in T lymphocytes. In addition, the invention also pertains to the development of screening assays for agents that modulate the nuclear import of the cytoplasmic subunit of NF-AT or the induction of the nuclear subunit of NF-AT, such agents are thereby identified as candidate immunosuppressant agents.

A basis of the present invention is the experimental finding that multimeric-complexes are formed when a signal from the antigen receptor induces a pre-existing cytoplasmic subunit to translocate to the nucleus and combine with a newly synthesized nuclear subunit of NF-AT. Formation of a functional multimeric complex, which includes [NF-AT$_c$:NF-AT$_n$] heterodimer, then facilitates transcriptional enhancement by interacting with specific NF-AT recognition sequences near particular structural genes, such as the IL-2 gene. Since transcriptional enhancement of early genes, such as the IL-2 gene, is a critical step in the process of T lymphocyte activation, candidate immunosuppressants can be identified by screening for agents which interfere with the formation of functional NF-AT heterodimer and/or inhibit transcriptional enhancement that entails NF-AT interacting with specific NF-AT recognition sequences.

Unless defined otherwise, all technical and scientific terms used herein have the same meaning as commonly understood by one of ordinary skill in the art to which this invention belongs. Generally, the nomenclature used hereafter and the laboratory procedures in cell culture, molecular genetics, and nucleic acid chemistry and hybridization described below are those well known and commonly employed in the art. Standard techniques are used for recombinant nucleic acid methods, polynucleotide synthesis, and microbial culture and transformation (e.g., electroporation, lipofection). Generally enzymatic reactions and purification steps are performed according to the manufacturer's specifications. The techniques and procedures are generally performed according to conventional methods in the art and various general references (see, generally, Sambrook et al. *Molecular Cloning: A Laboratory Manual*, 2d ed. (1989) Cold Spring Harbor Laboratory Press, Cold Spring Harbor, N.Y., which is incorporated herein by reference) which are provided throughout this document. The procedures therein are believed to be well known in the art and are provided for the convenience of the reader. All the information contained therein is incorporated herein by reference.

Oligonucleotides can be synthesized on an Applied Bio Systems oligonucleotide synthesizer according to specifications provided by the manufacturer.

Methods for PCR amplification are described in the art (*PCR Technology: Principles and Applications for DNA Amplification* ed. HA Erlich, Freeman Press, New York, N.Y. (1992); *PCR Protocols: A Guide to Methods and Applications*, eds. Innis, Gelfland, Snisky, and White, Academic Press, San Diego, Calif, (1990); Mattila et al. (1991) *Nucleic Acids Res.* 19: 4967; Eckert, K. A. and Kunkel, T. A. (1991) *PCR Methods and Applications* 1: 17; PCR, eds. McPherson, Quirkes, and Taylor, IRL Press, Oxford; and U.S. Pat. No. 4,683,202, which are incorporated herein by reference).

Although any methods and materials similar or equivalent to those described herein can be used in the practice or testing of the present invention, the preferred methods and materials are described. For purposes of the present invention, the following terms are defined below.

1. Definitions

As used herein, the twenty conventional amino acids and their abbreviations follow conventional usage (*Immunology—A Synthesis,* 2nd Edition, E. S. Golub and D. R. Gren, Eds., Sinauer Associates, Sunderland, Mass. (1991), which is incorporated herein by reference). Stereoisomers (e.g., D-amino acids) of the twenty conventional amino acids, unnatural amino acids such as $\alpha,\alpha$-disubstituted amino acids, N-alkyl amino acids, lactic acid, and other unconventional amino acids may also be suitable components for polypeptides of the present invention. Examples of unconventional amino acids include: 4-hydroxyproline, $\gamma$-carboxyglutamate, $\epsilon$-N,N,N-trimethyllysine, $\epsilon$-N-acetyllysine, O-phosphoserine, N-acetylserine, N-formylmethionine, 3-methylhistidine, 5-hydroxylysine, $\omega$-N-methylarginine, and other similar amino acids and imino acids (e.g., 4-hydroxyproline). In the polypeptide notation used herein, the lefthand direction is the amino terminal direction and the righthand direction is the carboxy-terminal direction, in accordance with standard usage and convention. Similarly, unless specified otherwise, the lefthand end of single-stranded polynucleotide sequences is the 5' end; the lefthand direction of double-stranded polynucleotide sequences is referred to as the 5' direction. The direction of 5' to 3' addition of nascent RNA transcripts is referred to as the transcription direction; sequence regions on the DNA strand having the same sequence as the RNA and which are 5' to the 5' end of the RNA transcript are referred to as "upstream sequences"; sequence regions on the DNA strand having the same sequence as the RNA and which are 3' to the 3' end of the RNA transcript are referred to as "downstream sequences".

The term "transcriptional enhancement" is used herein to refer to functional property of producing an increase in the rate of transcription of linked sequences that contain a functional promoter.

The term "agent" is used herein to denote a chemical compound, a mixture of chemical compounds, a biological macromolecule, or an extract made from biological materials such as bacteria, plants, fungi, or animal (particularly mammalian) cells or tissues. Agents are evaluated for potential activity as immunosupressants by inclusion in screening assays described hereinbelow.

The terms "immunosuppressant" and "immunosuppressant agent" are used herein interchangeably to refer to agents that have the functional property of inhibiting an immune response in human, particularly an immune response that is mediated by activated T cells.

The terms "candidate immunosuppressant" and "candidate immunosuppressant agent" are used herein interchangeably to refer to an agent which is identified by one or more screening method(s) of the invention as a putative inhibitor of T cell activation. Some candidate immunosuppressants may have therapeutic potential.

The term "altered ability to modulate" is used herein to refer to the capacity to either enhance transcription or inhibit transcription of a gene; such enhancement or inhibition may be contingent on the occurrence of a specific event, such as T cell stimulation. For example but not for limitation, an agent that prevents expression of NF-AT$_c$ protein will alter the ability of a T cell to modulate transcription of an IL-2 gene in response to an antigen stimulus. This alteration will be manifest as an inhibition of the transcriptional enhancement of the IL-2 gene that normally ensues following T cell stimulation. The altered ability to modulate transcriptional enhancement or inhibition may affect the inducible transcription of a gene, such as in the just-cited IL-2 example, or may effect the basal level transcription of a gene, or both.

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring.

The term "corresponds to" is used herein to mean that a polynucleotide sequence is homologous (i.e., is identical, not strictly evolutionarily related) to all or a portion of a reference polynucleotide sequence, or that a polypeptide sequence is identical to a reference polypeptide sequence. In contradistinction, the term "complementary to" is used herein to mean that the complementary sequence is homologous to all or a portion of a reference polynucleotide sequence. For illustration, the nucleotide sequence "TATAC" corresponds to a reference sequence "TATAC" and is complementary to a reference sequence "GTATA".

The following terms are used to describe the sequence relationships between two or more polynucleotides: "reference sequence", "comparison window", "sequence identity", "percentage of sequence identity", and "substantial identity". A "reference sequence" is a defined sequence used as a basis for a sequence comparison; a reference sequence may be a subset of a larger sequence, for example, as a segment of a full-length cDNA or gene sequence given in a sequence listing, such as a polynucleotide sequence of FIG. 1, or may comprise a complete cDNA or gene sequence. Generally, a reference sequence is at least 20 nucleotides in length, frequently at least 25 nucleotides in length, and often at least 50 nucleotides in length. Since two polynucleotides may each (1) comprise a sequence (i.e., a portion of the complete polynucleotide sequence) that is similar between the two polynucleotides, and (2) may further comprise a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window", as used herein, refers to a conceptual segment of at least 20 contiguous nucleotide positions wherein a polynucleotide sequence may be compared to a reference sequence of at least 20 contiguous nucleotides and wherein the portion of the polynucleotide sequence in the comparison window may comprise additions or deletions (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith and Waterman (1981) *Adv. Appl. Math.* 2: 482, by the homology alignment algorithm of Needleman and Wunsch (1970) *J. Mol. Biol.* 48: 443, by the search for similarity method of Pearson and Lipman (1988) *Proc. Natl. Acad. Sci. (U.S.A.)* 85: 2444, by computerized implementations of these algorithms (GAP, BESTFIT, FASTA, and TFASTA in the Wisconsin Genetics Software Package Release 7.0, Genetics Computer Group, 575 Science Dr., Madison, Wis.), or by inspection, and the best alignment (i.e., resulting in the highest percentage of homology over the comparison window) generated by the various methods is selected. The term "sequence identity" means that two polynucleotide sequences are identical (i.e., on a nucleotide-by-nucleotide basis) over the window of comparison. The term "percentage of sequence identity" is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparison (i.e., the window size), and multiplying the result by 100 to yield the percentage of sequence identity. The terms "substantial identity" as used herein denotes a characteristic of a polynucleotide sequence, wherein the polynucleotide comprises a sequence that has at least 85 percent sequence identity, preferably at least 90 to 95 percent sequence identity, more usually at least 99 percent sequence identity as compared to a reference sequence over a comparison window of at least 20 nucleotide positions, frequently over a window of at least 25–50 nucleotides, wherein the percentage of sequence identity is calculated by comparing the reference sequence to the polynucleotide sequence which may include deletions or additions which total 20 percent or less of the reference sequence over the window of comparison. The reference sequence may be a subset of a larger sequence, for example, as a segment of the full-length human $NF\text{-}AT_c$ polynucleotide sequence shown in FIG. 12 or the full-length murine or bovine $NF\text{-}AT_c$ cDNA sequence.

As applied to polypeptides, the term "substantial identity" means that two peptide sequences, when optimally aligned, such as by the programs GAP or BESTFIT using default gap weights, share at least 80 percent sequence identity, preferably at least 90 percent sequence identity, more preferably at least 95 percent sequence identity or more (e.g., 99 percent sequence identity). Preferably, residue positions which are not identical differ by conservative amino acid substitutions. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine.

The term "$NF\text{-}AT_c$ native protein" and "full-length $NF\text{-}AT_c$ protein" as used herein refers to a naturally-occuring $NF\text{-}AT_c$ polypeptide corresponding to the deduced amino acid sequence shown in FIG. 12 or corresponding to the deduced amino acid sequence of a cognate full-length cDNA. Also for example, a native $NF\text{-}AT_c$ protein present in naturally-occurring lymphocytes which express the $NF\text{-}AT_c$ gene are considered full-length $NF\text{-}AT_c$ proteins.

The term "$NF\text{-}AT_c$ fragment" as used herein refers to a polypeptide that has an amino-terminal and/or carboxy-terminal deletion, but where the remaining amino acid sequence is identical to the corresponding positions in the $NF\text{-}AT_c$ sequence deduced from a full-length cDNA sequence (e.g., the cDNA sequence shown in FIG. 1). $NF\text{-}AT_c$ fragments typically are at least 14 amino acids long, preferably at least 20 amino acids long, usually at least 50 amino acids long or longer.

The term "$NF\text{-}AT_c$ analog" as used herein refers to polypeptides which are comprised of a segment of at least 25 amino acids that has substantial identity to a portion of the deduced amino acid sequence shown in FIG. 12, and which has at least one of the following properties: (1) binding to other NF-AT proteins (e.g., AP-1) under suitable binding conditions, or (2) ability to localize to the nucleus upon T cell activation. Typically, $NF\text{-}AT_c$ analog polypeptides comprise a conservative amino acid substitution (or addition or deletion) with respect to the naturally-occurring sequence. $NF\text{-}AT_c$ analogs typically are at least 20 amino acids long, preferably at least 50 amino acids long or longer, most usually being as long as full-length naturally-occurring $NF\text{-}AT_c$ (e.g., as shown in FIG. 12). Some $NF\text{-}AT_c$ analogs may lack biological activity but may still be employed for various uses, such as for raising antibodies to $NF\text{-}AT_c$ epitopes, as an immunological reagent to detect and/or purify α-$NF\text{-}AT_c$ antibodies by affinity chromatography, or as a competitive or noncompetitive agonist, antagonist, or partial agonist of native $NF\text{-}AT_c$ protein function.

The term "$NF\text{-}AT_c$ polypeptide" is used herein as a generic term to refer to native protein, fragments, or analogs of $NF\text{-}AT_c$. Hence, native $NF\text{-}AT_c$, fragments of $NF\text{-}AT_c$, and analogs of $NF\text{-}AT_c$ are species of the $NF\text{-}AT_c$ polypeptide genus. Preferred $NF\text{-}AT_c$ polypeptides include: the human full-length $NF\text{-}AT_c$ protein comprising the polypeptide sequence shown in FIG. 12, or polypeptides consisting essentially of a sequence shown in Table II.

The term "cognate" as used herein refers to a gene sequence that is evolutionarily and functionally related between species. For example but not limitation, in the human genome, the human CD4 gene is the cognate gene to the mouse CD4 gene, since the sequences and structures of these two genes indicate that they are highly homologous and both genes encode a protein which functions in signaling T cell activation through MHC class II-restricted antigen recognition. Thus, the cognate murine gene to the human $NF\text{-}AT_c$ gene is the murine gene which encodes an expressed protein which has the greatest degree of sequence identity to the human $NF\text{-}AT_c$ protein and which exhibits an expression pattern similar to that of the human $NF\text{-}AT_c$ (e.g., expressed in T lineage cells). Preferred cognate $NF\text{-}AT_c$ genes are: rat $NF\text{-}AT_c$, rabbit $NF\text{-}AT_c$, canine $NF\text{-}TA_c$, nonhuman primate $NF\text{-}AT_c$, porcine $NF\text{-}AT_c$, bovine $NF\text{-}AT_c$, and hamster $NF\text{-}AT_c$.

The term "$NF\text{-}AT_c$-dependent gene" is used herein to refer to genes which: (1) have a NF-AT binding site (a site which can be specifically footprinted by NF-AT under suitable binding conditions) within about 10 kilobases of the first coding sequence of said gene, and (2) manifest an altered rate of transcription, either increased or decreased, from a major or minor transcriptional start site for said gene, wherein such alteration in transcriptional rate correlates with the presence of $NF\text{-}AT_c$ polypeptide in NF-AT complexes, such as in an activated T cell.

The term "candidate immunomodulatory agent" is used herein to refer to an agent which is identified by one or more screening method(s) of the invention as a putative immunomodulatory agent. Some candidate immunomodulatory agents may have therapeutic potential as drugs for human use.

As used herein, the terms "label" or "labeled" refers to incorporation of a detectable marker, e.g., by incorporation of a radiolabeled amino acid or attachment to a polypeptide of biotinyl moieties that can be detected by marked avidin (e.g., streptavidin containing a fluorescent marker or enzymatic activity that can be detected by optical or colorimetric methods). Various methods of labeling polypeptides and glycoproteins are known in the art and may be used. Examples of labels for polypeptides include, but are not limited to, the following: radioisotopes (e.g., $^{3}$H, $^{14}$C, $^{35}$S, $^{125}$I, $^{131}$I), fluorescent labels (e.g., FITC, rhodamine, lanthanide phosphors), enzymatic labels (e.g., horseradish peroxidase, β-galactosidase, luciferase, alkaline phosphatase), biotinyl groups, predetermined polypeptide epitopes recognized by a secondary reporter (e.g., leucine zipper pair sequences, binding sites for secondary antibodies, metal binding domains, epitope tags). In some embodiments, labels are attached by spacer arms of various lengths to reduce potential steric hindrance.

As used herein, "substantially pure" means an object species is the predominant species present (i.e., on a molar basis it is more abundant than any other individual species in the composition), and preferably a substantially purified fraction is a composition wherein the object species comprises at least about 50 percent (on a molar basis) of all macromolecular species present. Generally, a substantially pure composition will comprise more than about 80 to 90 percent of all macromolecular species present in the composition. Most preferably, the object species is purified to essential homogeneity (contaminant species cannot be detected in the composition by conventional detection methods) wherein the composition consists essentially of a single macromolecular species.

As used herein the terms "pathognomonic concentration", "pathognomonic amount", and "pathognomonic staining pattern" refer to a concentration, amount, or localization pattern, respectively, of a NF-AT$_c$ protein or mRNA in a sample, that indicates the presence of a hypofunctional or hyperfunctional T cell condition or a predisposition to developing a disease, such as graft rejection. A pathognomonic amount is an amount of a NF-AT$_c$ protein or NF-AT$_c$ mRNA in a cell or cellular sample that falls outside the range of normal clinical values that is established by prospective and/or retrospective statistical clinical studies. Generally, an individual having a neoplastic disease (e.g., lymphocytic leukemia) or T cell-mediated immune response will exhibit an amount of NF-AT$_c$ protein or mRNA in a cell or tissue sample that is higher than the range of concentrations that characterize normal, undiseased individuals; typically the pathognomonic concentration is at least about one standard deviation above the mean normal value, more usually it is at least about two standard deviations or more above the mean normal value. However, essentially all clinical diagnostic tests produce some percentage of false positives and false negatives. The sensitivity and selectivity of the diagnostic assay must be sufficient to satisfy the diagnostic objective and any relevant regulatory requirements. In general, the diagnostic methods of the invention are used to identify individuals as disease candidates, providing an additional parameter in a differential diagnosis of disease made by a competent health professional.

2. N-AT$_c$ Polynucleotides

Genomic or cDNA clones encoding NF-AT$_c$ may be isolated from clone libraries (e.g., available from Clontech, Palo Alto, Calif.) using hybridization probes designed on the basis of the nucleotide sequences shown in FIG. 12 and using conventional hybridization screening methods (e.g., Benton W D and Davis R W (1977) *Science* 196: 180; Goodspeed et al. (1989) *Gene* 76: 1; Dunn et al. (1989) *J. Biol. Chem.* 264: 13057). Where a cDNA clone is desired, clone libraries containing cDNA derived from T cell mRNA is preferred. Alternatively, synthetic polynucleotide sequences corresponding to all or part of the sequences shown in FIG. 12 may be constructed by chemical synthesis of oligonucleotides. Additionally, polymerase chain reaction (PCR) using primers based on the sequence data disclosed in FIG. 12 may be used to amplify DNA fragments from genomic DNA, mRNA pools, or from cDNA clone libraries. U.S. Pat. Nos. 4,683,195 and 4,683,202 describe the PCR method. Additionally, PCR methods employing one primer that is based on the sequence data disclosed in FIG. 12 and a second primer that is not based on that sequence data may be used. For example, a second primer that is homologous to or complementary to a polyadenylation segment may be used. In an embodiment, a polynucleotide comprising the 2742 nucleotide-long sequence of FIG. 12 can be used. Alternative polynucleotides encoding the 716 amino acid sequence of FIG. 12 can also be readily constructed by those of skill in the art by using the degeneracy of the genetic code. Polynucleotides encoding amino acids 418 to 710 of the NF-AT$_c$ sequence of FIG. 12 can also be constructed by those of skill in the art.

It is apparent to one of skill in the art that nucleotide substitutions, deletions, and additions may be incorporated into the polynucleotides of the invention. Nucleotide sequence variation may result from sequence polymorphisms of various NF-AT$_c$ alleles, minor sequencing errors, and the like. However, such nucleotide substitutions, deletions, and additions should not substantially disrupt the ability of the polynucleotide to hybridize to one of the polynucleotide sequences shown in FIG. 12 under hybridization conditions that are sufficiently stringent to result in specific hybridization.

Specific hybridization is defined herein as the formation of hybrids between a probe polynucleotide (e.g., a polynucleotide of the invention which may include substitutions, deletion, and/or additions) and a specific target polynucleotide (e.g., a polynucleotide having the sequence in FIG. 12), wherein the probe preferentially hybridizes to the specific target such that, for example, a single band corresponding to NF-AT$_c$ mRNA (or bands corresponding to multiple alternative splicing products of the NF-AT$_c$ gene) can be identified on a Northern blot of RNA prepared from a suitable cell source (e.g., a T cell expressing NF-AT$_c$). Polynucleotides of the invention and recombinantly produced NF-AT$_c$, and fragments or analogs thereof, may be prepared on the basis of the sequence data provided in FIG. 12 according to methods known in the art and described in Maniatis et al., *Molecular Cloning: A Laboratory Manual*, 2nd Ed., (1989), Cold Spring Harbor, N.Y. and Berger and Kimmel, Methods in Enzymology, Volume 152, *Guide to Molecular Cloning Techniques* (1987), Academic Press, Inc., San Diego, Calif., which are incorporated herein by reference.

NF-AT$_c$ polynucleotides may be short oligonucleotides (e.g., 25–100 bases long), such as for use as hybridization probes and PCR (or LCR) primers. NF-AT$_c$ polynucleotide sequences may also comprise part of a larger polynucleotide (e.g., a cloning vector comprising a NF-AT$_c$ clone) and may be fused, by polynucleotide linkage, in frame with another polynucleotide sequence encoding a different protein (e.g., glutathione S-transferase or β-galactosidase) for encoding expression of a fusion protein. Typically, NF-AT$_c$ polynucleotides comprise at least 25 consecutive nucleotides which are substantially identical to a naturally-occurring NF-AT$_c$ sequence (e.g., FIG. 12), more usually NF-AT$_c$ polynucleotides comprise at least 50 to 100 consecutive nucleotides which are substantially identical to a naturally-occurring NF-AT$_c$ sequence. However, it will be recognized by those of skill that the minimum length of a NF-AT$_c$ polynucleotide required for specific hybridization to a NF-AT$_c$ target sequence will depend on several factors: G/C content, positioning of mismatched bases (if any), degree of uniqueness of the sequence as compared to the population of target polynucleotides, and chemical nature of the polynucleotide (e.g., methylphosphonate backbone, phosphorothiolate, etc.), among others.

For example but not limitation, suitable hybridization probes for detecting and/or quantifying the presence of NF-AT$_c$ mRNA in a sample generally comprise at least one, preferably at least two, and more preferably all of the following human NF-AT$_c$ sequences shown in Table I, or their complements:

Each of these sequences may be used as hybridization probes or PCR amplimers to detect the presence of NF-AT$_c$ mRNA, for example to diagnose a disease characterized by the presence of an elevated NF-AT$_c$ mRNA level in lymphocytes, or to perform tissue typing (i.e., identify tissues characterized by the expression of NF-AT$_c$ mRNA), and the like. The sequences may also be used for detecting genomic NF-AT$_c$ gene sequences in a DNA sample, such as for forensic DNA analysis (e.g., by RFLP analysis, PCR product length(s) distribution, etc.) or for diagnosis of diseases characterized by amplification and/or rearrangements of the NF-AT$_c$ gene.

Disclosure of the full coding sequence for human NF-AT$_c$ shown in FIG. 12 makes possible the construction of isolated polynucleotides that can direct the expression of NF-AT$_c$,

TABLE I

Selected Human NF-AT$_c$ Polynucleotide Sequences

| | |
|---|---|
| 5'-TTC CTC CGG GGC GCG CGG CGT GAG CCC GGG GCG AGG-3' | (SEQ ID NO: 1); |
| 5'-CAG CGC GGG GCG GCC ACT TCT CCT GTG CCT CCG CCC GCT GCT-3' | (SEQ ID NO: 2); |
| 5'-GCC GCG CGG ATG CCA AGC ACC AGC TTT CCA GTC CCT TCC AAG-3' | (SEQ ID NO: 3); |
| 5'-CCA ACG TCA GCC CCG CCC TGC CGC TCC CCA CGG CGC ACT CCA-3' | (SEQ ID NO: 4); |
| 5'-TTC AGA CCT CCA CAC CGG GCA TCA TCC CGC CGG CGG-3' | (SEQ ID NO: 5); |
| 5'-GCC ACA CCA GGC CTG ATG GGG CCC CTG CCC TGG AGA GTC CTC-3' | (SEQ ID NO: 6); |
| 5'-AGT CTG CCC AGC CTG GAG GCC TAC AGA GAC CCC TCG TGC CTG-3' | (SEQ ID NO: 7); |
| 5'-GTG TCT CCC AAG ACC ACG GAC CCC GAG GAG GGC TTT CCC-3' | (SEQ ID NO: 8); |
| 5'-AGC TGG CTG GGT GCC CGC TCC TCC AGA CCC GCG TCC CCT TGC-3' | (SEQ ID NO: 9); |
| 5'-TAC AGC CTC AAC GGC CGG CAG CCG CCC TAC TCA CCC CAC CAC-3' | (SEQ ID NO: 10); |
| 5'-GAC CAC CGA CAG CAG CCT GGA CCT GGG AGA TGG CGT CCC TGT-3' | (SEQ ID NO: 11); |
| 5'-CCT GGG CAG CCC CCC GCC CCC GGC CGA CTT CGC GCC CGA AGA-3' | (SEQ ID NO: 12); |
| 5'-GCT CCC CTA CCA GTG GCG AAG CCC AAG CCC CTG TCC CCT ACG-3' | (SEQ ID NO: 13); |
| 5'-CTT CGG ATT GAG GTG CAG CCC AAG TCC CAC CAC CGA GCC CAC-3' | (SEQ ID NO: 14); |
| 5'-CAT GGC TAC TTG GAG AAT GAG CCG CTG ATG CTG CAG CTT TTC-3' | (SEQ ID NO: 15); |
| 5'-AAG ACC GTG TCC ACC ACC AGC CAC GAG GCT ATC CTC TCC AAC-3' | (SEQ ID NO: 16); |
| 5'-TCA GCT CAG GAG CTG CCT CTG GTG GAG AAG CAG AGC ACG GAC-3' | (SEQ ID NO: 17); |
| 5'-AAC GCC ATC TTT CTA ACC GTA AGC CGT GAA CAT GAG CGC G-3' | (SEQ ID NO: 18); |
| 5'-AGA AAC GAC GTC GCC GTA AAG CAG CGT GGC GTG TGG CA-3' | (SEQ ID NO: 19); and |
| 5'-GCA TAC TCA GAT AGT CAC GGT TAT TTT GCT TCT TGC GAA TG-3' | (SEQ ID NO: 20). |

Also for example but not limitation, the following pair of PCR primers (amplimers) may be used to amplify murine or human NF-AT$_c$ sequences (e.g., by reverse transcriptase initiated PCR of RNA from NF-AT$_c$ expressing cells):
(forward)
    5'-AGGGCGCGGGCACCGGGGCGCGGGCAGGGC-TCGGAG-3' (SEQ ID NO: 21)
(reverse)
    5'-GCAAGAAGCAAAATAACCGTGACTATCTGAG-TATGC-3' (SEQ ID NO: 22)
If desired, PCR amplimers for amplifying substantially full-length cDNA copies may be selected at the discretion of the practioner. Similarly, amplimers to amplify single NF-AT$_c$ exons or portions of the NF-AT$_c$ gene (murine or human) may be selected.

fragments thereof, or analogs thereof. Further, the sequences in FIG. 12 make possible the construction of nucleic acid hybridization probes and PCR primers that can be used to detect RNA and DNA sequences encoding NF-AT$_c$.

Polynucleotides encoding full-length NF-AT$_c$ or fragments or analogs thereof, may include sequences that facilitate transcription (expression sequences) and translation of the coding sequences, such that the encoded polypeptide product is produced. Construction of such polynucleotides is well known in the art and is described further in Maniatis et al., *Molecular Cloning: A Laboratory Manual*, 2nd Ed. (1989), Cold Spring Harbor, N.Y. For example, but not for limitation, such polynucleotides can include a promoter, a transcription termination site (polyadenylation site in eukaryotic expression hosts), a ribosome binding site, and, optionally, an enhancer for use in eukaryotic expression hosts, and, optionally, sequences necessary for replication of a vector. A typical eukaryotic expression cassette will include a polynucleotide sequence encoding a NF-AT$_c$ polypeptide linked downstream (i.e., in translational reading frame orientation; polynucleotide linkage) of a promoter such as the HSV tk promoter or the pgk (phosphoglycerate kinase) promoter, optionally linked to an enhancer and a downstream polyadenylation site (e.g., an SV40 large T Ag poly A addition site).

A preferred NF-AT$_c$ polynucleotide encodes a NF-AT$_c$ polypeptide that comprises at least one of the following amino acids sequences:
-NAIFLTVSREHERVGC-(SEQ ID NO: 25);
-LHGYLENEPLMLQLFIGT-(SEQ ID NO: 26);
-PSTSPRASVTEESWLG-(SEQ ID NO: 27);
-GPAPRAGGTMKSAEEEHYG-(SEQ ID NO: 28);
-ASAGGHPIVQ-(SEQ ID NO: 29);
-NTRVRLVFRV-(SEQ ID NO: 30);
-AKTDRDLCKPNSLVVEIPPFRN-(SEQ ID NO: 31);
-EVQPKSHHRAHTEGSR-(SEQ ID NO: 32);
-SPRVSVTDDSWLGNT-(SEQ ID NO: 33);
-SHHRAHYETEGSRGAV-(SEQ ID NO: 34);
-LRNSDIELRKGETDIGR-(SEQ ID NO: 35); and
-TLSLQVASNPIEC-(SEQ ID NO: 36).

The degeneracy of the genetic code gives a finite set of polynucleotide sequences encoding these amino acid sequences; this set of degenerate sequences may be readily generated by hand or by computer using commercially available software (Wisconsin Genetics Software Package Relaes 7.0). Thus, isolated polynucleotides typically less than approximately 10,000 nucleotides in length and comprising sequences encoding each of the following amino acid sequences:
-NAIFLTVSREHERVGC-(SEQ ID NO: 25);
-LHGYLENEPLMLQLFIGT-(SEQ ID NO: 26);
-PSTSPRASVTEESWLG-(SEQ ID NO: 27);
-GPAPRAGGTMKSAEEEHYG-(SEQ ID NO: 28);
-ASAGGHPIVQ-(SEQ ID NO: 29);
-NTRVRLVFRV-(SEQ ID NO: 30);
-AKTDRDLCKPNSLVVEIPPFRN-(SEQ ID NO: 31);
-EVQPKSHHRAHYETEGSR-(SEQ ID NO: 32);
-SPRVSVTDDSWLGNT-(SEQ ID NO: 33);
-SHHRAHYETEGSRGAV-(SEQ ID NO: 34);
-LRNSDIELRKGETDIGR-(SEQ ID NO: 35); and
-TLSLQVASNPIEC-(SEQ ID NO: 36).
are provided and may be used for, among other uses, the expression of a NF-AT$_c$ polypeptide which can be used as an immunogen, immunological reagent, and the like. Such polynucleotides typically comprise an operably linked promoter for driving expression in a suitable prokaryotic or eukaryotic host cell. One exemplification of such a polynucleotide is the human NF-AT$_c$ cDNA sequence of FIG. 12 cloned in operable linkage to the mammalian expression vector pSRα, many alternative embodiments will be apparent to those of skill in the art, including the use of alternative expression vectors (e.g., pBC12BI and p91023(B); Hanahan J (1983) *J. Mol. Biol.* 166: 577; Cullen et al. (1985) *J. Virol.* 53: 515; Lomedico PT (1982) *Proc. Natl. Acad. Sci. (U.S.A)* 79: 5798; Morinaga et al. (1984) *Bio/Technology* 2: 636).

Additionally, where expression of a polypeptide is not desired, polynucleotides of this invention need not encode a functional protein. Polynucleotides of this invention may serve as hybridization probes and/or PCR primers (amplimers) and/or LCR oligomers for detecting NF-AT$_c$ RNA or DNA sequences.

Alternatively, polynucleotides of this invention may serve as hybridization probes or primers for detecting RNA or DNA sequences of related genes, such genes may encode structurally or evolutionarily related proteins. For such hybridization and PCR applications, the polynucleotides of the invention need not encode a functional polypeptide. Thus, polynucleotides of the invention may contain substantial deletions, additions, nucleotide substitutions and/or transpositions, so long as specific hybridization or specific amplification to the NF-AT$_c$ sequence is retained.

Specific hybridization is defined hereinbefore, and can be roughly summarized as the formation of hybrids between a polynucleotide of the invention (which may include substitutions, deletions, and/or additions) and a specific target polynucleotide such as human NF-AT$_c$ mRNA so that a single band is identified corresponding to each NF-AT$_c$ isoform on a Northern blot of RNA prepared from T cells (i.e., hybridization and washing conditions can be established that permit detection of discrete NF-AT$_c$ mRNA band(s)). Thus, those of ordinary skill in the art can prepare polynucleotides of the invention, which may include substantial additions, deletions, substitutions, or transpositions of nucleotide sequence as compared to sequences shown in FIG. 12 and determine whether specific hybridization is a property of the polynucleotide by performing a Northern blot using RNA prepared from a T lymphocyte cell line which expresses NF-AT$_c$ mRNA and/or by hybridization to a NF-AT$_c$ DNA clone (cDNA or genomic clone).

Specific amplification is defined as the ability of a set of PCR amplimers, when used together in a PCR reaction with a NF-AT$_c$ polynucleotide, to produce substantially a single major amplification product which corresponds to a NF-AT$_c$ gene sequence or mRNA sequence. Generally, human genomic DNA or mRNA from NF-AT$_c$ expressing human cells (e.g., Jurkat cell line) is used as the template DNA sample for the PCR reaction. PCR amplimers that exhibit specific amplification are suitable for quantitative determination of NF-AT$_c$ mRNA by quantitative PCR amplification. NF-AT$_c$ allele-specific amplification products, although having sequence and/or length polymorphisms, are considered to constitute a single amplification product for purposes of this definition.

Generally, hybridization probes comprise approximately at least 25 consecutive nucleotides of a sequence shown in FIG. 12 (for human and murine NF-AT$_c$ detection, respectively), preferably the hybridization probes contain at least 50 consecutive nucleotides of a sequence shown in FIG. 12, and more preferably comprise at least 100 consecutive nucleotides of a sequence shown in FIG. 12. PCR amplimers typically comprise approximately 25 to 50 consecutive nucleotides of a sequence shown in FIG. 12, and usually consist essentially of approximately 25 to 50 consecutive nucleotides of a sequence shown in FIG. 12 with additional nucleotides, if present, generally being at the 5' end so as not to interfere with polymerase-mediated chain extension. PCR amplimer design and hybridization probe selection are well within the scope of discretion of practioners of ordinary skill in the art.

In one preferred embodiment of the invention, hybridization probes that specifically identify the NF-AT$_c$ gene may be used in methods for diagnosing genetic disease. For example, but not for limitation, the genetic disease thus diagnosed may involve a lesion in the relevant NF-AT$_c$ structural or regulatory sequences, or may involve a lesion in a genetic locus closely linked to the NF-AT$_c$ locus and which can be identified by restriction fragment length polymorphism or DNA sequence polymorphism at the linked NF-AT$_c$ locus. In a further preferred embodiment, NF-AT$_c$ gene probes are used to diagnose or identify genetic disease involving predisposition to immunological disease, wherein the amount or functionality of endogenous NF-AT$_c$ is sufficient for the individual to exhibit an increased probability of developing an immune disease, particularly an immune deficiency, arthritis, or autoimmune disease.

3. Isolation of the Cognate Human NF-AT$_c$ Gene

The human homolog of the NF-AT$_c$ cDNA is identified and isolated by screening a human genomic clone library, such as a human genomic library in yeast artificial chromosomes, cosmids, or bacteriophage λ (e.g., λ Charon 35), with a polynucleotide probe comprising a sequence of about at least 24 contiguous nucleotides (or their complement) of the cDNA sequence shown in FIG. 12. Typically, hybridization and washing conditions are performed at high stringency according to conventional hybridization procedures. Positive clones are isolated and sequenced. For illustration and not for limitation, a full-length polynucleotide corresponding to the sequence of FIG. 12 may be labeled and used as a hybridization probe to isolate genomic clones from a human or murine genomic clone library in λEMBL4 or λGEM11 (Promega Corporation, Madison, Wis.); typical hybridization conditions for screening plaque lifts (Benton and Davis (1978) Science 196: 180) can be: 50% formamide, 5×SSC or SSPE, 1–5×Denhardt's solution, 0.1–1% SDS, 100–200 μg sheared heterologous DNA or tRNA, 0–10% dextran sulfate, $1\times10^5$ to $1\times10^7$ cpm/ml of denatured probe with a specific activity of about $1\times10^8$ cpm/μg, and incubation at 42° C. for about 6–36 hours. Prehybridization conditions are essentially identical except that probe is not included and incubation time is typically reduced. Washing conditions are typically 1–3× SSC, 0.1–1% SDS, 50–70° C. with change of wash solution at about 5–30 minutes.

Nonhuman NF-AT$_c$ cDNAs and genomic clones (i.e., cognate nonhuman NF-AT$_c$ genes) can be analogously isolated from various nonhuman cDNA and genomic clone libraries available in the art (e.g., Clontech, Palo Alto, Calif.) by using probes based on the sequences shown in FIG. 12, with hybridization and washing conditions typically being less stringent than for isolation of human NF-AT$_c$ clones.

Polynucleotides comprising sequences of approximately at least 30–50 nucleotides, preferably at least 100 nucleotides, corresponding to or complementary to the nucleotide sequences shown in FIG. 12 can serve as PCR primers and/or hybridization probes for identifying and isolating germline genes corresponding to NF-AT$_c$. These germline genes may be human or may be from a related mammalian species, preferably rodents or primates. Such germline genes may be isolated by various methods conventional in the art, including, but not limited to, by hybridization screening of genomic libraries in bacteriophage λ or cosmid libraries, or by PCR amplification of genomic sequences using primers derived from the sequences shown in FIG. 12. Human genomic libraries are publicly available or may be constructed de novo from human DNA.

Genomic clones of NF-AT$_c$, particularly of the murine cognate NF-AT gene, may be used to construct homologous targeting constructs for generating cells and transgenic non-human animals having at least one functionally disrupted NF-AT$_c$ allele, preferably homozygous for knocked out NF-AT$_c$ alleles. Guidance for construction of homologous targeting constructs may be found in the art, including: Rahemtulla et al. (1991) Nature 353: 180; Jasin et al. (1990) Genes Devel. 4: 157; Koh et al. (1992) Science 256: 1210; Molina et al. (1992) Nature 357: 161; Grusby et al. (1991) Science 253: 1417; Bradley et al. (1992) Bio/Technology 10: 534, incorporated herein by reference). Homologous targeting can be used to generate so-called "knockout" mice, which are heterozygous or homozygous for an inactivated NF-AT$_c$ allele. Such mice may be sold commercially as research animals for investigation of immune system development, neoplasia, T cell activation, signal transduction, drug sreening, and other uses.

Chimeric targeted mice are derived according to Hogan, et al., *Manipulating the Mouse Embryo: A Laboratory Manual*, Cold Spring Harbor Laboratory (1988) and *Teratocarcinomas and Embryonic Stem Cells*: A Practical Approach, E. J. Robertson, ed., IRL Press, Washington, D.C., (1987) which are incorporated herein by reference. Embryonic stem cells are manipulated according to published procedures (*Teratocarcinomas and Embryonic Stem Cells: A Practical Approach*, E. J. Robertson, ed., IRL Press, Washington, D.C. (1987); Zjilstra et al. (1989) Nature 342:435; and Schwartzberg et al. (1989) Science 246: 799, each of which is incorporated herein by reference).

Additionally, a NF-AT$_c$ cDNA or genomic gene copy may be used to construct transgenes for expressing NF-AT$_c$ polypeptides at high levels and/or under the transcriptional control of transcription control sequences which do not naturally occur adjacent to the NF-AT$_c$ gene. For example but not limitation, a constitutive promoter (e.g., a HSV-tk or pgk promoter) or a cell-lineage specific transcriptional regulatory sequence (e.g., a CD4 or CD8 gene promoter/enhancer) may be operably linked to a NF-AT$_c$-encoding polynucleotide sequence to form a transgene (typically in combination with a selectable marker such as a neo gene expression cassette). Such transgenes can be introduced into cells (e.g., ES cells, hematopoietic stem cells) and transgenic cells and transgenic nonhuman animals may be obtained according to conventional methods. Transgenic cells and/or transgenic nonhuman animals may be used to screen for antineoplastic agents and/or to screen for potential immunomodulatory agents, as overexpression of NF-AT$_c$ or inappropriate expression of NF-AT$_c$ may result in a hyperimmune state or enhance graft rejection reactions.

4. Antisense Polynucleotides

Additional embodiments directed to modulation of T cell activation include methods that employ specific antisense polynucleotides complementary to all or part of the sequences shown in FIG. 12. Such complementary antisense polynucleotides may include nucleotide substitutions, additions, deletions, or transpositions, so long as specific hybridization to the relevant target sequence corresponding to FIG. 12 is retained as a functional property of the polynucleotide. Complementary antisense polynucleotides include soluble antisense RNA or DNA oligonucleotides which can hybridize specifically to NF-AT$_c$ mRNA species and prevent transcription of the mRNA species and/or translation of the encoded polypeptide (Ching et al. (1989) Proc. Natl. Acad. Sci. U.S.A. 86:10006; Broder et al. (1990) Ann. Int. Med. 113: 604; Loreau et al. (1990) FEBS Letters 274: 53; Holcenberg et al., WO91/11535; U.S. Ser. No. 07/530,165; WO91/09865; WO91/04753; WO90/13641; and EP 386563, each of which is incorporated herein by reference). The antisense polynucleotides therefore inhibit production of NF-AT$_c$ polypeptides. Since NF-AT$_c$ protein expression is associated with T lymphocyte activation, antisense polynucleotides that prevent transcription and/or translation of mRNA corresponding to NF-AT$_c$ polypeptides may inhibit T cell activation and/or reverse the activated phenotype of T cells. Compositions containing a therapeutically effective dosage of NF-AT$_c$ antisense polynucleotides may be administered for treatment of immune diseases, including lymphocytic leukemias, and for inhibition of transplant rejection reactions, if desired. Antisense polynucleotides of various lengths may be produced, although such antisense polynucleotides typically comprise a sequence of about at least 25 consecutive nucleotides which are substantially identical to a naturally-occurring NF-AT$_c$ polynucleotide sequence, and typically which are identical to a sequence shown in FIG. 12.

Antisense polynucleotides may be produced from a heterologous expression cassette in a transfectant cell or transgenic cell, such as a transgenic pluripotent hematopoietic stem cell used to reconstitute all or part of the hematopoietic stem cell population of an individual. Alternatively, the antisense polynucleotides may comprise soluble oligonucleotides that are administered to the external milieu, either in the culture medium in vitro or in the circulatory system or interstitial fluid in vivo. Soluble antisense polynucleotides present in the external milieu have been shown to gain access to the cytoplasm and inhibit translation of specific mRNA species. In some embodiments the antisense polynucleotides comprise methylphosphonate moieties. For general methods relating to antisense polynucleotides, see Antisense RNA and DNA, (1988), D. A. Melton, Ed., Cold Spring Harbor Laboratory, Cold Spring Harbor, N.Y.).

5. NF-AT$_c$ Polypeptides

The nucleotide and amino acid sequences shown in FIG. 12 enable those of skill in the art to produce polypeptides corresponding to all or part of the full-length human NF-AT$_c$ polypeptide sequence. Such polypeptides may be produced in prokaryotic or eukaryotic host cells by expression of polynucleotides encoding NF-AT$_c$, or fragments and analogs thereof. Alternatively, such polypeptides may be synthesized by chemical methods or produced by in vitro translation systems using a polynucleotide template to direct translation. Methods for expression of heterologous proteins in recombinant hosts, chemical synthesis of polypeptides, and in vitro translation are well known in the art and are described further in Maniatis et al., *Molecular Cloning: A Laboratory Manual* (1989), 2nd Ed., Cold Spring Harbor, N.Y. and Berger and Kimmel, *Methods in Enzymology, Volume* 152, *Guide to Molecular Cloning Techniques* (1987), Academic Press, Inc., San Diego, Calif.

Fragments or analogs of NF-AT$_c$ may be prepared by those of skill in the art. Preferred amino- and carboxy-termini of fragments or analogs of NF-AT$_c$ occur near boundaries of functional domains. For example, but not for limitation, such functional domains include: (1) domains conferring the property of binding to other NF-AT components (e.g., AP-1), (2) domains conferring the property of nuclear localization in stimulated T lymphocytes, and (3) domains conferring the property of enhancing activation of T cells when expressed at sufficient levels in such cells. Additionally, such functional domains might include: (1) domains conferring the property of binding to RNA polymerase species, (2) domains having the capacity to directly alter local chromatin structure, which may comprise catalytic activities (e.g., topoisomerases, endonucleases) and/or which may comprise structural features (e.g., zinc fingers, histone-binding moieties), and (3) domains which may interact with accessory proteins and/or transcription factors.

One method by which structural and functional domains may be identified is by comparison of the nucleotide and/or amino acid sequence data shown in FIG. 12 to public or proprietary sequence databases. Preferably, computerized comparison methods are used to identify sequence motifs or predicted protein conformation domains that occur in other proteins of known structure and/or function, such as the zinc fingers. For example, the NAD-binding domains of dehydrogenases, particularly lactate dehydrogenase and malate dehydrogenase, are similar in conformation and have amino acid sequences that are detectably homologous (*Proteins, Structures and Molecular Principles*, (1984) Creighton (ed.), W. H. Freeman and Company, New York, which is incorporated herein by reference). Further, a method to identify protein sequences that fold into a known three-dimensional structure are known (Bowie et al. (1991) *Science* 253: 164). Thus, the foregoing examples demonstrate that those of skill in the art can recognize sequence motifs and structural conformations that may be used to define structural and functional domains in the NF-AT$_c$ sequences of the invention. One example of a domain is the rel similarity region from amino acid 418 to amino acid 710 of the NF-AT$_c$ polypeptide sequence of FIG. 12.

Additionally, computerized comparison of sequences shown in FIG. 12 to existing sequence databases can identify sequence motifs and structural conformations found in other proteins or coding sequences that indicate similar domains of the NF-AT$_c$ protein. For example but not for limitation, the programs GAP, BESTFIT, FASTA, and TFASTA in the Wisconsin Genetics Software Package (Genetics Computer Group, 575 Science Dr., Madison, Wis.) can be used to identify sequences in databases, such as GenBank/EMBL, that have regions of homology with a NF-AT$_c$ sequences. Such homologous regions are candidate structural or functional domains. Alternatively, other algorithms are provided for identifying such domains from sequence data. Further, neural network methods, whether implemented in hardware or software, may be used to: (1) identify related protein sequences and nucleotide sequences, and (2) define structural or functional domains in NF-AT$_c$ polypeptides (Brunak et al. (1991) *J. Mol. Biol.* 220: 49, which is incorporated herein by reference). For example, the 13-residue repeat motifs—SPRASVTEESWLG-(SEQ ID NO: 23) and -SPRVSVTDDSWLG-(SEQ ID NO: 24) are examples of structurally related domains.

Fragments or analogs comprising substantially one or more functional domain may be fused to heterologous polypeptide sequences, wherein the resultant fusion protein exhibits the functional property(ies) conferred by the NF-AT$_c$ fragment. Alternatively, NF-AT$_c$ polypeptides wherein one or more functional domain have been deleted will exhibit a loss of the property normally conferred by the missing fragment.

By way of example and not limitation, the domain conferring the property of nuclear localization and/or interaction with AP-1 may be fused to β-galactosidase to produce a fusion protein that is localized to the nucleus and which can enzymatically convert a chromogenic substrate to a chromophore.

Although one class of preferred embodiments are fragments having amino- and/or carboxy-termini corresponding to amino acid positions near functional domains borders, alternative NF-AT$_c$ fragments may be prepared. The choice of the amino- and carboxy-termini of such fragments rests with the discretion of the practitioner and will be made based on experimental considerations such as ease of construction, stability to proteolysis, thermal stability, immunological reactivity, amino- or carboxyl-terminal residue modification, or other considerations.

In addition to fragments, analogs of NF-AT$_c$ can be made. Such analogs may include one or more deletions or additions of amino acid sequence, either at the amino- or carboxy-termini, or internally, or both; analogs may further include sequence transpositions. Analogs may also comprise amino acid substitutions, preferably conservative substitutions. Additionally, analogs may include heterologous sequences generally linked at the amino- or carboxy-terminus, wherein the heterologous sequence(s) confer a functional property to the resultant analog which is not indigenous to the native NF-AT$_c$ protein. However, NF-AT$_c$ analogs must comprise a segment of 25 amino acids that has substantial similarity to a portion of the amino acid sequence shown in FIG. 12, respectively, and which has at least one of the requisite functional properties enumerated in the Definitions (supra). Preferred amino acid substitutions are those which: (1) reduce susceptibility to proteolysis, (2) reduce susceptibility to oxidation, (3) alter post-translational modification of the analog, possibly including phosphorylation, and (4) confer or modify other physicochemical or functional properties of such analogs, possibly including interaction with calcineurin or phophorylation or dephosphorylation thereby. NF-AT$_c$ analogs include various muteins of a NF-AT$_c$ sequence other than the naturally-occurring peptide sequence. For example, single or multiple amino acid substitutions (preferably conservative amino acid substitutions) may be made in the naturally-occurring NF-AT$_c$ sequence (preferably in the portion of the polypeptide outside the functional domains).

Conservative amino acid substitution is a substitution of an amino acid by a replacement amino acid which has similar characteristics (e.g., those with acidic properties: Asp and Glu). A conservative (or synonymous) amino acid substitution should not substantially change the structural characteristics of the parent sequence (e.g., a replacement amino acid should not tend to break a helix that occurs in the parent sequence, or disrupt other types of secondary structure that characterizes the parent sequence). Examples of art-recognized polypeptide secondary and tertiary structures are described in *Proteins, Structures and Molecular Principles*, (1984) Creighton (ed.), W. H. Freeman and Company, New York; *Introduction to Protein Structure*, (1991), C. Branden and J. Tooze, Garland Publishing, New York, N.Y.; and Thornton et al. (1991) *Nature* 354: 105; which are incorporated herein by reference).

Native NF-AT$_c$ proteins, fragments thereof, or analogs thereof can be used as reagents in DNA binding assays and/or in vitro transcription assays for identifying agents that interfere with NF-AT function, said agents are thereby identified as candidate drugs which may be used, for example, to block T cell activation or treat T cell lymphocytic leukemias. Typically, in vitro DNA binding assays that measure binding of NF-AT to DNA employ double-stranded DNA that contains an array of one or more NF-AT recognition sites (as defined by specific footprinting of native NF-AT protein). The DNA is typically linked to a solid substrate by any of various means known to those of skill in the art; such linkage may be noncovalent (e.g., binding to a highly charged surface such as Nylon 66) or may be by covalent bonding (e.g., typically by chemical linkage involving a nitrogen position in a nucleotide base, such as diazotization). NF-AT$_c$ polypeptides are typically labeled by incorporation of a radiolabeled amino acid. The labeled NF-AT$_c$ polypeptide, usually reconstituted with an NF-AT nuclear component (e.g., AP-1 activity) to form an NF-AT complex, is contacted with the immobilized DNA under aqueous conditions that permit specific binding in control binding reactions with a binding affinity of about $1 \times 10^6$ M$^{-1}$ or greater (e.g., 10–250 mM NaCl or KCl and 5–100 mM Tris HCl pH 5–9, usually pH 6–8), generally including $Zn^{+2}$ and/or $Mn^{+2}$ and/or $Mg^{+2}$ in the nanomolar to micromolar range (1 nM to 999 $\mu$M). Specificity of binding is typically established by adding unlabeled competitor at various concentrations selected at the discretion of the practitioner. Examples of unlabeled protein competitors include, but are not limited to, the following: unlabeled NF-AT$_c$ polypeptide, bovine serum albumin, and nuclear protein extracts. Binding reactions wherein one or more agents are added are performed in parallel with a control binding reaction that does not include an agent. Agents which inhibit the specific binding of NF-AT$_c$ polypeptides to DNA, as compared to a control reaction, are identified as candidate immunomodulatory drugs. Also, agents which prevent transcriptional modulation by NF-AT in vitro are thereby identified as candidate immunomodulatory drugs.

In addition to NF-AT$_c$ polypeptides consisting only of naturally-occurring amino acids, NF-AT$_c$ peptidomimetics are also provided. Peptide analogs are commonly used in the pharmaceutical industry as non-peptide drugs with properties analogous to those of the template peptide. These types of non-peptide compound are termed "peptide mimetics" or "peptidomimetics" (Fauchere, J. (1986) *Adv. Drug Res.* 15: 29; Veber and Freidinger (1985) TINS p.392; and Evans et al. (1987) *J. Med. Chem* 30: 1229, which are incorporated herein by reference) and are usually developed with the aid of computerized molecular modeling. Peptide mimetics that are structurally similar to therapeutically useful peptides may be used to produce an equivalent therapeutic or prophylactic effect. Generally, peptidomimetics are structurally similar to a paradigm polypeptide (i.e., a polypeptide that has a biological or pharmacological activity), such as human NF-AT$_c$, but have one or more peptide linkages optionally replaced by a linkage selected from the group consisting of —CH$_2$NH—, —CH$_2$S—, —CH$_2$—CH$_2$—, —CH=CH— (cis and trans), —COCH$_2$—, —CH(OH)CH$_2$—, and —CH$_2$SO—, by methods known in the art and further described in the following references: Spatola, A. F. in "*Chemistry and Biochemistry of Amino Acids, Peptides, and Proteins,*" B. Weinstein, eds., Marcel Dekker, New York, p. 267 (1983); Spatola, A. F., Vega Data (March 1983), Vol. 1, Issue 3, "Peptide Backbone Modifications" (general review); Morley, J. S., *Trends Pharm Sci* (1980) pp. 463–468 (general review); Hudson, D. et al., *Int J Pept Prot Res* (1 979) 14:177–185 (—CH$_2$NH—, CH$_2$CH$_2$—); Spatola, A. F. et al., *Life Sci* (1986) 38:1243–1249 (—CH$_2$—S); Hann, M. M., *J. Chem Soc Perkin Trans I* (1982) 307–314 (—CH—CH—, cis and trans); Almquist, R. G. et al., *J Med Chem* (1980) 23:1392–1398 (—COCH$_2$—); Jennings-White, C. et al., *Tetrahedron Lett* (1982) 23:2533 (—COCH$_2$—); Szelke, M. et al., European Appln. EP 45665 (1982) CA: 97:39405 (1982) (—CH(OH)CH$_2$—); Holladay, M. W. et al., *Tetrahedron Lett* (1983) 24:4401–4404 (—C(OH)CH$_2$—); and Hruby, V. J., Life Sci (1982) 31:189–199 (—CH$_2$—S—); each of which is incorporated herein by reference. A particularly preferred non-peptide linkage is —CH$_2$NH—. Such peptide mimetics may have significant advantages over polypeptide embodiments, including, for example: more economical production, greater chemical stability, enhanced pharmacological properties (half-life, absorption, potency, efficacy, etc.), altered specificity (e.g., a broad-spectrum of biological activities), reduced antigenicity, and others. Labeling of peptidomimetics usually involves covalent attachment of one or more labels, directly or through a spacer (e.g., an amide group), to non-interfering position(s) on the peptidomimetic that are predicted by quantitative structure-activity data and/or molecular modeling. Such non-interfering positions generally are positions that do not form direct contacts with the macromolecules(s) (e.g., immunoglobulin superfamily molecules) to which the peptidomimetic binds to produce the therapeutic effect. Derivitization (e.g., labelling) of peptidomimetics should not substantially interfere with the desired biological or pharmacological activity of the peptidomimetic. Peptidomimetics of NF-AT$_c$ may be used as competitive or noncompetitive agonists or antagonists of NF-AT$_c$ function. For example, a NF-AT$_c$ peptidomimetic administered to a stimulated T cell containing NF-AT$_c$ and may compete with the naturally-occurring NF-AT$_c$ and reduce NF-AT activity. Alternatively, an NF-AT$_c$ peptidomimetic administerd to a T cell lacking NF-AT$_c$ may induce T cell activation or the like.

Systematic substitution of one or more amino acids of a consensus sequence with a D-amino acid of the same type (e.g., D-lysine in place of L-lysine) may be used to generate more stable peptides. In addition, constrained peptides (including cyclized peptides) comprising a consensus sequence or a substantially identical consensus sequence variation may be generated by methods known in the art (Rizo and Gierasch (1992) *Ann. Rev. Biochem.* 61: 387, incorporated herein by reference); for example, by adding internal cysteine residues capable of forming intramolecular disulfide bridges which cyclize the peptide.

The amino acid sequences of NF-AT$_c$ polypeptides identified herein will enable those of skill in the art to produce polypeptides corresponding to NF-AT$_c$ peptide sequences and sequence variants thereof Such polypeptides may be produced in prokaryotic or eukaryotic host cells by expression of polynucleotides encoding a NF-AT$_c$ peptide sequence, frequently as part of a larger polypeptide. Alternatively, such peptides may be synthesized by chemical methods. Methods for expression of heterologous proteins in recombinant hosts, chemical synthesis of polypeptides, and in vitro translation are well known in the art and are described further in Maniatis et al., *Molecular Cloning: A Laboratory Manual* (1989), 2nd Ed., Cold Spring Harbor, N.Y.; Berger and Kimmel, *Methods in Enzymology*, Volume 152, *Guide to Molecular Cloning Techniques* (1987), Academic Press, Inc., San Diego, Calif.; Merrifield, J. (1969) *J. Am. Chem. Soc.* 91: 501; Chaiken I. M. (1981) *CRC Crit. Rev. Biochem.* 11: 255; Kaiser et al.(1989) *Science* 243: 187; Merrifield, B. (1986) *Science* 232: 342; Kent, S. B. H. (1988) *Ann. Rev. Biochem.* 57: 957; and Offord, R. E. (1980) *Semisynthetic Proteins*, Wiley Publishing, which are incorporated herein by reference).

Recombinant NF-AT polypeptides can be produced as follows.

The nucleic acid sequences of the present invention capable of ultimately expressing the desired NF-AT$_c$ polypeptides can be formed from a variety of different polynucleotides (genomic or cDNA, RNA, synthetic oligonucleotides, etc.) as well as by a variety of different techniques.

As stated previously, the DNA sequences will be expressed in hosts after the sequences have been operably linked to (i.e., positioned to ensure the functioning of) an expression control sequence. These expression vectors are typically replicable in the host organisms either as episomes or as an integral part of the host chromosomal DNA. Commonly, expression vectors will contain selection markers, e.g., tetracycline resistance or hygromycin resistance, to permit detection and/or selection of those cells transformed with the desired DNA sequences (see, e.g., U.S. Pat. No. 4,704,362, which is incorporated herein by reference).

*E. coli* is one prokaryotic host useful particularly for cloning the DNA sequences of the present invention. Other microbial hosts suitable for use include bacilli, such as *Bacillus subtilis*, and other Enterobacteriaceae, such as Salmonella, Serratia, and various Pseudomonas species. In these prokaryotic hosts, one can also make expression vectors, which will typically contain expression control sequences compatible with the host cell (e.g., an origin of replication). In addition, any number of a variety of well-known promoters will be present, such as the lactose promoter system, a tryptophan (trp) promoter system, a beta-lactamase promoter system, or a promoter system from phage lambda. The promoters will typically control expression, optionally with an operator sequence, and have ribosome binding site sequences and the like, for initiating and completing transcription and translation.

Other microbes, such as yeast, may also be used for expression. Saccharomyces is a preferred host, with suitable vectors having expression control sequences, such as promoters, including 3-phosphoglycerate kinase or other glycolytic enzymes, and an origin of replication, termination sequences and the like as desired.

In addition to microorganisms, mammalian tissue cell culture may also be used to express and produce the polypeptides of the present invention (see, Winnacker, "*From Genes to Clones,*" VCH Publishers, N.Y., N.Y. (1987), which is incorporated herein by reference). Eukaryotic cells are actually preferred, because a number of suitable host cell lines capable of secreting intact human proteins have been developed in the art, and include the CHO cell lines, various COS cell lines, HeLa cells, myeloma cell lines, Jurkat cells, etc. Expression vectors for these cells can include expression control sequences, such as an origin of replication, a promoter, an enhancer (Queen et al. (1986 *Immunol. Rev.* 89: 49, which is incorporated herein by reference), and necessary processing information sites, such as ribosome binding sites, RNA splice sites, polyadenylation sites, and transcriptional terminator sequences. Preferred expression control sequences are promoters derived from immunoglobulin genes, SV40, adenovirus, bovine papillomavirus, and the like. The vectors containing the DNA segments of interest (e.g., polypeptides encoding a NF-AT$_c$ polypeptide) can be transferred into the host cell by well-known methods, which vary depending on the type of cellular host. For example, CaCl transfection is commonly utilized for prokaryotic cells, whereas CaPO$_4$ treatment or electroporation may be used for other cellular hosts. (See, generally, Maniatis, et al., *Molecular Cloning: A Laboratory Manual*, Cold Spring Harbor Press, (1982), which is incorporated herein by reference). Usually, vectors are episomes and are maintained extrachromosomally.

Expression of recombinant NF-ATc protein in cells, particularly cells of the lymphopoietic lineage, may be used to identify and isolate genes that are transcriptionally modulated, either positively or negatively, by the presence of NF-AT$_c$ protein. Such genes are typically initially identified as cDNA clones isolated from subtractive cDNA libraries, wherein RNA isolated from cells expressing recombinant NF-AT and RNA isolated from control cells (i.e., not expressing recombinant NF-ATc) are used to generate the subtractive libraries and screening probes. In such a manner, NF-AT$_c$-dependent genes may be isolated. NFAT-dependent genes (or their regulatory sequences operably linked to a reporter gene) may be used as a component of an in vitro transcription assay employing a NF-AT$_c$ polypeptide as a necessary component for efficient transcription; such transcription assays may be used to screen for agents which inhibit NF-AT$_c$-dependent gene transcription and are thereby identified as candidate immunomodulatory agents.

6. Production and Applications of α-NF-AT$_c$ Antibodies

NF-AT$_c$ and NF-ATn proteins, fragments thereof, or analogs thereof, may be used to immunize an animal for the production of specific antibodies. These antibodies may comprise a polyclonal antiserum or may comprise a monoclonal antibody produced by hybridoma cells. For general methods to prepare antibodies, see *Antibodies: A Laboratory Manual*, (1988) E. Harlow and D. Lane, Cold Spring Harbor Laboratory, Cold Spring Harbor, N.Y., which is incorporated herein by reference.

For example but not for limitation, a recombinantly produced fragment of human NF-AT$_c$ or a purified NF-ATc protein can be injected into a rat or a mouse along with an adjuvant following immunization protocols known to those of skill in the art so as to generate an immune response. Typically, approximately at least 1–50 μg of a NF-AT$_c$ fragment or analog is used for the initial immunization, depending upon the length of the polypeptide. Alternatively or in combination with a recombinantly produced NF-AT$_c$ polypeptide, a chemically synthesized peptide having a NF-AT$_c$ sequence (e.g., peptides exemplified in Table II, infra) may be used as an immunogen to raise antibodies which bind a NF-AT$_c$ protein, such as the native human NF-AT$_c$ polypeptide having the sequence shown essentially in FIG. 12 or the native human NF-AT$_c$ polypeptide isoform. Immunoglobulins which bind the recombinant fragment with a binding affinity of at least $1 \times 10^{-1}$ M$^7$ can be harvested from the immunized animal as an antiserum, and may be further purified by immunoaffinity chromatography or other means. Additionally, spleen cells are harvested from the immunized animal (typically rat or mouse) and fused to myeloma cells to produce a bank of antibody-secreting hybridoma cells. The bank of hybridomas can be screened for clones that secrete immunoglobulins which bind the recombinantly produced NF-AT$_c$ polypeptide (or chemically synthesized NF-AT$_c$ polypeptide) with an affinity of at least $1 \times 10^6$ M$^{-1}$. Animals other than mice and rats may be used to raise antibodies; for example, goats, rabbits, sheep, and chickens may also be employed to raise antibodies reactive with a NF-AT$_c$ protein. Transgenic mice having the capacity to produce substantially human antibodies also may be immunized and used for a source of α-NF-AT$_c$ antiserum and/or for making monoclonal-secreting hybridomas.

Bacteriophage antibody display libraries may also be screened for binding to a NF-AT$_c$ polypeptide, such as a full-length human NF-AT$_c$ protein, a NF-AT$_c$ fragment (e.g., a peptide having a sequence shown in Table II, infra), or a fusion protein comprising a NF-AT$_c$ polypeptide sequence of at least 14 contiguous amino acids as shown in FIG. 12 or a polypeptide sequence of Table II (infra). Combinatorial libraries of antibodies have been generated in bacteriophage lambda expression systems which may be screened as bacteriophage plaques or as colonies of lysogens (Huse et al. (1989) *Science* 246: 1275; Caton and Koprowski (1990) *Proc. Natl. Acad. Sci. (U.S.A.)* 87: 6450; Mullinax et al (1990) *Proc. Natl. Acad. Sci. (U.S.A.)* 87: 8095; Persson et al. (1991) *Proc. Natl. Acad. Sci. (U.S.A.)* 88: 2432). Various embodiments of bacteriophage antibody display libraries and lambda phage expression libraries have been described (Kang et al. (1991) *Proc. Natl. Acad. Sci. (U.S.A.)* 88: 4363; Clackson et al. (1991) *Nature* 352: 624; McCafferty et al (1990) *Nature* 348: 552; Burton et al. (1991) *Proc. Natl. Acad. Sci. (U.S.A.)* 88: 10134; Hoogenboom et al. (1991) *Nucleic Acids Res.* 19: 4133; Chang et al. (1991) *J. Immunol.* 147: 3610; Breitling et al. (1991) *Gene* 104: 147; Marks et al. (1991) *J. Mol. Biol.* 222: 581; Barbas et al. (1992) *Proc. Natl. Acad. Sci. (U.S.A.)* 89: 4457; Hawkins and Winter (1992) *J. Immunol.* 22: 867; Marks et al. (1992) *Biotechnology* 10: 779; Marks et al. (1992) *J. Biol Chem.* 267: 16007; Lowman et al (1991) *Biochemistry* 30: 10832; Lerner et al. (1992) *Science* 258: 1313, incorporated herein by reference). Typically, a bacteriophage antibody display library is screened with a NF-AT$_c$ polypeptide that is immobilized (e.g., by covalent linkage to a chromatography resin to enrich for reactive phage by affinity chromatography) and/or labeled (e.g., to screen plaque or colony lifts).

NF-AT$_c$ polypeptides which are useful as immunogens, for diagnostic detection of α-NF-AT$_c$ antibodies in a sample, for diagnosic detection and quantitation of NF-AT$_c$ protein in a sample (e.g., by standardized competitive ELISA), or for screening a bacteriophage antibody display library, are suitably obtained in substantially pure form, that is, typically about 50 percent (w/w) or more purity, substantially free of interfering proteins and contaminants. Preferably, these polypeptides are isolated or synthesized in a purity of at least 80 percent (w/w) and, more preferably, in at least about 95 percent (w/w) purity, being substantially free of other proteins of humans, mice, or other contaminants. Preferred immunogens comprise at least one NF-AT$_c$ polypeptide sequence shown in Table II, either as a discrete peptide or as part of a fusion polypeptide (e.g., with a β-galactosidase or glutathione S-transferase sequence). NF-AT$_c$ immunogens comprise at least one, typically several of such immunogenic epitopes.

For some applications of these antibodies, such as identifying immunocrossreactive proteins, the desired antiserum or monoclonal antibody(ies) is/are not monospecific. In these instances, it may be preferable to use a synthetic or recombinant fragment of NF-AT$_c$ as an antigen rather than using the entire native protein. More specifically, where the object is to identify immunocrossreactive polypeptides that comprise a particular structural moiety, such as a DNA-binding domain, it is preferable to use as an antigen a fragment corresponding to part or all of a commensurate structural domain in the NF-AT$_c$ protein. Production of recombinant or synthetic fragments having such defined amino- and carboxy-termini is provided by the NF-AT$_c$ sequences shown in FIG. 12, may be accomplished by proteolytic digestion of a purified submit or produced recombinantly.

If an antiserum is raised to a NF-AT$_c$ fusion polypeptide, such as a fusion protein comprising a NF-AT$_c$ immunogenic epitope fused to β-galactosidase or glutathione S-transferase, the antiserum is preferably preadsorbed with the non-NF-AT$_c$ fusion partner (e.g, β-galactosidase or glutathione S-transferase) to deplete the antiserum of antibodies that react (i.e., specifically bind to) the non-NF-AT$_c$ portion of the fusion protein that serves as the immunogen. Monoclonal or polyclonal antibodies which bind to the human and/or murine NF-AT$_c$ protein can be used to detect the presence of human or murine NF-AT$_c$ polypeptides in a sample, such as a Western blot of denatured protein (e.g., a nitrocellulose blot of an SDS-PAGE) obtained from a lymphocyte sample of a patient. Preferably quantitative detection is performed, such as by denistometric scanning and signal integration of a Western blot. The monoclonal or polyclonal antibodies will bind to the denatured NF-AT$_c$ epitopes and may be identified visually or by other optical means with a labeled second antibody or labeled *Staphylococcus aureus* protein A by methods known in the art. Frequently, denatured NF-AT$_c$ will be used as the target antigen so that more epitopes may be available for binding.

TABLE II

Selected Human NF-AT$_c$ Antigen Peptides

-NAIFLTVSREHERVGC- (SEQ ID NO: 25);
-LHGYLENEPLMLQLFIGT- (SEQ ID NO: 26);
-PSTSPRASVTBBSWLG- (SEQ ID NO: 27);
-GPAPRAGGTMKSAEEEHYG- (SEQ ID NO: 28);
-ASAGGHPIVQ- (SEQ ID NO: 29);
-NTRVRLVFRV- (SEQ ID NO: 30);
-AKTDRDLCKPNSLVVEIPPFRN- (SEQ ID NO: 31);
-EVQPKSHHRAHYETEGSR- (SEQ ID NO: 32);
-SPRVSVTDDSWLGNT- (SEQ ID NO: 33);
-SHHRAHYETEGSRGAV- (SEQ ID NO: 34);
-LRNSDIELRKGETDIGR- (SEQ ID NO: 35); and
-TLSLQVASNPWC- (SEQ ID NO: 36).

Such NF-AT$_c$ sequences as shown in Tables II may be used as an immunogenic peptide directly (e.g., to screen bacteriophage antibody display libraries or to immunize a rabbit), or may be conjugated to a carrier macromolecule (e.g., BSA) or may compose part of a fusion protein to be used as an immunogen. A preferred NF-AT$_c$ polypeptide comprises the following amino acids sequences:
-NAIFLTVSREHERVGC-(SEQ ID NO: 25);
-PSTSPRASVTEESWLG-(SEQ ID NO: 27);
-SPRVSVTDDSWLGNT-(SEQ ID NO: 33); and
-SHHRAHYETEGSRGAV-(SEQ ID NO: 34); and may comprise other intervening and/or terminal sequences; generally such polypeptides are less than 1000 amino acids in length, more usually less than about 500 amino acids in length; often spacer peptide sequences or terminal peptide sequences, if present, correspond to naturally occurring polypeptide sequences, generally mammalian polypeptide sequences. One application of the preferred NF-AT$_c$ polypeptide just recited is as a commercial immunogen to raise α-NF-AT$_c$ antibodies in a suitable animal and/or as a commercial immunodiagnostic reagent for quantitative ELISA (e.g., competitive ELISA) or competitive RIA in conjunction with the anti-NF-AT$_c$ antibodies provided by the invention, such as for calibration of standardization of such immunoassays for staging or diagnosis of NF-AT$_c$-expressing lymphocytic leukemias in humans or cell typing or identification of T cells (such as activated T cells and/or activatable T cells). The preferred NF-AT$_c$ polypeptide just recited will find many other uses in addition to serving as an immunogen or immunological reagent. One or more of the above-listed sequences may be incorporated into a fusion protein with a fusion partner such as human serum albumin, GST, etc. For such fusion proteins in excess of 1000 amino acids, deletions in the fusion partner (albumin) moiety may be made to bring the size to about 1000 amino acids or less, if desired.

In some embodiments, it will be desirable to employ a polyvalent NF-AT$_c$ antigen, comprising at least two NF-AT$_c$ immunogenic epitopes in covalent linkage, usually in peptide linkage. Such polyvalent NF-AT$_c$ antigens typically comprise multiple NF-AT$_c$ antigenic peptides from the same species (e.g., human or mouse), but may comprise a mix of antigenic peptides from NF-AT$_c$ proteins of different species (i.e., an interspecies NF-AT$_c$ polyvalent antigen). Frequently, the spatial order of the antigenic peptide sequences in the primary amino acid sequence of a polyvalent antigen occurs in the same orientation as in the naturally occurring NF-AT$_c$ protein (i.e., a first antigenic peptide sequence that is amino-terminal to a second antigenic peptide sequence in a naturally occurring NF-AT$_c$ protein will be amino-terminal to said second antigenic peptide sequence in a polyvalent antigen. Frequently, spacer peptide sequences will be used to link antigenic peptide sequences in a polyvalent antigen, such spacer peptide sequences may be predetermined, random, or psuedorandom sequences. Spacer peptide sequences may correspond to sequences known to be non-immunogenic to the animal which is to be immunized with the polyvalent antigen, such as a sequence to which the animal has been tolerized. Although many examples of such polyvalent antigens may be given, the following embodiment is provided for illustration and not limitation:
-NAIFLTVSREHERVGC-(aa1) (SEQ ID NO: 25)-AKTDRDLCKPNSLVVEIPPFRN-(aa2) (SEQ ID NO: 31)-GILKLRNSDIELRKGETD-(SEQ ID NO: 37)
where (aa1) and (aa2) are peptide spacers of at least one amino acid and less than 1000 amino acids; aa1 is a peptide sequence selected independently from the aa2 peptide sequence; the length of aa1 (which may be composed of multiple different amino acids) is independent of the length of aa2 (which may be composed of multiple different amino acids).

Immunogenic NF-AT$_c$ peptides may be used to immunize an animal to raise anti-NF-AT$_c$ antibodies and/or as a source of spleen cells for making a hybridoma library from which to select hybridoma clones which secrete a monoclonal antibody which binds to a NF-AT$_c$ protein with an affinity of $1 \times 10^7$ M$^{-1}$ or greater, preferably at least $1 \times 10^8$ M$^{-1}$ to $1 \times 10^9$ M$^{-1}$. Such immunogenic NF-AT$_c$ peptides can also be used to screen bacteriophage antibody display libraries directly.

One use of such antibodies is to screen cDNA expression libraries, preferably containing cDNA derived from human or murine mRNA from various tissues, for identifying clones containing cDNA inserts which encode structurally-related, immunocrossreactive proteins, that are candidate novel transcription factors or chromatin proteins. Such screening of cDNA expression libraries is well known in the art, and is further described in Young et al., *Proc. Natl. Acad. Sci. U.S.A.* 80:1194–1198 (1983), which is incorporated herein by reference, as well as other published sources. Another use of such antibodies is to identify and/or purify immunocrossreactive proteins that are structurally or evolutionarily related to the native NF-AT$_c$ protein or to the corresponding NF-AT$_c$ fragment (e.g., functional domain; DNA-binding domain) used to generate the antibody. It is believed that such antibodies will find commercial use as such reagents for research applications, just as other antibodies (and biological reagents—such as restriction enzymes and polymerases) are sold commercially.

Various other uses of such antibodies are to diagnose and/or stage leukemias or other immunological disease states, and for therapeutic application (e.g., as cationized antibodies or by targeted liposomal delivery) to treat neoplasia, hyperimmune function, graft rejection, and the like.

An example of an NF-ATc polypeptide is a polypeptide having the sequence:
MPSTSFPVPSKFPLGPAAAVFGRGETLGPAPRAGGT-MKSAEEEHYGYASSNVSPALPLPTAHSTLPAPCH-NLQTSTPGIIPPADHPSGYGAALDGCPAGYFLSS-GHTRPDGAPAL-ESPRIEITSCLGLYHNNNQFFHDVEVEDVLPSSKR-SPSTATLSLPSLEAYRDPSCLSPASSLSSRSCNSE-ASSYESNYSYPYASPQTSPWQSPCVSPKTTDP-EEGFP
RGLGACTLLGSPQHSPSTSPRASVTEESWLGARSS-RPASPCNKRKYSLNGRQPPYSPHHSPTPSPHGSPR-VSVTDDSWLGNTTQYTSSAIVAAINALTTDSSLDL-GDGVPVKSRKTTLEQPPSVALKVEPVGEDLGSPPP-PADFAPEDYSSFQHIRKGGFCDQYLAVPQHPYQWA-KPKPLSPTSYMSPTLPALDWQLPSHSGPYELRIEV- QPKSHHRAHYETEGSRGAVKASAGGHPIVQLHG-
YLENEPLMLQLFIGTADDRLLRPHAFYQVHRIT-
GKTVSTTSHEAILSNTKVLEIPLLPENSMRAVI-
DCACILKLRNSDIELRKG-
ETDIGRKNTRVRLVFRVHVPQPSGRTLSLQVASNP-
IECSQRSAQELPLVEKQSTDSYPWGGKKMVLSGH
NFLQDSKVIFVEKAPDGHHVWEMEAKT-
DRDLCKPNSLWEIPPFRNQRITSPVHVS-
FYVCNGKRKRSQYQRFTYLPANGNAI-
FLTVSREHERVGCFF (SEQ ID NO: 38)

7. Identification and Isolation of Proteins that Bind NF-AT$_c$

Proteins that bind to NF-AT$_c$, NF-ATn, NF-ATc:NF-ATn and/or a NFAT-DNA complex are potentially important transcriptional regulatory proteins. Such proteins may be targets for novel immunomodulatory agents. These proteins are referred to herein as accessory proteins. Accessory proteins may be isolated by various methods known in the art.

One preferred method of isolating accessory proteins is by contacting a NF-AT$_c$ polypeptide to an antibody that binds the NF-AT$_c$ polypeptide, and isolating resultant immune complexes. These immune complexes may contain accessory proteins bound to the NF-AT$_c$ polypeptide. The accessory proteins may be identified and isolated by denaturing the immune complexes with a denaturing agent and, preferably, a reducing agent. The denatured, and preferably reduced, proteins can be electrophoresed on a polyacrylamide gel. Putative accessory proteins can be identified on the polyacrylamide gel by one or more of various well known methods (e.g., Coomassie staining, Western blotting, silver staining, etc.), and isolated by resection of a portion of the polyacrylamide gel containing the relevant identified polypeptide and elution of the polypeptide from the gel portion.

A putative accessory protein may be identified as an accessory protein by demonstration that the protein binds to NF-AT$_c$ and/or a NFAT-DNA complex. Such binding may be shown in vitro by various means, including, but not limited to, binding assays employing a putative accessory protein that has been renatured subsequent to isolation by a polyacrylamide gel electrophoresis method. Alternatively, binding assays employing recombinant or chemically synthesized putative accessory protein may be used. For example, a putative accessory protein may be isolated and all or part of its amino acid sequence determined by chemical sequencing, such as Edman degradation. The amino acid sequence information may be used to chemically synthesize the putative accessory protein. The amino acid sequence may also be used to produce a recombinant putative accessory protein by: (1) isolating a cDNA clone encoding the putative accessory protein by screening a cDNA library with degenerate oligonucleotide probes according to the amino acid sequence data, (2) expressing the cDNA in a host cell, and (3) isolating the putative accessory protein. Alternatively, a polynucleotide encoding a NF-AT$_c$ polypeptide may be constructed by oligonucleotide synthesis, placed in an expression vector, and expressed in a host cell.

Yeast two-hybrid systems may be used to screen a mammalian (typically human) cDNA expression library, wherein cDNA is fused to a GAL4 DNA binding domain or activator domain, and a NF-AT$_c$ polypeptide sequence is fused to a GAL4 activator domain or DNA binding domain, respectively. Such a yeast two-hybrid system can screen for cDNAs encoding proteins which bind to NF-AT$_c$ sequences. For example, a cDNA library can be produced from mRNA from a human mature T cell line or other suitable cell type. Such a cDNA library cloned in a yeast two-hybrid expression system (Chien et al. (1991) *Proc. Natl. Acad. Sci. (U.S.A.)* 88: 9578 or *Cell* 72: 233) can be used to identify cDNAs which encode proteins that interact with NF-AT$_c$ and thereby produce expression of the GAL4-dependent reporter gene. Polypeptides which interact with NF-AT$_c$ can alos be identified by immunoprecipitation of NF-AT$_c$ with antibody and identification of co-precipitating species. Further, polypeptides that bind NF-AT$_c$ can be identified by screening a peptide library (e.g., a bacteriophage peptide display library, a spatially defined VLSIPS peptide array, and the like) with a NF-AT$_c$ polypeptide. Accessory proteins may also be identified by crosslinking in vivo with bifunctional crosslinking reagents (e.g., dimethylsuberimidate, glutaraldehyde, etc.) and subsequent isolation of crosslinked products that include a Lyar polypeptide. For a general discussion of cross-linking, see Kunkel et al. (1981) *Mol. Cell. Biochem.* 34: 3, which is incorporated herein by reference. Preferably, the bifunctional crosslinking reagent will produce crosslinks which may be reversed under specific conditions after isolation of the crosslinked complex so as to facilitate isolation of the accessory protein from the NF-AT$_c$ polypeptide. Isolation of crosslinked complexes that include a NF-AT$_c$ polypeptide is preferably accomplished by binding an antibody that binds a NF-AT$_c$ polypeptide with an affinity of at least $1\times10^7$ M$^{-1}$ to a population of crosslinked complexes and recovering only those complexes that bind to the antibody with an affinity of at least $1\times10^7$ M$^{-1}$. Polypeptides that are crosslinked to a NF-AT$_c$ polypeptide are identified as accessory proteins.

Screening assays can be developed for identifying candidate immunomodulatory agents as being agents which inhibit binding of NF-AT$_c$ to an accessory protein (e.g. AP-1) under suitable binding conditions.

8. Methods for Identifying Compounds which Affect NF-AT Activity

These methods of screening may involve labeling NF-ATc, or corresponding peptide with any of a myriad of suitable markers, including radiolabels (e. g., $^{125}$I or $^{32}$P), various fluorescent labels and enzymes, (e.g., glutathione-S-transferase and β-galactosidase) . If desired for basic binding assays, one of the components may be immobilized by standard techniques, with the non-immobilized component typically being labeled.

The screening assays of the present invention may utilize isolated or purified forms of these assay components. This refers to nucleic acid segments, polypeptides and the like of the present invention which have been separated from their native environment (e.g., a cytoplasmic or nuclear fraction of a cell, to at least about 10–50% purity. A substantially pure composition includes such compounds that are approaching homogeneity, i.e., about 80–90% pure, preferably 95–99% pure.

While any of the standard pharmaceutical sources of therapeutic candidate agents may be used, a preferred class of agents suitable for use in the screening assays of the present invention are macrolides, particularly those exhibiting a twisted amide peptidyl prolyl bond. See, Schreiber, *Science*, 251, 283–287 (1991) and Banerji et al., *Mol. and Cell. Biol.*, 11, 4074–4087 (1991). These compounds are also preferably capable of binding to and blocking the cystolic receptors FKBP-12 and FKBP-13. See, Jin et al., *Proc. Natl. Acad. Sci., U.S.A.*, 88, 6671–6681 (1991).

Agent screening using the methods of the present invention can be followed by biological testing to determine if the compound has the desired activities in vitro and in vivo. The ultimate therapeutic agent may be administered directly to the host to be treated. Therapeutic formulations may be administered in any conventional dosage formulation. While for the active ingredient may be administered alone, preferably, it is presented as a pharmaceutical formulation. Formulations comprise at least one active ingredient as defined above together with one or more pharmaceutically acceptable carriers thereof. Each carrier must be both pharmaceutically and physiologically acceptable in the sense of being compatible with the other ingredients and not injurious to the patient. Formulations include those suitable for oral, rectal, nasal, or parenteral (including subcutaneous, intramuscular, intravenous and intradermal) administration of a therapeutically effective dose. The formulations may conveniently be presented in unit dosage form and may be prepared by any methods well known in the art of pharmacy.

NF-$AT_c$, NF-$AT_n$ or fragments thereof produced by proteolytic cleavage or recombinantly, can be used as reagents in heterodimerization assays for identifying agents that disrupt NF-AT complex formation, said agents are thereby identified as candidate immunosuppressant drugs. Alternatively, these polypeptides can be used in in vitro assays measuring binding of heterodimeric NF-AT to NF-AT recognition sequences and/or with in vitro transcription assays which measure the ability of NF-AT to enhance the rate of transcription of a sequence linked to at least a minimal promoter and an NF-AT recognition sequence. Typically, in vitro assays that measure binding of NF-AT to DNA employ double-stranded DNA that contains an array of one or more NF-AT recognition sites. The DNA is typically linked to a solid substrate by any of various means known to those of skill in the art; such linkage may be noncovalent (e.g., binding to a highly charged surface such as Nylon 66) or may be by covalent bonding (e.g., typically by chemical linkage involving a nitrogen position in a nucleotide base, such as diazotization) NF-$AT_c$ and/or NF-$AT_n$ are typically labeled by incorporation of a radiolabeled amino acid. The labeled NF-AT protein is contacted with the immobilized DNA under aqueous conditions that permit specific binding in control binding reactions of $1 \times 10^6$ $M^{-1}$ or greater (e.g., 20–150 mM NaCl and 5–100 mM Tris HCl pH 6–8). Specificity of binding is typically established by adding unlabeled competitor at various concentrations selected at the discretion of the practitioner. Examples of unlabeled protein competitors include, but are not limited to, the following: unlabeled NF-$AT_c$ polypeptide, unlabeled NF-$AT_n$, polypeptide, bovine serum albumin, and nuclear protein extracts. Binding reactions wherein one or more agents are added are performed in parallel with a control binding reaction that does not include an agent. Agents which inhibit the specific binding of NF-AT protein to DNA, as compared to a control reaction, are identified as candidate immunosuppressants. Also, agents which prevent in vitro heterodimer formation of NF-AT and/or prevent transcriptional enhancement by NF-AT in vitro are thereby identified as candidate immunosuppressant drugs.

The screening assays of the present invention may utilize isolated, purified, or recombinant forms of these assay components. This refers, e.g., to purified polypeptides and the like of the present invention which have been separated from their native environment (e.g., a cytoplasmic or nuclear fraction of a cell), to at least about 10–50% purity. A substantially pure composition includes such agents that are approaching homogeneity, i.e., about 80–90% pure, preferably 95–99% pure.

8.1. Methods Involving DNA Binding Assays

Candidate immunosuppressants can be identified by NF-AT DNA binding assays. Some candidate immunosuppressants have the ability to inhibit the binding of an assembled NF-AT complex, and, in some instances, of individual NF-AT polypeptides to DNA, particularly where the DNA is double-stranded and has at least one NF-AT recognition site sequence (e.g., as shown in Table I). Various means for detecting specific binding between the NF-AT complex or NF-AT subunit polypeptide and target DNA can be used. Agents which inhibit specific binding of NF-AT complex or NF-AT subunit polypeptide to target DNA are identified as candidate immunosuppressants.

Figure 2:
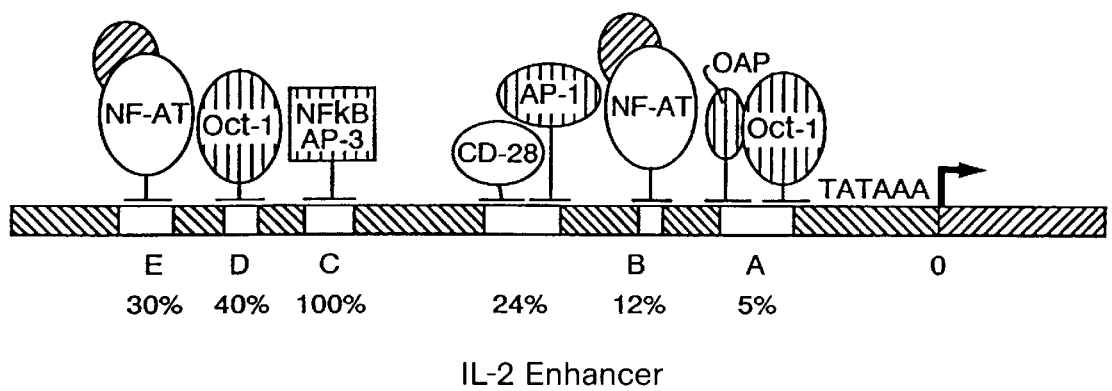
FIG. 2. Diagram of the human IL-2 enhancer from −326 to +47 base pairs. DNase I protected regions are noted by boxes along with the identification of the sites (A–E) and the name(s) of the proteins which complex with these sites. Mutations introduced in the boxed regions drastically reduce IL-2 transcription following T lymphocyte activation and are indicated as percent wild type (full) expression remaining. The arrow identifies the transcriptional start site.
Figure 3:
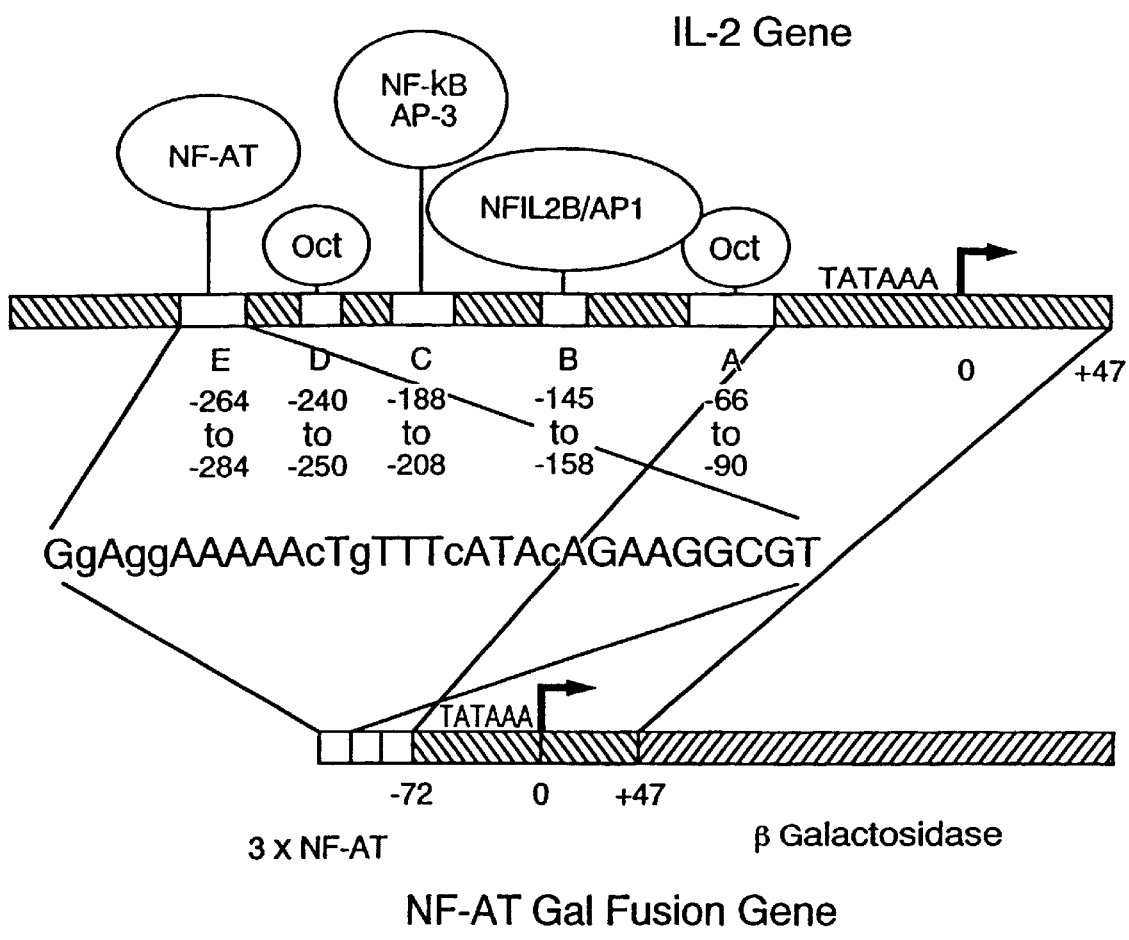
FIG. 3. The diagram shows the NF-AT binding site from the distal element in the interleukin-2 gene. Contact guanine residues are indicated by lower case letters and the construction of binding sites used to measure NF-AT dependent transcriptional activity are shown as an array of three NF-AT binding sites.

Within the interleukin-2 enhancer (FIG. 2), there are two NF-AT sites, a proximal and distal NF-AT site. The sequence of these is shown in detail in FIG. 3. The essential residues judged by methylation interference are indicated by the lower case letters. Elimination of the NF-AT site from the IL-2 enhancer drastically reduces the ability of the enhancer to function. In addition, arrays of the binding site for the NF-AT protein will direct expression of linked sequences (e.g., reporter or toxin genes) to a specific biologic circumstance, notably the activated T lymphocyte wherein transcriptionally active NF-AT complexes are formed.

A distinguishing feature of the NF-AT DNA binding site upstream of the IL-2 gene is its purine-rich binding site 5'-AAGAGGAAAAA-3' (SEQ ID NO:53). DNA sequence comparisons of the promoter/enhancer regions of several genes that respond to T cell activation signals has identified putative NF-AT protein binding sites. Such a comparison suggests that NF-AT or a related family member may bind within the promoter/enhancer regions of other T cell activation dependent genes. Most of these genes are sensitive to immunosuppressants, such as FK506 and cyclosporin. A list of putative NF-AT binding sites follows in Table III:

TABLE III

| Purine Position Core Sequences | Position | Gene |
| --- | --- | --- |
| GAAAGGAGGAAAAACTGTTT (SEQ ID NO: 54) | (−289 to −270) | human IL-2 |
| CCAAAGAGGAAAATTTGTTT (SEQ ID NO: 55) | (−293 to −274) | murine IL-2 |
| CAGAAGAGGAAAAATGAAGG (SEQ ID NO: 56) | (−143 to−124) | human IL-2 |
| TCCAGGAGAAAAAATGCCTC (SEQ ID NO: 57) | (−143 to−124) | human IL-4 |
| AAAACTTGIGAAAATACGTA (SEQ ID NO: 58) | (−71 to −52) | human γ-IFN |
| TAAAGGAGAACACCAGCT (SEQ ID NO: 59) | (−270 to −251) | HIV-LTR |
| GCAGGGTGGGAAAGGCCTTT (SEQ ID NO: 59) | (−241 to −222) | murine GM-CSF |

(Abbreviations: IL-2, interleukin 2; IL-4, interleukin 4; HIV-LTR, human immunodeficiency virus long terminal repeat; GM-CSF, granulocyte-macrophage colony stimulating factor.)

Other NF-AT specific nucleic acid binding sites, usually at least about 10–150 nucleotides (which may be part of a much longer sequence) substantially homologous to these sequences, particularly the NF-AT DNA binding site of the IL-2 enhancer. Ordinarily, such sequences confer NF-AT-dependent transcriptional enhancement on linked (i.e., within 1–75 kb) promoters and are at least about 80% homologous to the NF-AT DNA binding site, preferably in excess of 90% homologous or more, most preferably are identical.

NF-AT binding assays generally take one of two forms: immobilized target DNA can be used to bind labeled NF-AT protein(s), or conversely, immobilized NF-AT protein(s) can be used to bind labeled target DNA. In each case, the labeled macromolecule (protein or DNA) is contacted with the immobolized macromolecule (respectively, DNA or protein) under aqueous conditions that permit specific binding of the NF-AT protein(s) to the target DNA. Particular aqueous conditions may be selected by the practitioner according to conventional methods, including methods employed in DNA-protein footprinting and/or in vitro nuclear run-on transcription (Dunn et al. *J. Biol. Chem.* 263: 10878–10886 (1988), which is incorporated herein by reference). However, preferable embodiments utilize the following buffered aqueous conditions: 20–150 mM NaCl, 5–50 mM Tris HCl, pH 5–8. It is appreciated by those in the art that additions, deletions, modifications (such as pH) and substitutions (such as KCl substituting for NaCl or buffer substitution) may be made to these basic conditions. Modifications can be made to the basic binding reaction conditions so long as specific binding of NF-AT protein(s) to target DNA occurs. Conditions that do not permit specific binding in control reactions (no agent included) are not suitable for use in DNA binding assays.

In embodiments where target DNA is immobilized, preferably double-stranded DNA containing at least one NF-AT recognition site sequence is bonded, either covalently or noncovalently, to a substrate. For example, but not for limitation, DNA can be covalently linked to a diazotized substrate, such as diazotized cellulose, particularly diazophenylthioether cellulose and diazobenzyloxymethyl cellulose (Alwine et al. *Proc. Natl. Acad. Sci.* (*U.S.A.*) 74: 5350 (1977); Reiser et al. *Biochem. Biophys. Res. Commun.* 85: 1104 (1978); Stellwag and Dahlberg, *Nucleic Acids Res.* 8: 299 (1980), which are incorporated herein by reference).

Alternatively, DNA can be covalently linked to a substrate by partial ultraviolet light-induced crosslinking to a Nylon 66 or nitrocellulose substrate (Church and Gilbert, *Proc. Natl. Acad. Sci.* (*U.S.A.*) 81: 1991 (1984), which is incorporated herein by reference). Also, for example and not for limitation, DNA can be noncovalently bound to a Nylon 66 or other highly charged anionic substrate (Berger and Kimmel, Methods in Enzymology, Volume 152, Guide to Molecular Cloning Techniques (1987), Academic Press, Inc., San Diego, Calif.). In some embodiments, it is preferable to use a linker or spacer to reduce potential steric hindrance from the substrate. The immobilized DNA is contacted with labeled NF-AT protein(s), such as NF-AT$_n$, NFAT$_c$, or fragments of NF-AT$_n$ and NF-AT$_c$, or complexes thereof (including [NF-AT$_c$:NF-AT$_n$] heterodimers).

Preferably, at least one NF-AT protein or NF-AT polypeptide species is labeled with a detectable marker. Suitable labeling includes, but is not limited to, radiolabeling by incorporation of a radiolabeled amino acid (e.g., $C^{14}$-labeled leucine, $H^3$-labeled glycine, $S^{35}$-labeled methionine), radiolabeling by post-translational radioiodination with $I^{125}$ or $^{113}$ (e.g., Bolton-Hunter reaction and chloramine T), labeling by post-translational phosphorylation with $P^{32}$ (e.g., phosphorylase and inorganic radiolabeled phosphate, calcineurin), fluorescent labeling by incorporation of a fluorescent label (e.g., fluorescein or rhodamine), or labeling by other conventional methods known in the art. In embodiments where the target DNA is immobilized by linkage to a substrate, at least one species of NF-AT polypeptide is labeled with a detectable marker.

In DNA binding assay embodiments where two or more species of NF-AT subunit polypeptide are used concomitantly, for example a NF-AT$_n$ polypeptide and a NF-AT$_c$ polypeptide, at least one NF-AT subunit polypeptide species is labeled. Additionally, in some embodiments where more than one NF-AT species are employed, it is preferred that different labels are used for each polypeptide, so that binding of individual and/or heterodimeric and/or multimeric NF-AT complexes to target DNA can be distinguished. For example but not limitation, a NF-AT$_c$ polypeptide may be labeled with fluorescein and a NF-AT$_n$ polypeptide may be labeled with a fluorescent marker that fluorescesces with either a different excitation wavelength or emission wavelength, or both. Alternatively, double-label scintillation counting may be used, wherein one NF-AT subunit polypeptide is labeled with one isotope (e.g., $H^3$) and a second NF-AT subunit polypeptide is labeled with a different isotope (e.g., $C^{14}$) that can be distinguished by scintillation counting using discrimination techniques.

Labeled NF-AT subunit polypeptides are contacted with immobilized DNA target under aqueous conditions as described infra. The time and temperature of incubation of a binding reaction may be varied, so long as the selected conditions permit specific binding to occur in a control reaction where no agent is present. Preferable embodiments employ a reaction temperature of at least 20 degrees Centigrade, more preferably 35 to 42 degrees Centigrade, and a time of incubation of at least 15 seconds, although longer incubation periods are preferable so that, in some embodiments, a binding equilibrium is attained. Binding kinetics and the thermodynamic stability of bound NF-AT:DNA complexes determine the latitude available for varying the time, temperature, salt, pH, and other reaction conditions. However, for any particular embodiment, desired binding reaction conditions can be calibrated readily by the practitioner using conventional methods in the art, which may include binding analysis using Scatchard analysis, Hill analysis, and other methods (*Proteins, Structures and Molecular Principles*, (1984) Creighton (ed.), W. H. Freeman and Company, New York).

Specific binding of labeled NF-AT protein to immobilized DNA is determined by including unlabeled competitor protein(s) (e.g., albumin) and/or unlabeled competitor DNA or competitor oligonucleotides. After a binding reaction is completed, labeled NF-AT protein(s) that is specifically bound to immobilized target DNA is detected. For example and not for limitation, after a suitable incubation period for binding, the aqueous phase containing non-immobilized protein and nucleic acid is removed and the substrate containing the target DNA and any labeled protein bound to the DNA is washed with a suitable buffer, optionally containing unlabeled blocking agent(s), and the wash buffer(s) removed. After washing, the amount of detectable label remaining specifically bound to the immobilized DNA is determined (e.g., by optical, enzymatic, autoradiographic, or other radiochemical methods).

In some embodiments, addition of unlabeled blocking agents that inhibit non-specific binding are included. Examples of such blocking agents include, but are not limited to, the following: calf thymus DNA, salmon sperm DNA, yeast RNA, mixed sequence (random or pseudorandom sequence) oligonucleotides of various lengths, bovine serum albumin, nonionic detergents (NP-40, Tween, Triton X-100, etc.), nonfat dry milk proteins, Denhardt's reagent, polyvinylpyrrolidone, Ficoll, and other blocking agents. Practioners may, in their discretion, select blocking agents at suitable concentrations to be included in DNA binding assays; however, reaction conditions are selected so as to permit specific binding between a NF-AT protein and target DNA in a control binding reaction. Blocking agents are included to inhibit nonspecific binding of labeled NF-AT protein to immobilized DNA and/or to inhibit nonspecific binding of labeled DNA to immobilized NF-AT protein.

In embodiments where protein is immobilized, covalent or noncovalent linkage to a substrate may be used. Covalent linkage chemistries include, but are not limited to, well-characterized methods known in the art (Kadonaga and Tijan, *Proc. Natl. Acad. Sci.* (*U.S.A.*) 83: 5889–5893 (1986), which is incorporated herein by reference). One example, not for limitation, is covalent linkage to a substrate derivatized with cyanogen bromide (such as CNBr-derivatized Sepharose 4B). It may be desirable to use a spacer to reduce potential steric hindrance from the substrate. Noncovalent bonding of proteins to a substrate include, but are not limited to, bonding of the protein to a charged surface and binding with specific antibodies. DNA is typically labeled by incorporation of a radiolabeled nucleotide ($H^3$, $C^{14}$, $S^{35}$, $p^{32}$) or a biotinylated nucleotide that can be detected by labeled avidin (e.g., avidin containing a fluorescent marker or enzymatic activity).

NF-AT proteins may exhibit at least three levels of specific binding property: (1) binding to DNA, (2) binding to double-stranded DNA, (3) binding to DNA containing at least one NF-AT recognition site sequence. Each level of binding specificity may be a potential target for candidate immunosuppressants. The DNA assay systems described above may be tailored to assay for each type of binding specificity, if desired.

8.2. Methods for Assaying Heterodimerization

Methods of screening for agents that reduce the binding of the $NF-AT_n$ subunit to the $NF-AT_c$ subunit, and more particularly that prevent the specific heterodimerization of these two subunits, also can identify novel candidate immunosuppressants. Heterodimerization assays involve in vitro binding assays comprising $NF-AT_n$ and $NF-AT_c$ polypeptides (native, fragments, or analogs), wherein test agents can be added to the binding reaction(s) and tested for their ability to inhibit heterodimer formation or reduce the affinity of binding. Agents which interfere with the intermolecular binding between the $NF-AT_n$ subunit (or fragment thereof) and the $NF-AT_c$ subunit (or fragment thereof) are thereby identified as candidate immunosupressants.

These methods of screening may involve labeling $NF-AT_n$, $NF-AT_c$, or corresponding fragments or analogs with any of a myriad of suitable markers, including radiolabels (e.g., $^{125}I$ or $^{32}P$) various fluorescent labels and enzymes, (e.g., glutathione-S-transferase, luciferase, and β-galactosidase). If desired for basic binding assays, one of the components may be immobilized by standard techniques. For example but not for limitation, such immobilization may be effected by linkage to a solid support, such as a chromatographic matrix, or by binding to a charged surface, such as a plastic 96-well microtiter dish.

In one class of embodiments, parallel heterodimerization reactions are conducted, wherein one set of reactions serves as control and at least one other set of reactions include various quantities of agents, mixtures of agents, or biological extracts, that are being tested for the capacity to inhibit pairwise heterodimerization between a $NF-AT_c$ polypeptide (native or fragment) and a $NF-AT_n$ polypeptide (native or fragment). Agents that inhibit heterodimerization relative to the control reaction(s) are thereby identified as candidate immunosuppressants.

Preferred embodiments include heterodimerization assays which use $NF-AT_n$ and $NF-AT_c$ polypeptides which are produced by purification from lymphocytes, particularly T lymphocytes (e.g., Jurkat cells).

8.3. Methods Involving In Vitro Transcription

Methods of screening for agents that inhibit in vitro transcription of template polynucleotides which comprise at least one NF-AT recognition sequence can also be used to identify candidate immunosuppressants. In vitro transcription reactions that are dependent on the presence of functional ($NF-AT_n$:$NF-AT_c$) heterodimer can serve as the basis for such screening assays. Such screening assays employ purified NF-AT, and $NF-AT_n$ subunits, or fragments thereof, which retain the capacity to form functional [$NF-AT_n$:$NF-AT_c$] heterodimers that can interact with NF-AT recognition sequences and enhance in vitro transcription of template polynucleotides comprising linked NF-AT recognition sequences and at least a minimal promoter.

NF-AT-dependent in vitro transcription reactions are defined herein as reactions wherein the addition of an effective amount of NF-AT heterodimer produces a measurable increase in the amount of transcription product(s) and/or increases the accuracy or frequency of transcriptional initiation as compared to a parallel control reaction which does not contain NF-AT. Thus, NF-AT-dependent transcription is that portion of the total transcription that is attributable to the presence of NF-AT. Experimental conditions for in vitro transcription assays may be selected at the discretion of the practitioner according to methods known in the art, or may be done according to Flanagan and Crabtree, *J. Biol. Chem.* 267: 915 (1992), which is incorporated herein by reference.

Agents which inhibit NF-AT-dependent transcription in such in vitro transcription assays are thereby identified as candidate immunosuppressants.

For example and not for limitation, one embodiment of such an in vitro transcription assay employs a transcription template that is a polynucleotide comprising at least one NF-AT recognition site linked to a minimal promoter and some additional downstream transcribed sequences. The in vitro transcription reaction cocktail comprises the template polynucleotide, an $NF-AT_c$ polypeptide species (native or fragment), an $NF-AT_n$ polypeptide species (native or fragment), an RNA polymerase species, preferably human RNA polymerase II, ribonucleotides, and other constituents which are typically included in transcription reaction cocktails. See Heintz and Roeder, Genetic Engineering (1982) Plenum Press, New York. The reactions may be conducted as described in Flanagan and Crabtree, *J. Biol. Chem.* 267: 915 (1992). Where at least one of the ribonucleotide species is radiolabeled, transcription products of the reaction are electrophoresed on a polyacrylamide gel and autoradiography is performed to identify the size and relative amount(s) of transcription product(s). Parallel in vitro transcription reactions are conducted, wherein one set of reactions serves as control and at least one other set of reactions include various quantities of agents, mixtures of agents, or biological extracts that are being tested for the capacity to inhibit (or enhance) in vitro transcription of the template. Agents that inhibit the in vitro transcription relative to the control reaction(s) are thereby identified as candidate immunosuppressants. Agents which enhance transcription may be novel transcription factors or additional protein factors that participate in NF-AT-mediated transcriptional enhancement.

One preferred embodiment of an in vitro transcription assay employs a transcription template comprising the nucleotide sequence which is the 325 nucleotides immediately upstream from the transcriptional start site of the human IL-2 gene.

Another preferred embodiment employs a transcription template that comprises a minimal promoter and a linked tandem array of three NF-AT recognition sequences.

Additionally, preferred embodiments comprise $NF-AT_n$, and $NF-AT_c$ polypeptides that are produced by purification from lymphocytic cells. Biological activity of NF-AT subunit polypeptides can be modified by altering post-translational modifications, such as phosphorylation. In vivo, $Ca^{2-}$ and calmodulin-dependent phosphatase activity, such as calcineurin (Liu et al. *Cell* 66: 807–815 (1991); Friedman and Weissman Cell 66: 799–806 (1991), which are incorporated herein by reference), are involved in modulating biological activity of NF-AT. Therefore, in some embodiments, it is desirable to alter NF-AT polypeptides by post-translational modifications, such as phosphorylation (e.g., with a kinase) or dephosphorylation (e.g., with a phosphorylase).

For example but not for limitation, a NF-AT subunit can be partially phosphorylated by incubation with phosphorylase and inorganic phosphate under conventional reaction conditions known in the art. Alternatively, a NF-AT subunit polypeptide can be partially dephosphorylated by incubation with calf intestinal alkaline phosphatase under conventional reaction conditions. Incubation of NF-AT polypeptides or aggregated NF-AT complex with calcineurin may also be employed. The degree of phosphorylation or dephosphorylation that is achieved with such enzymatic treatments may be determined at the discretion of the practitioner by altering one or more of the following conditions: enzyme concentration, substrate concentration, inorganic phosphate concentration, temperature and duration of incubation, and other reaction parameters known to those of skill in the art.

8.4 Methods for Identifying Compounds which Prevent NF-ATc Nuclear Translocation Methods for screening compounds that prevent the $NF-AT_c$ component from translocating to the nucleus are preferably based on the observation that immunosuppressants, such as FK506 and CsA, inhibit $NF-AT_c$ from entering the nucleus of FK506 and CsA treated T cells. This inhibition may occur by modifying the $NF-AT_c$ component so that $NF-AT_c$ is unable to engage in entry to the nucleus. Thus, an assay typically involves a polypeptide comprising a peptide region of $NF-AT_c$ which becomes modified (e.g., by phophorylation) upon T cell activation, wherein this polypeptide is used to screen compounds which inhibit or enhance the modification of $NF-AT_c$ all in accordance with standard procedures, such as determining whether or not the modification has occurred by performing polyacrylamide gel electrophoresis on samples obtained subsequent to T cell activation and identifying the relative mobility of $NF-AT_c$, by immunoreactivity (e.g., Western blotting) and/or autoradiography (e.g., $^{32}P$ if the modification is phosphorylation).

Alternatively, the nuclear pore of the T cell may be altered to prevent entry of $NF-AT_c$ into the nucleus. Such an assay involves analyzing translocation of $NF-AT_c$, or a corresponding peptide into nuclei that had been previously treated with compounds which alter the nuclear pore of the T cell so that $NF-AT_c$ translocation through or association with the nuclear pore structure fails to occur.

8.5. Methods for Rational Drug Design $NF-AT_c$ polypeptides, especially those portions which form direct contacts in NF-AT complexes, can be used for rational drug design of candidate NFAT-modulating agents (e.g., antineoplastics and immunomodulators). The substantially purified $NF-AT_c$ and the identification of $NF-AT_c$ as a docking partner for AP-1 activities as provided herein permits production of substantially pure NF-AT polypeptide complexes and computational models which can be used for protein X-ray crystallography or other structure analysis methods, such as the DOCK program (Kuntz et al. (1982) *J. Mol. Biol.* 161: 269; Kuntz ID (1992) *Science* 257: 1078) and variants thereof. Potential therapeutic drugs may be designed rationally on the basis of structural information thus provided. In one embodiment, such drugs are designed to prevent formation of a $NF-AT_c$ polypeptide: AP-1 polypeptide complex. Thus, the present invention may be used to design drugs, including drugs with a capacity to inhibit binding of $NF-AT_c$ to form NFAT.

Particularly preferred variants are structural mimetics of a dominant negative $NF-AT_c$ mutants, such as a polypeptide consisting essentially of amino acids 1–418 of FIG. 12 and substantially lacking amino acids carboxy-terminal to residue 418. Such mimetics of dominant-negative mutant polypeptides can have substantial activity as antagonists or partial agonists of NF-AT activation (and hence T cell activation).

8.6. Candidate Immunosuppressants

While any of the standard pharmaceutical sources of therapeutic candidate agents may be used, a preferred class of agents suitable for use in the screening assays of the present invention are macrolides, particularly those exhibiting a twisted amide peptidyl prolyl bond. See, Schreiber, *Science,* 251, 283–287 (1991). These agents are also preferably capable of binding to and blocking the cytosolic receptors FKBP-12 and FKBP-13. See, Jin et al., *Proc. Natl. Acad. Sci., U.S.A.,* 88, 6671–6681 (1991).

Agent screening using the methods of the present invention can be followed by biological testing to determine if the agent has the desired activities in vitro and in vivo. The ultimate therapeutic agent may be administered directly to the host to be treated or administered to explanted cells which may then be returned to the host. Therapeutic formulations may be administered in any conventional dosage formulation. While for the active ingredient may be administered alone, preferably, it is presented as a pharmaceutical formulation. Formulations comprise at least one active ingredient as defined above together with one or more pharmaceutically acceptable carriers thereof. Each carrier must be both pharmaceutically and physiologically acceptable in the sense of being compatible with the other ingredients and not injurious to the patient. Formulations include those suitable for oral, rectal, nasal, or parenteral (including subcutaneous, intramuscular, intravenous and intradermal) administration of a therapeutically effective dose. The formulations may conveniently be presented in unit dosage form and may be prepared by any methods well known in the art of pharmacy.

9. Methods for Forensic Identification

The $NF-AT_c$ polynucleotide sequences of the present invention can be used for forensic identification of individual humans, such as for identification of decedents, determination of paternity, criminal identification, and the like. For example but not limitation, a DNA sample can be obtained from a person or from a cellular sample (e.g., crime scene evidence such as blood, saliva, semen, and the like) and subjected to RFLP analysis, allele-specific PCR, or PCR cloning and sequencing of the amplification product to determine the structure of the $NF-AT_c$ gene region. On the basis of the $NF-AT_c$ gene structure, the individual from which the sample originated will be identified with respect to his/her $NF-AT_c$ genotype. The $NF-AT_c$ genotype may be used alone or in conduction with other genetic markers to conclusively identify an individual or to rule out the individual as a possible perpetrator.

In one embodiment, human genomic DNA samples from a population of individuals (typically at least 50 persons from various racial origins) are individually aliquoted into reaction vessels (e.g., a well on a microtitre plate). Each aliquot is digested (incubated) with one or more restriction enzymes (e.g., EcoRI, HindIII, SmaI, BamHI, SalI, NotI, AccI, ApaI, BglII, XbaI, PstI) under suitable reaction conditions (e.g., see New England Biolabs 1992 catalog). Corresponding digestion products from each individual are loaded separately on an electrophoretic gel (typically agarose), electrophoresed, blotted to a membrane by Southern blotting, and hybridized with a labeled NF-AT$_c$ probe (e.g., a full-length human NF-AT cDNA sequence of FIG. 12). Restriction fragments (bands) which are polymorphic among members of the population are used as a basis to discriminate NF-AT$_c$ genotypes and thereby classify individuals on the basis of their NF-AT$_c$ genotype.

Similar categorization of NF-AT$_c$ genotypes may be performed by sequencing PCR amplification products from a population of individuals and using sequence polymorphisms to identify alleles (genotypes), and thereby identify or classify individuals.

The following examples are offered by way of example and not by way of limitation. Variations and alternate embodiments will be apparent to those of skill in the art.

EXPERIMENTAL EXAMPLES

Example 1

NF-AT is Enriched in Activated T Cells

A DNA binding assay was used to determine the amount of NF-AT present in nuclear extracts from several stimulated and unstimulated cell lines. A radiolabelled oligonucleotide probe corresponding to the NF-AT binding site was hybridized to concentrated nuclear extracts to determine the amount of NF-AT DNA binding activity present.

Procedure

Nuclear extracts were made according to the procedures of Ohlsson and Edlund (Cell 45:35 (1986)). Briefly, nuclei were extracted with 0.3 M (NH$_4$)$_2$SO$_4$ and the fraction that contained the nuclear proteins was precipitated with 0.2 g/ml (NH$_4$)$_2$SO$_4$ and dialyzed for 4 h. at 4° C. The NF-AT binding site of the IL-2 enhancer (−290 and −263) was used as a probe for binding activity. The binding experiment was carried out essentially as described in Shaw, J. P. *Science* 241:202–205 (1988)).

Results

Figure 4:
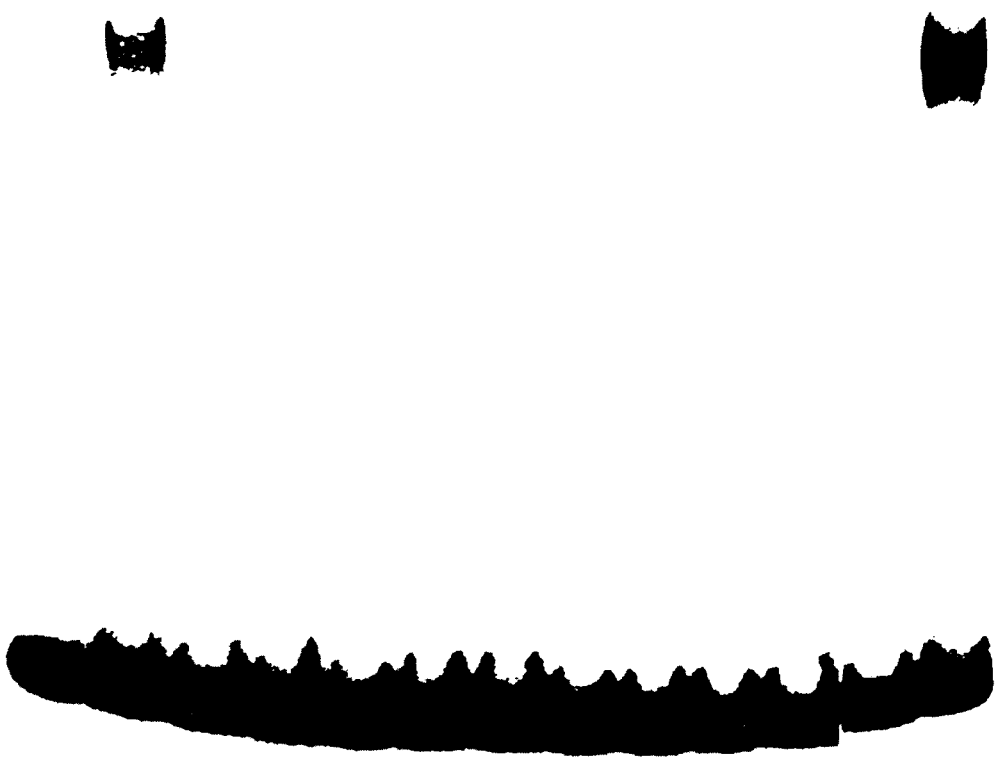
FIG. 4. NF-AT is T cell enriched and is formed following activation of T lymphocytes. Representation of NF-AT in different cell lines. Nuclear extracts from: J, Jurkat cells; K, KB cells (a derivative of HeLa cells); F, Faza cells (a rat liver cell line); H, Hep G2 cells (a human hepatocyte line); T, TEPC murine B-cell line; E, EL-4 murine T cell line; C, C2C12 murine myoblasts. Lanes labelled "+" are the complexes formed with nuclear extracts from cells treated with PHA (2 μg/ml) and PMA (50 ng/ml) for two hours.

As shown in FIG. 4, using a simple gel mobility shift assay, a complex forms with the NF-AT DNA-binding sequence and proteins present in nuclear extracts of activated T cells but not with extracts of non-activated T cells or other types of cells. Only the nuclear extract from the Jurkat T cell line that had been stimulated with the T.cell activating agents PMA and PHA contained detectable amounts of NF-AT-specific DNA binding activity.

Example 2

Protein Synthesis is Required for Production of the Nuclear Component of the NF-AT Complex, While the Cytoplasmic Component is Preexisting To determine whether protein synthesis is required for formation of the nuclear and cytoplasmic components of the NF-AT complex, or whether the proteins are constitutively present in the cells, an NF-AT-specific DNA binding assay was done using NF-AT complex that had been reconstituted from nuclear and cytoplasmic extracts from cells that had been activated in the presence or absence of a protein synthesis inhibitor.

Procedure

NFATZ Jurkat cells were pretreated with 100 μM anisoymycin (Sigma), a protein synthesis inhibitor, for 30 minutes before stimulating the cells. Conditions for activating the cells and preparing nuclear and cytoplasmic extracts are described in Example 3.

Results

Figure 5:
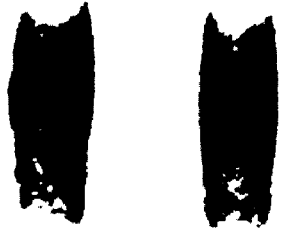
FIG. 5. The nuclear component of the NF-AT complex requires protein synthesis while the cytoplasmic component of NF-AT is pre-existing in T cells. Lanes 1 and 2, gel mobility shift assay using nuclear extracts (10 μg) from stimulated/FK5060-treated (s+F) cells in the presence (+) and absence (−) of 100 μM anisomycin. Lanes 3–6, complementation of nuclear extracts from stimulated/FK506-treated cells (with or without anisomycin pretreatment) with cytoplasmic extracts prepared from nonstimulated cells treated with or without anisomycin. Arrows indicate the mobility of the reconstituted NF-AT DNA binding complex.

As shown in FIG. 5, the protein synthesis inhibitor completely blocked the appearance of the NF-AT complex in activated T cells (Lanes 2,4,6). This demonstrates that the nuclear component of the NF-AT complex is synthesized de novo upon activation of the T cells. In contrast, cytoplasmic extracts prepared from cells grown in the presence or absence of a protein synthesis inhibitor were able to reconstitute the NF-AT complex (Lanes 3–6). Thus, the cytoplasmic component of the NF-AT complex preexists in the cells prior to stimulation, and additional de novo protein synthesis of NF-AT$_c$ is not required.

Since the activation of the interleukin-2 gene as well as most early T cell activation genes also requires protein synthesis, these observations are consistent with a prominent role for NF-AT in early gene activation.

Example 3

NF-AT Can Be Reconstituted from Cytosolic and Nuclear Subunits

A possible interpretation of the data presented in FIG. 5 is that NF-AT is synthesized but sequestered or compartmentalized within the cell and upon breakage of the cells some transcriptionally active NF-AT is formed. To test this hypothesis, the DNA binding ability of NF-AT complexes reconstituted from cytosolic and nuclear extracts from stimulated and non-stimulated T cells, as well as from cells that had been treated with FK506 just prior to stimulation was tested.

Procedure

NFATZ Jurkat cells and JK12/90.1 cells (a gift from N. Shastri) were stimulated for 2 hours with 20 ng/ml PMA and 2 μM ionomycin. To quantitatively block NF-AT formation, FK506 100 ng/ml or CsA (Sandoz) 500 ng/ml were used five minutes prior to the addition of PMA and ionomycin, without any toxic effects to the cells. Nuclear extracts were prepared as described previously with modifications. Cytoplasmic extracts were made from the same cells as the nuclear extracts. Following lysis of the cells with buffer A [10 mM Hepes (pH 7.8), 15 mM Kcl, 2 mM MgCl$_2$, 1 mM DTT, 0.1 mM EDTA, 0.1 mM PMSF] plus 0.05% NP-40, and pelleting of the nuclei, the cytoplasmic fraction was removed and stabilized with 10% (vol/vol) glycerol and 1/10 volume of buffer B [0.3 M Hepes (pH 7.8), 1.4 M Kcl, and 30 mM MgCl$_2$]. The cytoplasmic extract was centrifuged at 200,000 g for 15 minutes. An equal volume of 3 M (NH$_4$)2SO$_4$ (pH 7.9) was added to the supernatant, and precipitated proteins were pelleted at 100,000 g for 10 minutes. The pelleted cytoplasmic proteins were resuspended in buffer C [50 mM Hepes (pH 7.8), 50 mM KCl, 1 mM DTT, 0.1 mM EDTA, 0.1 mM PMSF, 10% (vol/vol) glycerol] and desalted by passage over a P6DG column (BioRad). Protein concentrations were determined using a BioRad protein assay kit. To assess the completeness of the nuclear and cytoplasmic fractionation, we assayed for Oct-I (a constitutive nuclear located DNA binding protein) binding activity and β-galactosidase (cytoplasmic localized) enzyme activity. We found no Oct-1 binding activity in the cytoplasmic fraction and found that β-galactosidase activity is present in the cytosol at 3.7-fold higher concentration than in the nuclear fraction (data not shown). Electrophoretic mobility shift assays were done essentially as described. Fried, M. and D. M. Crothers NAR 9:6505–6526 (1981). Binding reactions were carried out as previously described. Fiering, S. et al. Genes Dev. 4 1823–1834 (1981). Total amount of protein used in each binding reaction was 10 μg. The end-labelled binding site for NF-AT was derived from the human IL-2 enhancer (−285 to −255 bp). The oligonucleotide sequence is 5'-gatcGGAGGAAAAACTGTTCATACAGAAGGGGT-3' (SEQ ID NO: 61). The mutant NF-AT probe essentially differs from the NF-AT oligonucleotide at four contact guanosine residues. The sequence is 5'-gatcAAGAAAGGAGtAAAAAaTtTTTaATACA GAA-3' (SEQ ID NO: 62). Lower case letters indicate mutated residues. Competition with 10 ng of unlabeled oligonucleotide represents a 100- to 200-fold molar excess over labeled probe.

Results

Figure 6A:
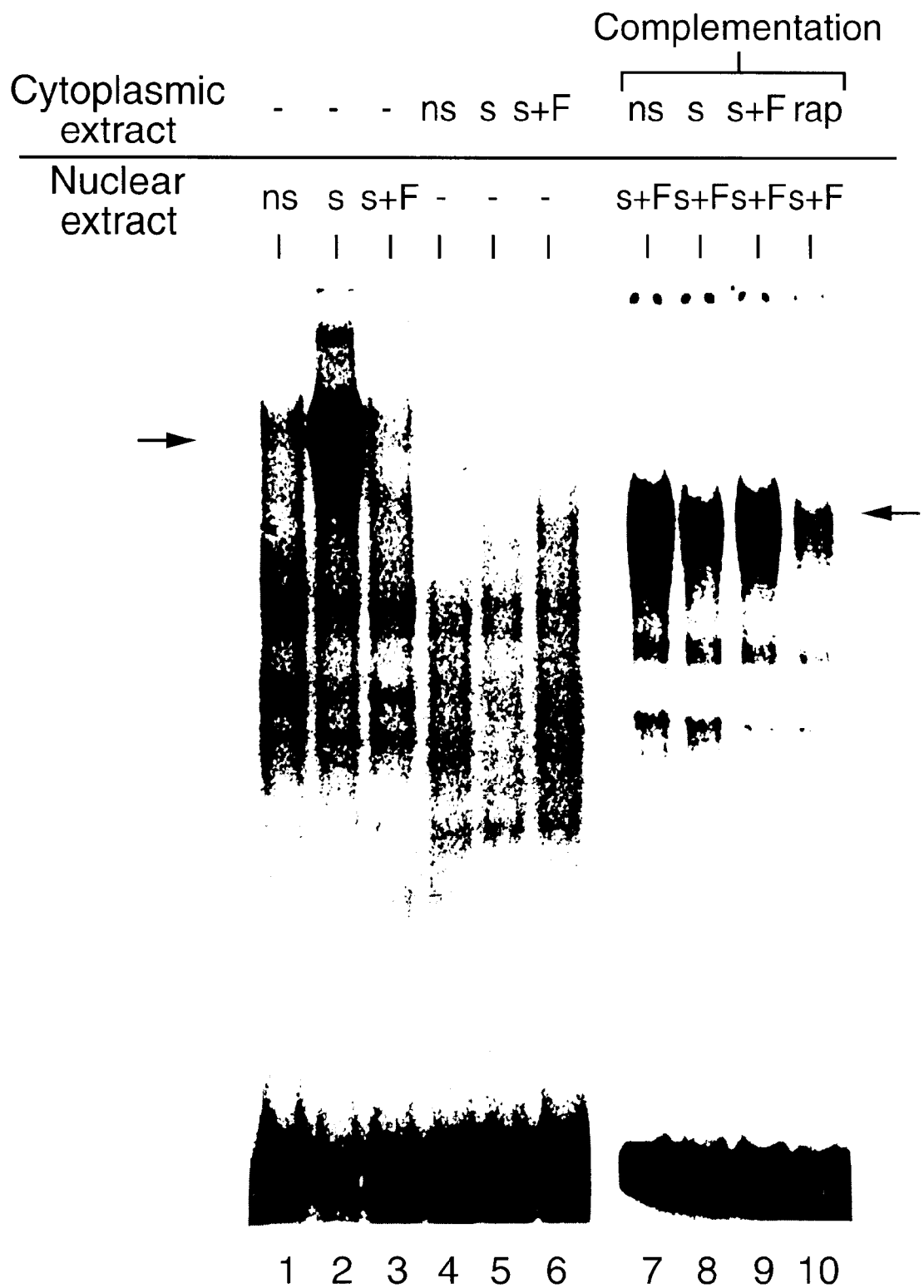
FIG. 6. NF-AT binding activity can be quantitatively reconstituted from nuclear and cytoplasmic fractions of stimulated/FK506- and stimulated/CsA-treated Jurkat cells. (a) In lanes 1–6, nuclear extracts (10 μg) and cytoplasmic extracts (10 μg) from nonstimulated (ns), stimulated (s) with PMA/ionomycin, and stimulated/FK506-treated (s+F) cells were tested for NF-AT binding activity using electrophoretic gel mobility shift assays. In lanes 7–10, NF-AT was reconstituted by mixing nuclear and cytoplasmic extracts. Stimulated/FK506-treated (s+F) nuclear extracts (5 μg) were complemented with cytoplasmic extracts (5 μg) from: lane 7, nonstimulated (ns); lane 8, stimulated (s); lane 9, stimulated/FK506-treated (s+F); and lane 10, stimulated/rapamycin-treated (rap) cells. In all cases arrows indicate the NF-AT protein DNA complex. (b) In lanes 1–3, mixing of nuclear extracts from nonstimulated cells (5 μg) with any cytoplasmic extracts (5 μg) fails to reconstitute NF-AT binding. In lanes, 4–9, reconstituted NF-AT binding activity demonstrates DNA binding specificity: nuclear extracts (5 μg) from stimulated/FK506-treated cells (s+F) were mixed with cytoplasmic extracts (5 μg) and competition was carried out with 10 ng of unlabeled NF-AT or mutant NF-AT oligonucleotide. (c) The effect of FK506 was tested on a murine T cell hybridoma, JK12/90.1 (Karttunen et al. (1991) *PNAS* 88:3972). In lanes 1–3, nuclear extracts (10 μg) from nonstimulated/FK506-treated (s+F) Jurkat cells were tested for NF-AT binding activity. Lane 6 shows NF-AT binding in nuclear extracts from stimulated/FK506treated (s+F) JK12/

In the nuclear extracts prepared from stimulated/FK506-treated cells, NF-AT binding activity is reduced substantially and is not observed in the cytoplasmic fractions (FIG. 6A, lanes 3 and 6). Remarkably, binding activity was completely reconstituted by mixing nuclear extracts from stimulated/FK506-treated cells together with cytoplasmic fractions from nonstimulated, or stimulated/FK506-treated cells, neither of which have NF-AT binding activity (FIG. 6A, lanes 7 and 9). Although the mobility of the reconstituted DNA-protein complex is slightly faster than the characteristic mobility of the NF-AT complex, DNA binding specificity is identical. (FIG. 6B, lanes 4–9). Nuclear extracts from nonstimulated cells are not complemented by any of the cytoplasmic extracts (FIG. 6B lanes 1–3) suggesting that stimulation of the cells is essential for synthesis of the nuclear component of NF-AT.

While cytoplasmic extracts from nonstimulated and stimulated/FK506-treated cells can reconstitute the NF-AT complex, cytoplasmic extracts from stimulated cells show only partial reconstitution of NF-AT binding activity (FIG. 6A, lane 8) implying that the cytoplasmic component of NF-AT preexists in nonstimulated cytoplasmic extracts and is translocated to the nucleus following stimulation in the absence of FK506.

We used rapamycin as a control for non-specific effects of FK506. Rapamycin is a structural analog of FK506, and like FK506, contains a structural mimic of a twisted leucyl-prolyl amide bond, binds FK-BP, and inhibits its isomerase activity (Bierer et al. (1990) Science 250:556; Bierer et al. (1990) PNAS (U.S.A.) 87:9231; and Rosen et al. (1990) Science 248:863). Despite the fact that rapamycin inhibits isomerase activity, it antagonizes the actions of FK506 on NF-AT-directed transcription, IL-2 gene activation, T cell activation, and programmed cell death (Bierer et al. (1990) PNAS 87:9231; Dumont et al. (1985) J. Immunol. 134:1599; and Dumont et al. (1990) J. Immunol. 144:1418). Rapamycin did not block translocation of the cytoplasmic component of NF-AT to the nucleus following activation (FIG. 6A, lane 10). This is consistent with its failure to block NF-AT directed transcription (Mattila et al., supra).

Figure 6C:
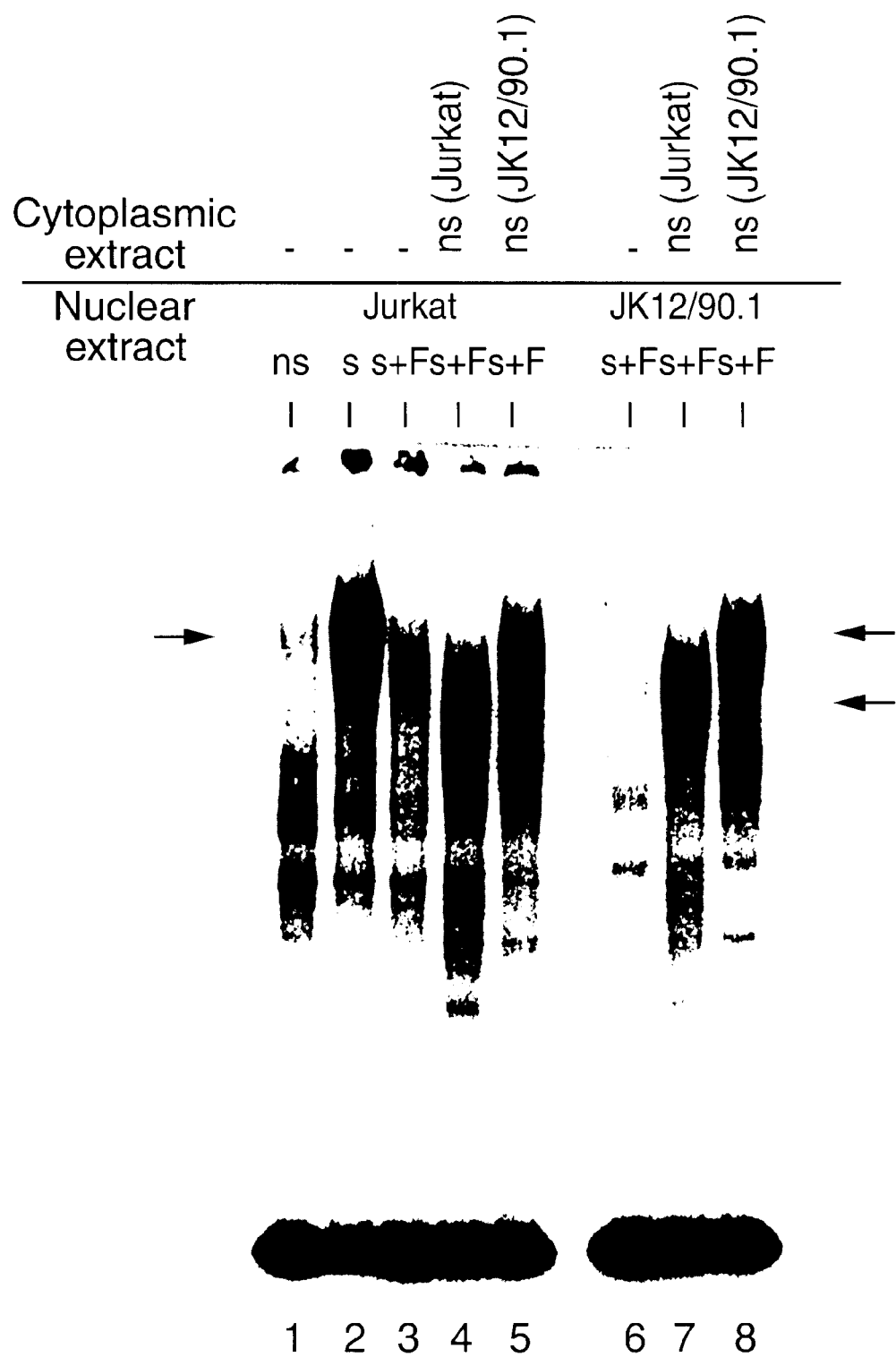
Figure 6D:
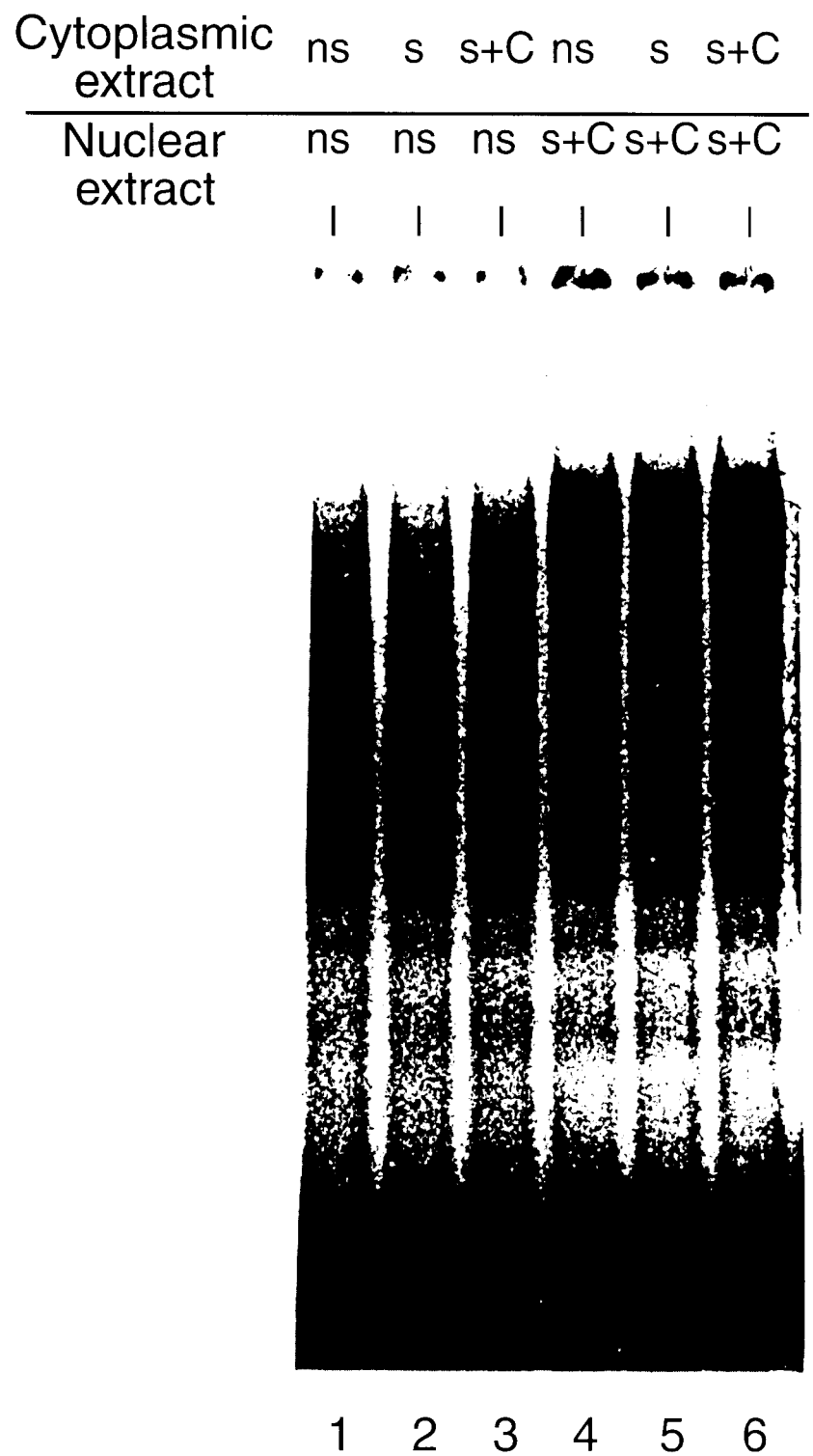

To determine if impaired nuclear import is also a property of the immunosuppressive prolyl isomerase inhibitor CsA, we teeted the effects of CsA. The biological effects of FK506 and CsA on the immune response are essentially identical (Karrtunen et al. (1991) PNAS 88:3872). CsA completely blocks NF-AT directed transcription in T cells and extracts of cells stimulated in the presence of CsA contain less NF-AT binding activity than stimulated controls (Emmel et al. (1989) Science 246:1617). Accordingly, mixing nuclear extracts from stimulated CsA-treated cells with cytoplasmic extracts from the sane cells or nonstimulated cells reconstitutes NF-AT binding activity (FIG. 6C, lanes 4–6). Again, nonstimulated nuclear extracts are not able to be complemented by any cytoplasmic extract (FIG. 6C, lanes 1–3). Thus, these results suggest that CsA and FK506 both block the translocation of a pre-existing cytoplasmic component which constitutes part of the NF-AT DNA binding complex.

Example 4

The Cytosolic Form of NF-AT (NF-AT$_c$) is Selectively Expressed in T Cells

Despite the fact that the actions of CsA and FK506 are tissue specific, their binding proteins are ubiquitous (Koletsky et al. (1986) J. Immunol. 137: 1056; Kincaid et al. (1987) Nature 330:176; Sieklerkaet al. (1989) Nature 341:755; and Harding et al. (1989) Nature 341: 758). This apparent quandary could be rationalized if the drug-isomerase complex acted on a T cell specific molecule. To determine whether the components of the NF-AT complex are found in cell types other than T cells, we tested whether nuclear or cytoplasmic extracts of HeLa cells can be used to reconstitute NF-AT complex alone or in conjunction with extracts from Jurkat cells.

Procedure

HeLa S3 cells were grown in spinner flasks at 37° C. in S-MEM (Gibco-BRL) supplemented with 5% fetal calf serum, penicillin (100 U/ml), and 100 μg/ml of streptomycin. HeLa S3 were stimulated, nuclear and cytoplasmic extracts were prepared, and gel mobility shift assays were carried out under conditions identical to those described in FIG. 6.

Results

Figure 7A:
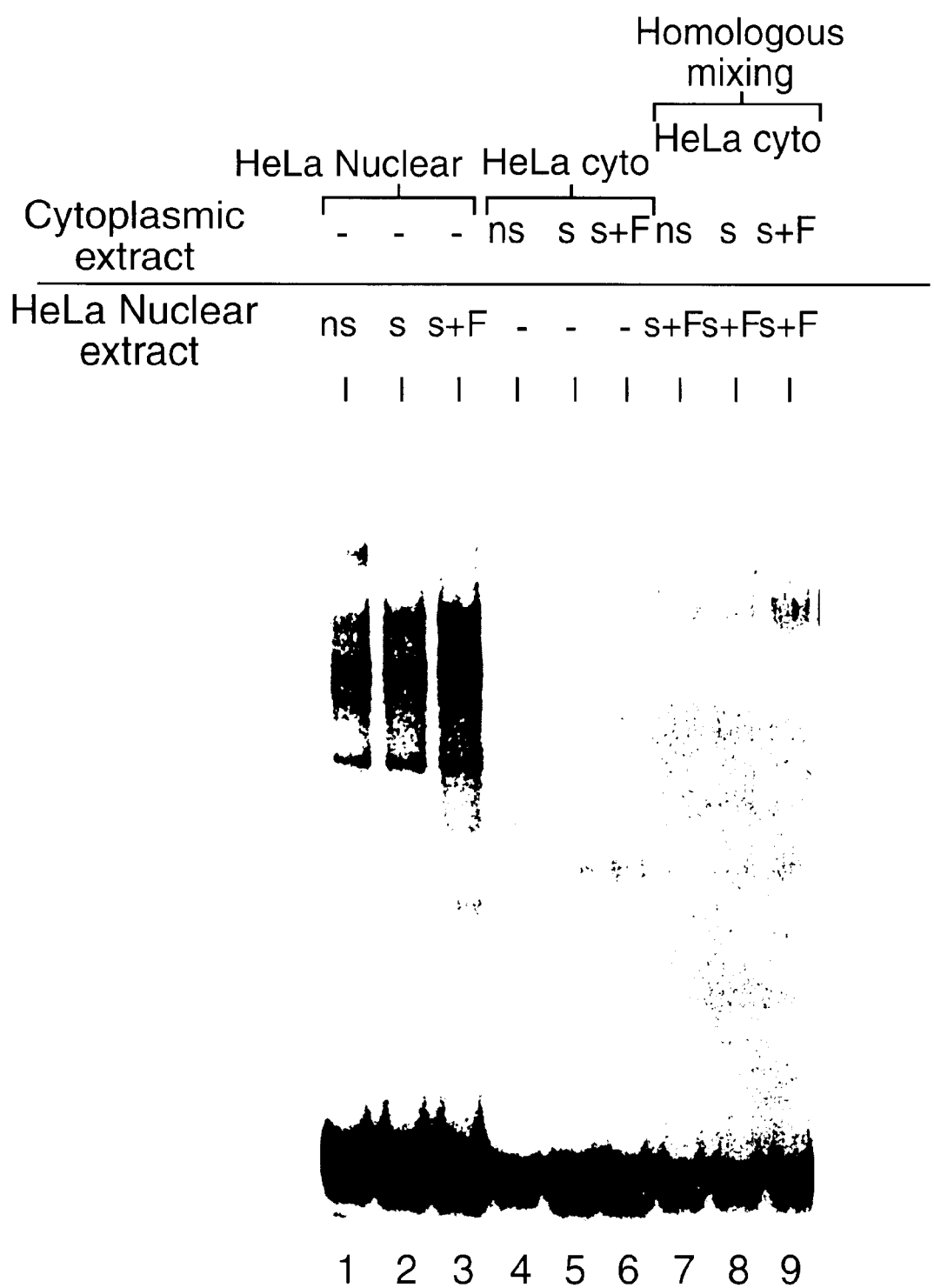
Figure 7B:
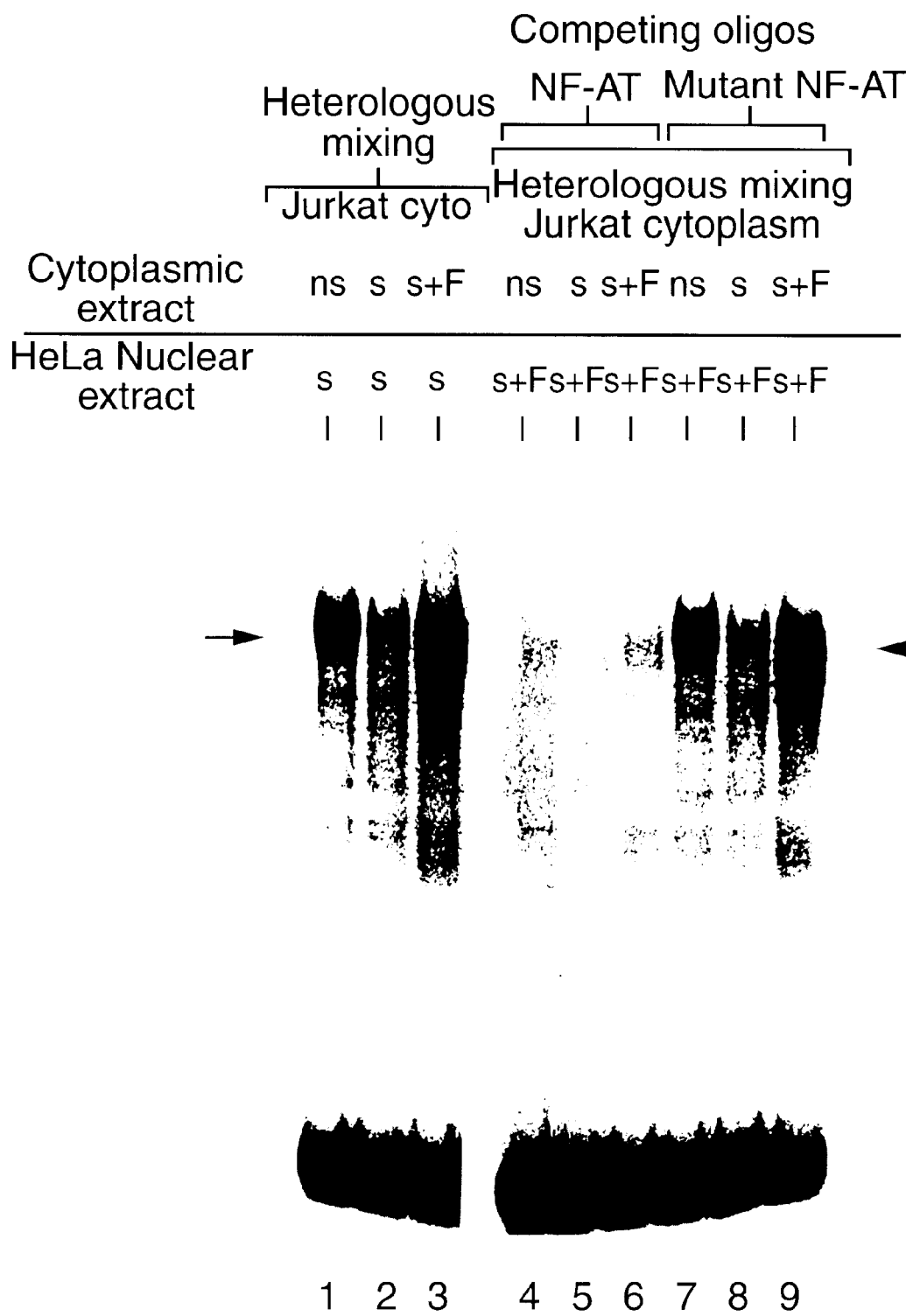

HeLa cytoplasmic extracts do not contain NF-AT and homologous mixing of nuclear and cytoplasmic extracts do not contain NF-AT and homologous mixing of nuclear and cytoplasmic extracts from HeLa cells failed to reconstitute NF-AT binding activity (FIG. 7A, lanes 1–9). In contrast, heterologous mixing of Jurkat cytoplasmic extracts with nuclear extracts from HeLa cells reconstituted NF-AT binding activity (FIG. 7B, lanes 1–3). Furthermore, the reconstituted NF-AT binding activity is specific as demonstrated by oligonucleotide competition (FIG. 7B, lanes 4–9). These results suggest that the oligonucleotide competition (FIG. 7B, lanes 4–9). These results suggest that the nuclear component of NF-AT is present in HeLa cells. In contrast, HeLa cell cytoplasmic extracts cannot reconstitute NF-AT binding activity when mixed with nuclear extracts from stimulated/FK506-treated Jurkat cells (FIG. 7C, lanes 1–3) implying that the cytoplasmic component is T cell specific while the nuclear component of NF-AT is not.

Example 5

Nuclear Import of the Cytosolic Component Can Be Induced with Ionomycin While Synthesis of the Nuclear Component Requires only PMA A unifying feature of the actions of FK506 and CsA is that they inhibit processes which require $Ca^{2+}$ mobilization (Mattila et al. (1990) EMBO J. 9:4425; Kay et al. (1989) Cell. Immun. 124:175; Cirillo et al. (1990) J. Immunol. 144:3891; Gunter et al. (1989) J. Immunol. 142:3286). Induction of NF-AT binding and transcriptional activity requires physiologic stimuli that are believed to be mimicked by agents that increase intracellular $Ca^{2+}$ and activate protein kinase C (PKC) (Shaw et al. (1988) Science 241:202).

To examine the requirements for induction of the nuclear and cytoplasmic subunits of NF-AT, extracts were prepared from cells stimulated with either PMA alone or ionomycin alone and tested for their ability to reconstitute DNA-binding activity.

Procedure

Gel mobility shifts and preparation of nuclear and cytoplasmic extracts were carried out as described in Example 3.

Results

Cytosolic extracts from ionomycin-treated cells show less ability to reconstitute DNA binding when added to nuclear extracts of stimulated FK506-treated cells than either cytosolic extracts from non-stimulated cells, cytosolic extracts from PMA-stimulated cells or cytosolic extracts from cells stimulated with both PMA and ionomycin (FIG. 8). FK506 treatment did not inhibit PMA/ionomycin-stimulated cells from synthesizing the nuclear component of NF-AT (FIG. 8, Lanes 9–12). Furthermore, mixing cytoplasmic extracts from PMA-stimulated or ionomycin-stimulated cells with nuclear extracts from stimulated/FK506-treated cells fail to reconstitute NF-AT DNA-binding activity (FIG. 8, Lanes 4 and 7), suggesting that the preexisting cytoplasmic subunit translocated to the nucleus. Thus, CsA and FK506 appear to inhibit the $Ca^{2+}$-dependent translocation of the cytoplasmic component of NF-AT.

Example 6

FK506 Does Not Inhibit NF-AT-dependent Transcription In vitro

The effect of FK506 on the ability of NF-AT to direct transcription was tested by preparing nuclear extracts from stimulated or stimulated/FK506-treated cells and testing their ability to transcribe a G-less cassette in which transcription was dependent upon three NF-AT sites located within a synthetic promoter.

Procedure

Promoter constructs, nuclear extracts and transcription reactions were prepared as described. NFATZ Jurkat cells, derived from a human T cell leukemia, were stimulated with 20 µg/ml PMA (Sigma), 2 µM ionomycin (Calbiochem) for 2 hours. FK506 was used at 10 ng/ml and added five minutes prior to the addition of PMA and ionomycin. Ribonuclease protection assay of the NF-AT/lacZ mRNA was carried out as previously described. Transcription was quantitated using a radioanalytic imaging system (AMBIS).

Using the human Jurkat T cell line (Wiskocii et al. (1985) *J. Immunol.* 1599), we developed an activation-dependent, T cell specific in vitro transcription system which faithfully reflects the complex requirements for L-2 transcription and more generally T cell activation.

In vitro Transcription Protocol

Procedure (i) Cell Culture and Stimulation Conditions

Jurkat cells were grown in RPMI 1640 without L-glutamine, 8% fetal calf serum (FCS) (Irvine Scientific), with penicillin (100 units/ml) and streptomycin sulfate (100 µg/ml) at 5% $CO_2$ concentrations. Cells were split 1:3 thirty-six hours before stimulation. The morning of the stimulation, the Jurkat cells ($1\times10^6$ cells/ml) were centrifuged at 3500 rpm (2000×g), in a GS-3 rotor for 10 minutes and then resuspended in fresh media to a concentration of $2\times10^6$ cells/ml. In general, 2 µM ionomycin (calbiochem) and 20 ng/ml PMA (Sigma) were used to stimulate the cells. During the 2 hour stimulation, the cells were constantly shaking to prevent the layering of cells on the bottom of the flask.

Hela S3 cells were grown in S-MEM (Gibco) with 8% GCS, with penicillin (100 units/ml) and streptomycin sulfate (100 µg/ml) and 2 mM L-glutamine. Hela S3 were stimulated with 20 ng/ml PMA and 2 µM ionomycin.

(ii) Plasmid Construction

The IL-2 G-less plasmid was constructed by fusing the IL-2 enhancer (−326 to +24) to a 377 base pair (bp) G-less cassette generously provided by R. Roeder (Sawadogo and Roeder, 1985) using polymerase chain reaction overlap extension techniques (Horton, R. M. et al. *Gene* 77:61–68 1989; Ho, S. N., et al. *Gene* 77:51–59 1989). The IL-2 enhancer G-less cassette contained on a Xho I-Bam HI fragment was inserted into a pUC derivative containing an Xho I site in the polylinker. To avoid PCR artifacts the entire IL-2 enhancer G-less cassette was sequenced. The total size of the IL-2 enhancer G-less transcript is 401 nucleotides (nt). The NF-AT multimer which contains 3 NFAT binding sites (−286 to −257) and NF-IL-2A multimer which contains 4 NF-IL-2A binding sites (−94 to −65) G-less constructs were made by digesting pE3.1 and pA4.1 (Durand et al. 1988) with Asp 718 and Ban HI, respectively, and ligating the fragments into an Asp 718-Ban El digested τ-fibrinogen G-less cassette construct. τ-fibrinogen G-less was constructed by fusing −54 to +1 of the τ-fibrinogen promoter (Crabtree, G. R. and Kant, J. A. Cell 31:159–166 1982; Durand et al. 1987) to the 377 bp G-less cassette using PCR overlap extension techniques. All regions of the construct made using PCR technology were sequenced to avoid any point mutations using Sequenase DNA sequencing kit (U.S. Biochemical). The τ-fibrinogen promoter is a minimal promoter containing only a Spl binding and TATA box. Between +1 of the τ-fibrinogen promoter and the G-less cassette a Ssp I restriction enzyme site was inserted. Both the ARRE-2 and ARRE-1 G-less constructs generate 383 nt transcripts.

The HNF-1 (hepatocyte nuclear factor 1) G-less plasmid was constructed by inserting tandemly linked NF-I binding sites from Rat β-fibrinogen promoter (−77 to −65) (Courtois et al. 1987) into Xho-Sal polylinker sites in τ-fibrinogen G-less construct. The adenovirus major late promoter (AdMLP) G-less construct was a generous gift of Drs. M. Sawadoga and R. Roeder. Total size of the AdMLP G-less transcript is 280 nt.

(iii) Preparation of Nuclear Extracts

Jurkat and liver in vitro transcription nuclear extracts were essentially made as described by Gorski et al. (Gorski et al. 1986; Maire et al. 1989) with some exceptions. First, the cells were broken in 1.5 M sucrose-glycerol solution to reduce the amount of frictional heat generated during cell lysis. Second 0.5% (vol/vol) nonfat dry milk was added to the homogenization buffer as had been previously described (Maire et al. 1989). Third, the Jurkat nuclei were fractionated on only one 2.0 M sucrose pad preceding salt extraction. Briefly, all manipulations were performed in the cold, and all solutions, tubes, and centrifuges were chilled to 4° C. Protease inhibitors, antipain (1 µg/ml), leupeptin (1 µg/ml), 0.1 mM phenylmethylsulfonyl fluoride (PMSF) and 0.1 mM benzamidine, were added to all buffers except the dialysis buffer. One mM dithiothreitol was added to all buffers. Following stimulation in the case for Jurkats, the cells ($10^9$) were centrifuged in a GS-3 rotor, 3500 rpm (2000×g), for 10 minutes. The media was poured off and the cells were rinsed with 40 mls of phosphate buffered saline. Resuspended pellets were then centrifuged 1000 rpm (200×g), 10 minutes in a \Beckman GPR tabletop centrifuge. The cell pellet was resuspended in 10 ml of homogenization buffer (10 mM Hepes [pH 7.6]25 mM KCl, 0.15 mM spermine, 0.5 mM spermidine, 1 mM EDTA, 1.25 M sucrose, 10% glycerol (vol/vol), 0.5% nonfat dry milk (vol/vol). An aqueous 0.1 g/ml nonfat dry milk solution was centrifuged for 10 minutes in a SS-34 rotor at 1000 rpm (11950×g) to remove undissolved milk solids before adding to any solution.

The cells were dounced (Teflon-glass homogenizer) until broken using a ½ hp drill press (Jet Tools Inc) at high speed. Cells were checked for lysis. Generally, greater than 80% of the cells were lysed. Following lysis, 46 mls of 2M sucrose homogenization buffer (10 mM Hepes (pH 7.6], 25 mM KCl, 0.15 mM spermine, 0.5 mM spermidine, 1 mM EDTA, 2M sucrose, 10% glycerol (vol/vol), 0.5% nonfat dry milk (vol/vol) were added to the dounced cells. The homogenized cells (28 mls) were layered on to 10 ml sucrose pads (10 mM Hepes (pH 7.6), 25 mM KCl, 0.15 mM spermine, 0.5 mM spermidine, 1 mM EDTA, 2M sucrose, 10% glycerol (vol/vol) and centrifuged at 24,000 rpm for 60 minutes in a SW 28 rotor (103,000×g).

The pelleted nuclei were resuspended in a total of 6 ml of nuclear lysis buffer (10 mM Hepes [pH 7.6], 100 mM KCl, 3 mM $MgC_2$, 0.1 nM EDTA, 10% glycerol (vol/vol).) One ninth volume of 3M $(NH_4)_2SO_4$ pH 7.9 was added and mixed constantly for 30 minutes. The viscous lysate was centrifuge 40,000 rpm, 60 minutes, in a Ti 50 rotor (150,000×g) to pellet the chromatin.

Following centrifugation, the tubes were quickly removed and the supernatant transferred to another tube before the pelleted chromatin began to reswell. To the supernatant, 0.3 grams of solid $(NH_4)_2SO_4$ per ml were added. The tube was gently mixed for 10 minutes or until all the $(NH_4)_2SO_4$ had gone into solution. The tubes were placed on ice for 40 minutes and gently mixed every 10 minutes. The precipitated proteins were then centrifuged for 15–20 minutes, 40,000 rpm, in a Ti 50 rotor (150,000×g) . At this point, the pellet was immediately resuspended in dialysis buffer (25 mM Hepes [pH 7.6], 40 mM KCl, 0.1 mM EDTA, 10% glycerol (vol/vol).) Protein extracts from 1×10⁹ Jurkat cells were resuspended in 200–300 μl of dialysis buffer resulting in a final protein concentration of 10 mg/ml. Extracts were dialyzed twice for 2 hours in the cold against 100 volumes of dialysis buffer. During dialysis a precipitate forms that at the end of dialysis was removed by centrifugation at a microfuge (Brinkman Instruments) at a setting of 14 for 5 minutes. Protein concentrations were determined with a Bio-Rad protein assay kit using BSA as a standard. Protein extracts were frozen in small aliquots on dry ice and immediately stored in liquid nitrogen.

HeLa S3 nuclear extracts were made as previously described (Shapiro, D. J. et al. *DNA* 7:44–45 1988).

(iv) Transcription Reactions

In general, transcription reactions (20 μl) contained 40 μg/ml of circular DNA template [400 ng of the test construct, 40 ng of the AdMLP G-less construct, and 360 ng of poly dI-dC (Pharmacia)] and between 3–5 mg/ml nuclear protein extract in a buffer containing 25 mM Hepes (pH 7.6), 50 mM KCl, 6 mM MgCl2, 0.6 mM each of ATP and CTP, 7 μM UTP, 7 μCi [a-$^{32}$P] UTP (Amersham, 400 Ci/mmole), 0.5 mM 3'-O-methyl GTP (Pharmacia), 150 units of RNase T1 (BRL), 12 unites of RNase inhibitor (Amersham) and 12% glycerol (vol/vol). EDTA and DTT were contributed by the extract. Transcription reactions using liver or HeLa nuclear extracts contained 40 μg/ml of circular DNA templates (400 ng of the test construct and 400 ng of the AdMLP). All other reaction conditions were kept constant. The reactions were incubated for 45 minutes at 30° C. The transcription reactions were terminated by adding 280 ,ul of stop buffer (50 mM Tris-HCl [pH 7.6], 1% SDS, 5 mM EDTA) and were extracted two times with phenol and one time with chloroform. The RNA was precipitated with 15 μg of glycogen, 0.3M sodium acetate (pH 5.2) and 2.5 volumes of ETOH.

The pellets were rinsed with 70% ethanol, air dried, and resuspended in 10 μl of loading dye (90% formamide, 0.01% xylene cyanol, and 0.01% bromophenol blue in 1×TBE.) The transcripts were analyzed on 6% denaturing polyacrylamide gels. In general, the gels were exposed overnight at room temperature using XAR-5 (Kodak) x-ray film. Normalized fold induction is calculated by normalizing the amount of transcription from the test G-less construct to that observed from the AdMLP G-less construct and then dividing the amount of test G-less transcription from stimulated nuclear extracts by the amount of test G-less transcription from nonstimulated nuclear extracts. Autoradiograms were quantitated using an Ambis radioanalytic imaging system (Ambis Systems, San Diego, Calif.).

Results

Figure 9A:
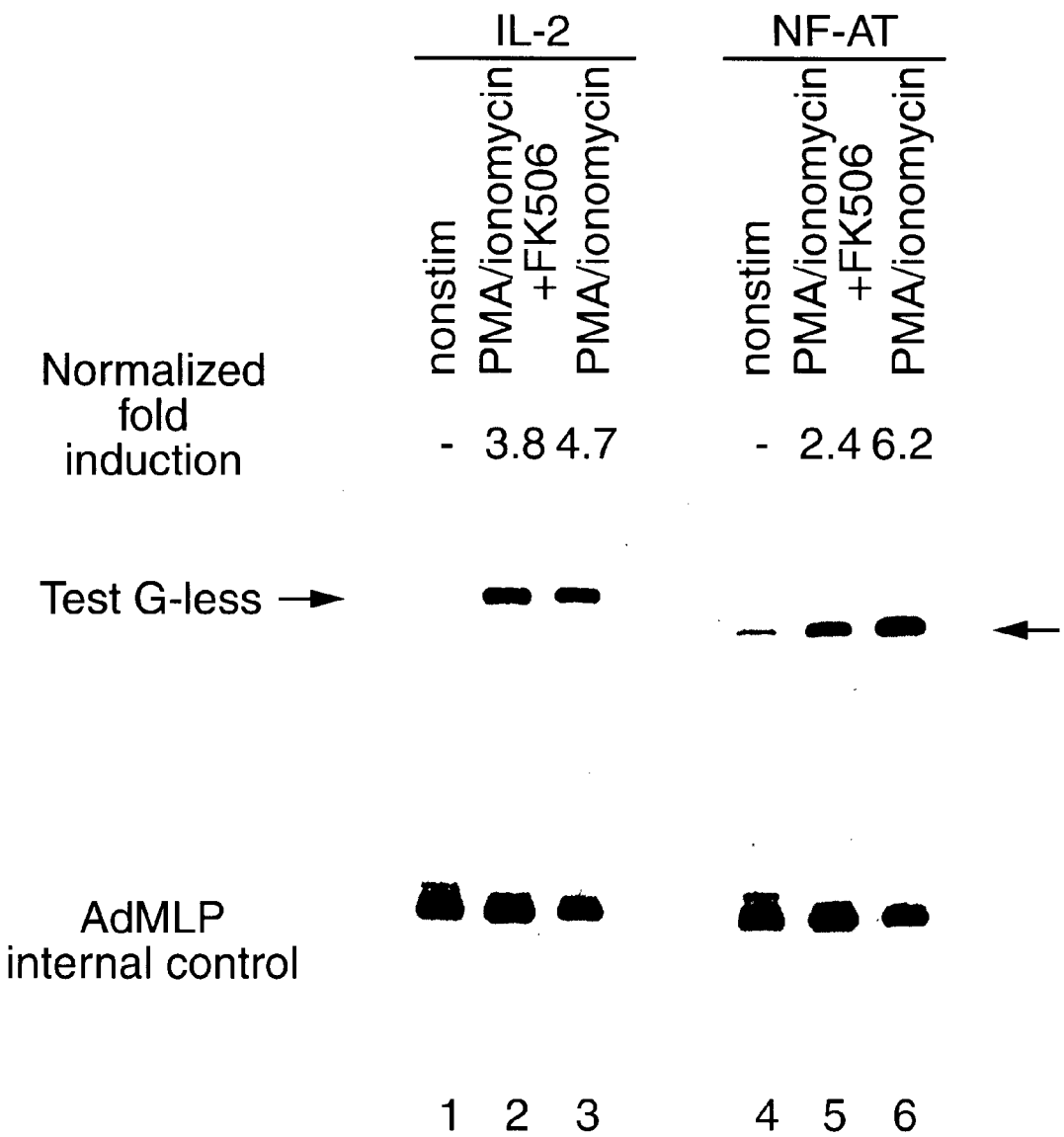
Figure 9B:
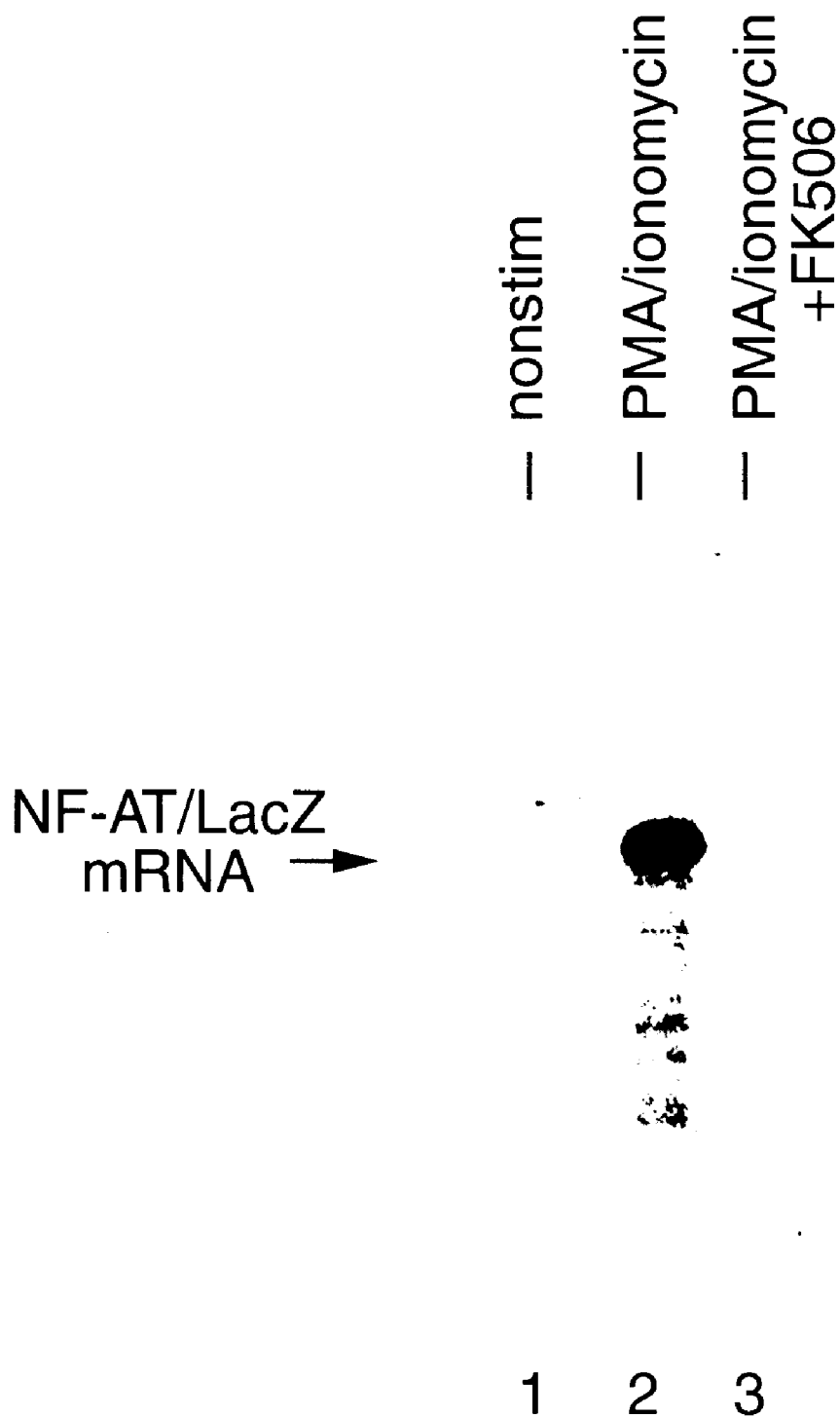

Surprisingly, nuclear extracts from Jurkat cells that had been stimulated for 2 hours with PMA and ionomycin in the presence of FK506 (10 ng/ml) transcribe the IL-2 G-less template at levels nearly equivalent to extracts from fully stimulated Jurkat cells (FIG. 9A, compare lanes 2 and 3) even though transcription of the endogenous IL-2 gene in these cells is fully inhibited (data not shown). Since most of the inhibitory effects of CsA and FK056 on IL-2 gene activation have been shown to be due to the inhibition of NF-AT function (Emmel supra; Mattila et al., supra), we also examined transcription directed by this protein. In vitro transcription directed by multimerized binding sites for the NF-AT protein was reduced 2.5-fold in nuclear extracts of stimulated/FK506-treated cells (FIG. 9A, compare lanes 5 and 6) despite the fact that NF-AT dependent transcription was totally blocked in the cells used to prepare the extracts (FIG. 9B). In these extracts, NF-AT DNA-binding activity is reduced about 50 to 80% far less than the inhibitory effects on in vivo IL-2 gene expression that are generally in excess of 99% (Mattila et al., supra), but commensurate with the effects on NF-AT dependent in vitro transcription. Thus, it appears that stimulated/FK506-treated cells contain a reduced amount of NF-AT that functions in vitro but not in vivo.

Example 7

Tandem NF-AT Binding Sites Direct Expression of T Antigen to Activated Lymphocytes in Transgenic Mice To determine whether a transcriptional promoter under the control of NF-AT regulatory sites will specifically direct expression of a linked gene to activated lymphocytes, we utilized a cell line that contains a construct in which tandem NF-AT binding sites are linked upstream of a gene encoding T antigen (Verweij et al., *J. Biol. Chem.* 265: 15788–15795).

Procedure

Total RNA was isolated from various tissues and cells using guanidium thiocyanate and hot phenol extraction. Equal amounts (10 μg)of RNA were used. RNA mapping experiments with the Sp6/T7 RNA polymerase system were done according to (Melton, D. A. NAR 12:7035–7056 (1984)). For mapping correctly initiated NF-AT-Tag mRNA, a SP6 RNA probe was transcribed from Eco RI digested pSP6IL-2 vector containing a 117 bp Xho I-Hind III fragment (–70 to +47 of NFAT-Tag). Hybridization was allowed to proceed at 42° C. for 16 h and samples were digested with 4 ug/ml RNase A and 160 unit s/ml RNase T1 at 30 ° C. for 1 h. Protected fragments were run on a 5% denaturing polyacrylamide gel and exposed to XAR-5 film.

Results

Figure 10:
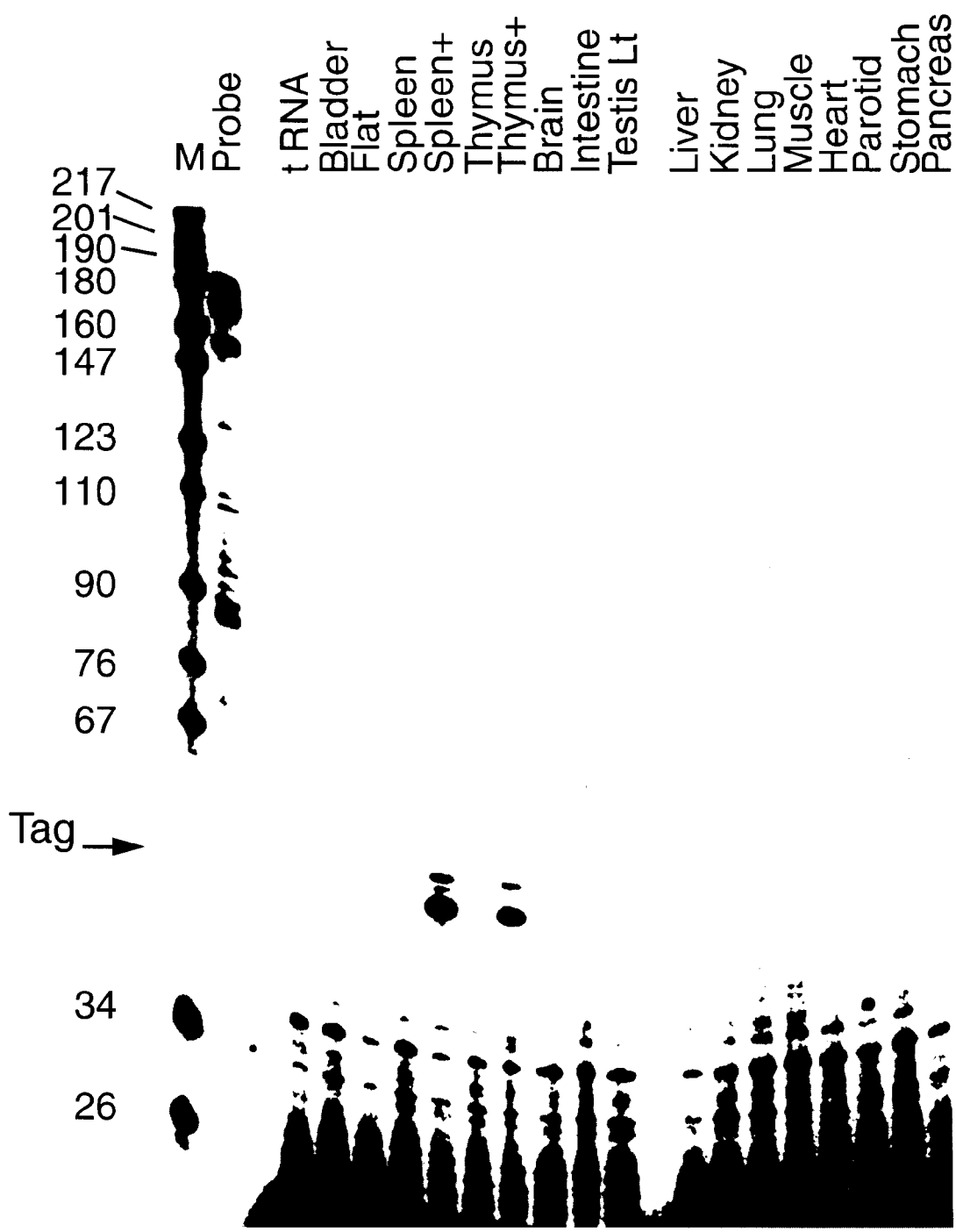

As shown in FIG. 10, only lymphoid cells transcribed the T antigen gene which was under the control of the tandem NF-AT binding sites. Thus, an array of NF-AT binding sites is useful for directing expression of a linked gene specifically to activated lymphoid cells.

Example 8

Activation of NF-AT Probably Requires Phosphorylation

Evidence for phosphorylation of NF-AT was obtained by treating nuclear extracts with calf alkaline phosphatase and examining the mobility of the NF-AT DNA-binding complex on nondenaturing gels. As shown in FIG. 11, dephosphorylation of NF-AT with calf intestinal phosphatase reduces its ability to associate with its DNA binding site (FIG. 11, lane 4).

Conclusion

Model for the Actions of FK506 and Cyclosporin A: Their Role in Preventing Nuclear Import of NF-AT A calcium stimulus induced by the antigen leads to the nuclear import of a subunit of NF-AT. Once in the nucleus, the cytosolic subunit combines with a newly induced nuclear subunit to produce a complex having both DNA-binding activity and transcriptional activity. Neither subunit alone has DNA binding activity and neither subunit alone has transcriptional activity. Cyclosporin A and FK506 prevent the import of the cytosolic component of NF-AT by either preventing the development of competence for nuclear transfer of the cytosolic component of NF-AT or by blocking the appearance of nuclear import signals for NF-AT.

Example 9

Determination of the Nucleotide and Amino Acid Sequence of Human NF-AT$_c$ cDNA This example represents the isolation and purification of this novel human NF-AT protein, NF-AT$_c$, the determination of the amino acid sequence of its fragments and the isolation and sequencing of the cDNA clone encoding this protein.

Since our previous work indicated that the cytosolic component of NF-AT was present at relatively low concentrations in human lymphoid cell lines (Northrop et al. (1993) *J. Biol Chem.* 268: 2917–2923), we chose to purify NF-AT$_c$ from bovine thymus. Accordingly, the protein was purified from bovine thymus glands obtained from newborn calves. Approximately 20 bovine thymuses were homogenized to make a cytosolic extract which was then subjected sequentially to 1) ammonium sulfate precipitation, 2) sulphopropyl Sepharose chromatography, 3) heparin agarose chromatography, 4) affinity chromatography using a multimerized binding site for NF-AT, with the sequence 5'-ACGCCCAAAGAGGAAAATTTGTTTCATACA-3' (SEQ ID NO: 39) coupled to sepharose CL4B, and 5) HPLC on a reverse phase C4 column. The resulting purified protein was subjected to cleavage with LysC/ArgC and fragments isolated by HPLC. The sequences of these individual fragments were then determined by automated Edman degradation. Sequences obtained included: LRNSDIELRKGET-DIGR (SEQ ID NO: 35) and LRNADIELR (SEQ ID NO: 40). Degenerate oligos corresponding to GETDIG (SEQ ID NO: 41) (reverse primer) and RNADIE (SEQ ID NO: 42) (forward primer) were made. The degenerate oligo PCR primers had the following sequences:

A forward: (A/C)GIAA(C/T)GCIGA(C/T)AT(A/C/T)GA(A/G) (SEQ ID NO: 43)

A reverse: ICC(A/G/T)AT(A/G)TCIGT(C/T)TCICC (SEQ ID NO: 44)

To isolate the cDNA, oligonucleotide probes were made corresponding to the determined amino acid sequence and used as PCR primers to isolate a 45 base fragment from bovine cDNA prepared from the bovine thymus. The bovine PCR product comprised the nucleotide sequence CTG CGG AAA which encodes -L-R-K-. The same 45 bp fragment can be amplified from human and mouse sources.

This bovine PCR product was then used to screen a cDNA library of the human Jurkat T cell line. Clones were isolated at frequencies of about 1 in 100,000 to 1 in 200,000. A total of five human cDNA clones of various lengths were isolated. Two overlapping clones, one containing the 5' end and one containing the 3' end were ligated together using a unique EcoRI restriction site present in each clone, to produce a full-length cDNA which corresponded in length to the messenger RNA determined by Northern blotting.

The sequence of the NF-AT$_c$ cDNA was determined by the Sanger method and the complete nucleotide and predicted amino acid sequence is shown in FIG. 12. The nucleotide sequence contained 2742 nucleotides and is shown in FIG. 12 (SEQ ID NO: 45). The cDNA encodes a protein of 716 amino acids having the amino acid sequence shown in FIG. 12 (SEQ ID NO: 38) with a predicted molecular weight of 77,870. An in-frame stop codon upstream from the initiator methionine indicates that the entire NF-AT$_c$ protein is encoded by this cDNA. The initiator methionine indicated in FIG. 12 was determined by fusing this reading frame to a glutathione transferase gene and transfecting the resultant clone into bacteria. The resultant clone produced a fusion protein of the proper molecular weight, indicating that the reading frame designated with the initiator methionine is indeed the correct reading frame. The position of the stop codon was determined by a similar procedure. In addition, the stop codon corresponds to the reading frame for nine of the determined amino acid sequences. A unique repeated sequence of 13 residues was also identified.

The total NF-AT$_c$ protein structure was aligned against individual Rel proteins using a MacIntosh shareware program called DOTALIGN utilizing the alignment parameters of the FASTA programs. Significant homology was observed that corresponded to the Rel domains of these proteins. Enhanced amino acid residue alignment was done using ALIGN from the same suite of programs. Alignment of the Rel similarity regions of NF-AT$_c$ and NF-AT$_p$ was done by hand with no insertions necessary, The Miyata alphabet (Miyata et al. (1979) *J. Mol. Evol.* 12: 214–236) was used to determine similar residues. FIG. 15 shows results of such sequence alignments.

The carboxy-terminal half of NF-AT$_c$ shows limited similarity to the DNA binding and dimerization regions of the Dorsal/Rel family of transcription factors (FIG. 4, for review, Nolan and Baltimore (1992) *Current Biology, Ltd.* 2: 211–220) however, NF-AT$_c$ appears to be the most distantly related member of the group. There are a significant number of amino acid changes resulting in charge reversals between the Rel family members and NF-AT$_c$, suggesting that charge might be conserved at these positions to maintain salt bridges. Six additional peptides obtained from the purified bovine protein are derived from the bovine homolog of NF-AT$_p$, a cDNA fragment of which was reported by McCaffrey et al. (1993) *Science* 262: 750–754). Comparison of NF-AT$_c$ and NF-AT$_p$ reveals that they are products of distinct genes with 73% amino acid identity in the Rel similarity region (FIG. 15), however, there is very little similarity outside this region. A murine cDNA for NF-AT$_c$ was isolated and the predicted protein was found to be 87% identical to human NF-AT$_c$, and distinctly different from murine NF-AT$_p$.

Example 10

Expression of NF-AT$_c$ in T and Non-T Cells

The cDNA shown in FIG. 12 was fused to the Hemophilus influenza hemaglutinin (HA) 12 amino acid epitope tag in the determined reading frame and operably linked to the SRα promoter in the vector pBJ5 (Lin et al, 1990, *Science* 249:677–679). The resultant construct was transiently transfected by electroporation into Jurkat human T lymphocytes, and into Cos fibroblast cells. Expression of the epitope-tagged NF-AT$_c$ protein was determined by Western blotting of whole cell extracts prepared from the transfected cells, using an antibody (12CA5, Berkeley Antibody Co., Calif.) that detects the HA epitope.

FIG. 13 shows that NF-AT$_c$ cDNA construct is able to express a protein of approximately 120 kDA corresponding precisely in size to that of the purified protein, in both Jurkat T cells and Cos cells (see lanes 3 and 6 labeled NF-AT*. Lane 2 shows as control, NF-AT without the epitope tag which cannot be detected in the Western blot).

Example 11

Transfection of NF-ATc Activates Transcription in Both Cos and Jurkat Cells The NF-ATc cDNA was operably linked to a portion of the SV40 early gene promoter and the HIV transcription regulatory regions in the pBJ vector. This expression vector was co-transfected into Jurkat and Cos cells with either a) three copies of NF-AT binding site linked to and directing transcription of luciferase (results shown in FIG. 14A and 14B) the entire IL-2 enhancer/promoter directing transcription of luciferase (results shown in FIG. 14B). Cytosolic extracts were prepared and luciferase assays carried out by standard procedures (de Wet et al, 1987, *Mol. Cell. Biol.* 7:724–837).

Figure 14A:
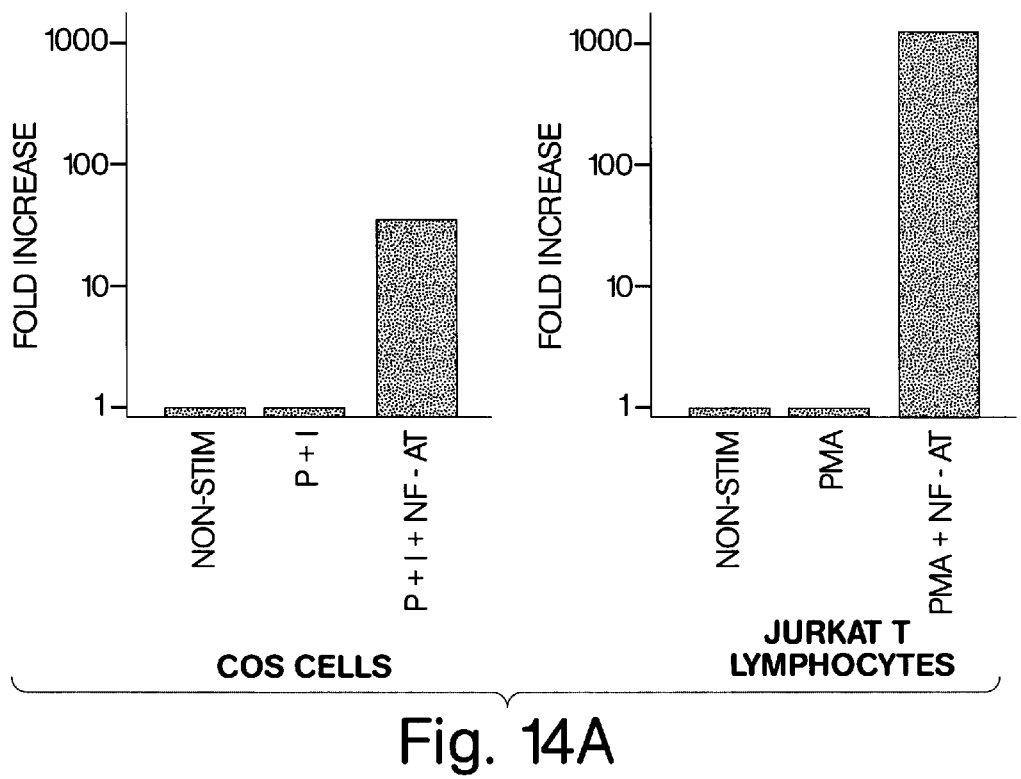
Figure 14B:
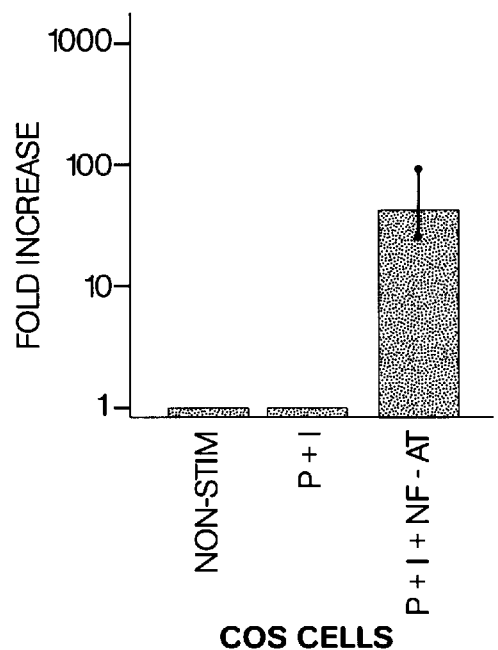

The results demonstrate that in both Cos cells and Jurkat cells, overexpression of the NF-AT$_c$ protein dramatically enhances NF-AT-dependent transcription by 50–1000 fold (see FIG. 14A). In addition, overexpression of the NF-ATc protein in Cos cells activates the IL-2 promoter, which in the absence of NF-AT$_c$ cannot otherwise be activated (see FIG. 14B).

These results indicate that the cDNA clone encodes a functional NF-AT$_c$ protein and that NF-AT$_c$ is the protein which restricts expression of interleukin-2 to T cells.

Example 12

NF-AT$_c$ mRNA and Protein Expression

NF-AT$_c$ mRNA is absent in Hela cells (FIG. 16, panel A, lane 7), a cell line incapable of IL-2 or NF-AT-dependent transcription, but is inducible in Jurkat cells (FIG. 16, panel A). This induction is sensitive to cyclosporin A, (CsA), indicating that NF-AT$_c$ may participate in an auto-stimulatory loop as CsA has been shown to block its nuclear association (Flanagan et al. (1991) *Nature* 352: 803–807). Two B cell lines, muscle tissue, Hep G2 cells and myeloid leukemia cells do not express NF-AT$_c$ mRNA (FIG. 16 panel B). These observations are consistent with the observed T cell-restricted pattern of IL-2 transcription and NF-AT activity. Previous studies (Verweij et al. (1990) *J. Biol. Chem* 265: 15788–15795) revealed NF-AT-dependent transcription predominantly in spleen, thymus and skin of transgenic mice expressing an NF-AT-dependent reporter gene. Consistent with these observations, murine NF-AT$_c$ mRNA shows the same pattern of expression (FIG. 16 panel C). Small amounts of NF-AT$_c$ expression are seen in lung and heart, however, this may be due to contamination with circulating T cells. Murine NF-AT$_p$ mRNA, also assayed by quantitative ribonuclease protection, was found to be expressed at approximately equal levels in brain, heart, thymus and spleen (FIG. 16 panel C). In contrast to NF-AT$_c$, NF-AT$_p$ was not inducible by PMA and ionomycin (FIG. 16 panel C).

Methods Specific human or mouse NF-AT$_c$ or mouse NF-AT$_p$ cDNA fragments were used as templates for the synthesis of RNA transcripts. Ribonuclease protection was done according to Melton et al. (1984) Nucl. Acids. Res. 12: 7035–7056) using 10 μg of total RNA. Splenocytes and thymocytes were isolated and treated as described (Verweij et al. (1990) *J. Biol. Chem* 265: 15788–15795) before isolating RNA, otherwise whole tissue was used.

Example 13

Functional Expression of NF-AT

NF-AT luciferase and IL-2 luciferase have been described (Northrop et al. (1993) *J. Biol. Chem.* 268: 2917–2923). β28 luciferase was constructed by inserting a trimerized HNF-I recognition site (β28) in place of the NF-AT recognition sites in NF-AT luciferase. The plasmid pSV2CAT (Gorman et al. (1982) *Mol. Cell. Biol.* 2: 1044–1050) was used as an internal control for transfection efficiency. Cells were transfected with 1.5 μg of luciferase reporter and 3 μg of expression construct as described. After 20 hours of growth, cells were stimulated for 8 hrs. with 20 ng/ml PMA plus or minus 2 μM ionomycin, and harvested for luciferase (de Wet et al. (1987) *Mol. Cell. Biol.* 7: 725–737) and CAT assays (Gorman et al. (1982) *Mol. Cell. Biol.* 2: 1044–1050).

Cos cells were transfected with epitope tagged NF-AT$_c$ as described. Cos cells, Jurkat cells, and murine thymocytes were stimulated for 3 hr with PMA and ionomycin. Hela cells were stimulated for 3 hr with PMA alone and nuclear extracts prepared as described (Fiefing et al. (1990) *Genes & Dev.* 4: 1823–1834). Cytosols were prepared from non-stimulated Cos cells. Gel mobility shifts were performed as previously described (Flanagan et al. (1991) *Nature* 352: 803–807; Northrop et al. (1993) *J. Biol. Chem.* 268: 2917–2923). Antisera were raised in mice immunized with bacterially expressed glutathione S-transferase fusion proteins using the vector pGEX-3X (Pharmacia) and purified on glutathione agarose. Fusion proteins contained NF-AT$_c$ residues 12 to 143 (immune-1) and 12 to 699 (immune-2).

NF-AT$_c$, expressed in non T cell lines specifically activated transcription from the NF-AT site and the IL-2 promoter, (FIG. 17 panel A (left), and FIG. 17 panel B). In transiently transfected Jurkat cells, overexpression of NF-AT$_c$ activated an NF-AT-dependent promoter but not an HNF-1 dependent promoter (FIG. 6 panel A (right)) or an AP-1-dependent promoter. Transfection of the NF-AT$_c$ cDNA gives rise to DNA binding activity that is indistinguishable from endogenous NF-AT (FIG. 17 panel C, lanes 1–4). Antibody directed against the HA epitope encoded by the transfected cDNA induces a supershift of the NF-AT complex indicating that NF-AT$_c$ participates in this activity. The nuclear NF-AT activity in transfected Cos cells comigrates with, and has the same binding specificity as, the native nuclear complex in T-cells (FIG. 17 panel C, lanes 4–11). Cytosolic extracts from NF-ATc, transfected Cos cells can reconstitute NF-AT DNA binding activity when mixed with Hela nuclear extract (FIG. 17 panel C, lanes 12–16) as do cytosolic extracts from T-cells (Flanagan et al. (1991) *Nature* 352: 803–807; Northrop et al. (1993) *J. Biol. Chem.* 268: 2917–2923). Antisera raised against bacterially expressed fragments of NF-AT$_c$ that have no similarity to NF-AT$_p$ are able to induce a supershift of the endogenous NF-AT complex, but not the AP-1 complex, from Jurkat cells or thymocytes (immune-1 and immune-2 respectively, FIG. 17 panel D). Immune-2 antisera reduced the DNA-protein complex produced using murine thymic nuclear extracts significantly, consistent with the relatively equal representation of NF-AT$_c$, and NF-AT$_p$ peptides in the purified protein from bovine thymus.

Example 14

NF-AT$_c$ Dominant Negative Mutant Assayed in Transient Transfection Assays

A dominant negative NF-ATC, prepared after extensive deletion analysis of the cDNA, indicated that the amino terminal domain would block NF-AT-dependent function without affecting binding. This region of the cDNA is not found in NF-AT$_p$ and hence can be used to assess the contribution of NF-AT$_c$ to the activation of the IL-2 gene. The dominant negative NF-AT$_c$ used consists of a carboxy terminal truncation of the epitope tagged NF-AT$_c$ expression plasmid (supra) extending to the PvuII site at amino acid 463. Transfection of this dominant negative resulted in more than 90% inhibition of IL-2 promoter function as well as transcription directed by the NF-AT site (FIG. 18). This effect was highly specific since transcription directed by the AP-1 site or the RSV promoter and enhancer were relatively unaffected (FIG. 18). These results strongly indicate that NF-AT$_c$ contributes substantially to IL-2 gene expression in T cells.

Dominant-negative NF-AT$_c$ polypeptides or peptidomimetics thereof can be used as pharmaceutical antagonists of NF-AT-mediated activation of T cells. In one variation, such drugs can be used as commercial research reagents for laboratory testing and analysis of T cell activation and the like, among many other uses (e.g., immunosuppressant).

Example 15

Post-Translational Modification of NF-AT$_c$

Post-translational modification of NF-AT$_c$ was investigated in cells treated with agents that activate PKC or increase intracellular Ca++. Cells were transfected with NF-AT$_c$ as described in FIG. 13 and stimulated as shown for 2 hrs plus or minus 100 ng/ml CsA. Whole cell lysates were analyzed by western blotting as in FIG. 13. The bulk of NF-AT$_c$ in cells treated with ionomycin migrates faster than that in non-treated cells and this mobility shift is inhibited by CsA (FIG. 19, lanes 1, 3–4). This is consistent with a dephosphorylation event, possibly by direct action of calcineurin (Clipstone and Crabtree (1992) *Nature* 357: 695–697), however, any of a large number of processes could produce the observed mobility changes. There is evidence that NF-AT$_p$ is a substrate for calcineurin, however, the mobility shifts produced by phosphatase treatment of NF-AT$_p$ or NF-AT$_c$ are far greater than those observed in FIG. 19. These observations indicate that NF-AT$_c$ is not a direct substrate of calcineurin. PMA treatment produces a slower migrating NF-AT$_c$ (FIG. 19, lane 2); therefore, PKC-activated pathways likely contribute to NF-AT activity by modification of NF-AT$_c$ in addition to activation of the nuclear component.

Equivalents

Although the present invention has been described in some detail by way of illustration for purposes of clarity of understanding, it will be apparent that certain changes and modifications may be practiced within the scope of the claims.

What is claimed is:

1. A method of identifying an immunosuppressive agent, comprising
   (i) providing a cell containing an NF-ATc polypeptide having an amino acid sequence encoded by a nucleic acid sequence which hybridizes under conditions of 3×SSC at 50° C. to SEQ ID No: 45;
   (ii) contacting the cell of (i) with a compound that induces nuclear translocation of said NF-ATc polypeptide;
   (iii) contacting the cell before, during or after step (ii) with a test agent;
   (iv) assaying for nuclear translocation of the NF-ATc polypeptide, wherein inhibition of nuclear transport in the cell relative to a cell that was not contacted with the test agent indicates that the test agent is a candidate immunosuppressive agent.

2. The method of claim 1, wherein assaying for nuclear translocation comprises determining the nuclear presence of the NF-ATc polypeptide.

3. The method of claim 1, wherein assaying for nuclear translocation comprises determining the nuclear association between the NF-ATc polypeptide and an NF-ATn polypeptide.

4. The method of claim 1, wherein assaying for nuclear translocation comprises determining the binding of the NF-ATc polypeptide or an NF-ATc:NF-ATn polypeptide complex to an NF-AT DNA binding sequence.

5. The method of claim 4, comprising using a gel mobility shift assay to determine the binding of the NF-ATc polypeptide or the NF-ATc:NF-ATn polypeptide complex to the NF-AT DNA binding sequence.

6. The method of claim 1, further comprising determining the level of expression of a test nucleic acid linked to an NF-AT DNA binding sequence.

7. The method of claim 1, wherein the compound of step (ii) stimulates Ca++ release in the cell.

8. The method of claim 7, wherein the compound of step (ii) is ionomycin.

9. The method of claim 1, wherein assaying for nuclear translocation includes determining the level of NF-ATccontaining complexes including an NF-ATn polypeptide, wherein the presence of a lower level of the NF-AT complex relative to a cell that has not been contacted with a test agent indicates that the test agent is a candidate immunosuppressive agent.

10. The method of claim 9 wherein assaying for nuclear translocation includes determining the level of the NF-AT complex bound to an NF-AT binding sequence, wherein the presence of a lower level of bound NF-AT complex relative to that in a cell that has not been contacted with the test agent indicates that the test agent is a candidate immunosuppressive agent.

11. A method for identifying an immunosuppressive agent, comprising
   (i) contacting a purified NF-ATc polypeptide or cell extract containing an NF-ATc polypeptide with a purified NF-ATn polypeptide or a cell extract containing an NF-ATn polypeptide and a test agent, under conditions which permit the formation of an NF-AT complex, wherein the NF-ATc polypeptide has an amino acid sequence encoded by a nucleic acid sequence which hybridizes under conditions of 3×SSC at 50° C. to SEQ ID No: 45, and
   (ii) determining the level of NF-AT complex formed, wherein a lower level of NF-AT complex relative to the level of NF-AT complex formation in the absence of the test agent indicates that the test agent is a candidate immunosuppressive agent.

12. The method of claim 11, wherein the NF-ATc polypeptide or NF-ATn polypeptide is immobilized.

13. The method of claim 1, wherein the cell further includes an NF-AT regulated enhancer region linked to a test nucleic acid, and assaying for nuclear translocation includes detecting expression of the test nucleic acid, wherein a lower level of expression of the test nucleic acid relative to its level of expression in a cell that was not contacted with the test agent indicates that the test agent is a candidate immunosuppressive agent.

14. The method of claim 13, wherein the test nucleic acid encodes a polypeptide which is essential for cell proliferation or viability.

15. The method of claim 1, wherein the cell further includes an NF-AT regulated enhancer region linked to a test nucleic acid, and assaying for nuclear translocation includes detecting expression of the test nucleic acid, wherein a higher level of expression of the test nucleic acid relative to its level of expression in a cell that was not contacted with the test agent indicates that the test agent is a candidate immunostimulatory agent.

16. The method of claim 15, wherein the test nucleic acid encodes a polypeptide which is essential for cell proliferation or induces cell death.

17. A method for identifying an immune regulating agent, comprising
   (i) contacting a cell or a cell extract containing an NF-ATc polypeptide having an amino acid sequence encoded by a nucleic acid sequence which hybridizes under conditions of 3×SSC at 50° C. to SEQ ID No: 45 with a test agent; and
   (ii) determining the level of phosphorylation of the NF-ATc polypeptide, wherein a difference in the level of phosphorylation relative to that of a cell or cell extract that was not contacted with the test agent indicates that the test agent is a candidate immune regulating agent.

18. The method of claim 17, further comprising contacting the cell with a compound which induces the nuclear translocation of the NF-ATc polypeptide.

19. A method of any one of claims 1, 9, 10, 13, 15, and 17, wherein the NF-ATc polypeptide is encoded by a heterologous nucleic acid in the cell.

20. A method of claim 19, wherein the NF-ATc polypeptide or portion thereof comprises at least 25 amino acids having an amino acid sequence which is substantially identical to an amino acid sequence set forth in SEQ ID NO: 46.

21. A method of claim 19, wherein the NF-ATc polypeptide or portion thereof is encoded by a nucleic acid which hybridizes under stringent conditions to a nucleic acid having the nucleotide sequence set forth in SEQ ID NO: 45 or the complement thereof.

* * * * *